United States Patent
Grether et al.

(10) Patent No.: US 8,648,099 B2
(45) Date of Patent: Feb. 11, 2014

(54) 3-PYRIDINE CARBOXYLIC ACID HYDRAZIDES

(75) Inventors: Uwe Grether, Efringen-Kirchen (DE); Paul Hebeisen, Basel (CH); Peter Mohr, Basel (CH); Fabienne Ricklin, Hombourg (FR); Stephan Roever, Inzlingen (DE)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 13/609,429

(22) Filed: Sep. 11, 2012

(65) Prior Publication Data

US 2013/0065876 A1 Mar. 14, 2013

(30) Foreign Application Priority Data

Sep. 12, 2011 (EP) .................... 11180929

(51) Int. Cl.
| | | |
|---|---|---|
| *A61K 31/44* | (2006.01) | |
| *A01N 43/40* | (2006.01) | |
| *C07D 213/62* | (2006.01) | |
| *C07D 213/78* | (2006.01) | |
| *C07D 211/72* | (2006.01) | |
| *C07D 211/84* | (2006.01) | |

(52) U.S. Cl.
USPC .......................... 514/350; 546/298

(58) Field of Classification Search
USPC .......................... 514/350; 546/298
See application file for complete search history.

(56) References Cited

FOREIGN PATENT DOCUMENTS

| WO | 2006/106054 | 10/2006 |
| WO | WO 2007011760 A2 * | 1/2007 |
| WO | 2007/147746 | 12/2007 |
| WO | 2008/040651 | 4/2008 |

OTHER PUBLICATIONS

International Search Report and Written Opinion for PCT/EP2012/067469 dated Oct. 25, 2012.
Despres et al., Atherosclerosis Suppl 6(1):50 ( 2005).
Szmitko et al., Atherosclerosis 199(2):248-256 ( 2008).

* cited by examiner

*Primary Examiner* — Sarah Pihonak

(57) ABSTRACT

The present invention relates to compounds of formula I,

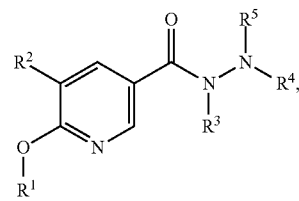

wherein $R^1$ to $R^5$ are defined in the description and claims, and to pharmaceutically acceptable salts thereof. The present invention relates also to the manufacture of said compounds, pharmaceutical compositions containing them and methods for the treatment and/or prophylaxis of diseases which can be treated with HDL-cholesterol raising agents, such as dyslipidemia, atherosclerosis and cardiovascular diseases.

17 Claims, No Drawings

3-PYRIDINE CARBOXYLIC ACID HYDRAZIDES

PRIORITY TO RELATED APPLICATION(S)

This application claims the benefit of European Patent Application No. 11180929.9, filed Sep. 12, 2011, which is hereby incorporated by reference in its entirety.

FIELD OF THE INVENTION

The present invention is concerned with 3-pyridine carboxylic acid hydrazides being HDL-cholesterol raising agents, their manufacture, pharmaceutical compositions containing them and their use as therapeutically active substances.

The compounds of the invention are HDL-cholesterol raising agents and can therefore be used in the therapeutic and/or prophylactic treatment of diseases and disorders such as dyslipidemia, atherosclerosis and cardiovascular diseases.

BACKGROUND OF THE INVENTION

Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non-esterified cholesterol). There are 3 different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (10-12%). As a result, there is a significant unmet medical need for a well-tolerated agent which can significantly elevate plasma HDL levels.

Thus, HDL-cholesterol raising agents can be useful as medicaments for the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, improvement of glycemic control, obesity or endotoxemia.

In addition, HDL-cholesterol raising agents may be used in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesteryl ester transfer protein (CETP) inhibitor, a cholesterol absorption inhibitor, a cholesterol synthesis inhibitor, a fibrate, niacin, preparations containing niacin or other HM74a agonists, an ion-exchange resin, an antioxidant, an ACAT inhibitor or a bile acid sequestrant.

Object of the present invention is therefore to provide compounds that are potent HDL-cholesterol raising agents. It has been found that the compounds of formula I of the present invention are very useful for the treatment and/or prophylaxis of diseases and disorders which can be treated with HDL-cholesterol raising agents, i.e. the compounds of formula I are especially useful for the treatment and/or prevention of dyslipidemia, atherosclerosis and cardiovascular diseases. Object of the present invention is also to provide compounds which are, at therapeutically active concentrations that increase HDL-concentrations, not interacting with the CB1 receptor. This is because CB1 receptor ligands may compromise the therapeutic utility of HDL-cholesterol raising agents, as both agonists and antagonists of the CB1 receptor have the potential to lead to side effects.

SUMMARY OF THE INVENTION

The present invention relates to a compound according to formula I,

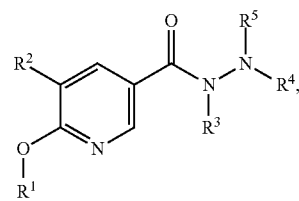

wherein
$R^1$ is selected from the group consisting of $C_{1-7}$-alkyl, $C_{3-7}$-cycloalkyl, $C_{3-7}$-cycloalkyl-$C_{1-7}$-alkyl, hydroxy-$C_{1-7}$-alkyl, $C_{1-7}$-alkoxy-$C_{1-7}$-alkyl, and halogen-$C_{1-7}$-alkyl;
$R^2$ is selected from the group consisting of
phenyl, said phenyl being unsubstituted or substituted by one, two or three groups selected from the group consisting of $C_{1-7}$-alkyl, $C_{1-7}$-alkoxy, halogen, halogen-$C_{1-7}$-alkyl, halogen-$C_{1-7}$-alkoxy, amino, azido and cyano,
$C_{3-7}$-cycloalkyl,
furyl, and
heterocyclyl, said heterocyclyl having 3 to 7 ring atoms, comprising one, two or three heteroatoms selected from N, O and S and being unsubstituted or substituted by a $C_{1-7}$-alkoxycarbonyl group;
$R^3$ is hydrogen;
$R^4$ is hydrogen or $C_{1-7}$-alkyl;
or $R^3$ and $R^4$ are —(CH$_2$)$_3$— and together with the nitrogen atoms to which they are attached form a 5-membered heterocyclic ring; and
$R^5$ is selected from the group consisting of hydrogen, halogen-$C_{1-7}$-alkyl, hydroxyl-$C_{1-7}$-alkyl, $C_{1-7}$-alkoxycarbonyl,
phenyl, said phenyl being unsubstituted or substituted by one, two or three groups selected from the group consisting of $C_{1-7}$-alkyl, halogen, halogen-$C_{1-7}$-alkyl and cyano,
heteroaryl, said heteroaryl being unsubstituted or substituted by one or two groups selected from the group consisting of $C_{1-7}$-alkyl, halogen and halogen-$C_{1-7}$-alkyl; and heteroaryl-$C_{1-7}$-alkyl, said heteroaryl-$C_{1-7}$-alkyl being unsubstituted or substituted by one or two groups selected from the group consisting of $C_{1-7}$-alkyl, halogen and halogen-$C_{1-7}$-alkyl;

or $R^4$ and $R^5$ together with the nitrogen atom to which they are attached form a 4-, 5-, 6- or 7-membered heterocyclic ring optionally containing a further heteroatom or group selected from nitrogen, oxygen, sulfur, sulfinyl and sulfonyl, said heterocyclic ring being unsubstituted or substituted by one, two or three groups independently selected from $C_{1-7}$-alkyl, hydroxy, oxo, hydroxy-$C_{1-7}$-alkyl, $C_{1-7}$-alkoxy, $C_{1-7}$-alkoxy-$C_{1-7}$-alkyl, heterocyclyl-$C_{1-7}$-alkyl, $C_{1-7}$-alkylcarbonyl and $C_{1-7}$-alkylsulfonyl;

or a pharmaceutically acceptable salt thereof.

The present invention relates also to a pharmaceutical composition comprising the aforementioned compound and a pharmaceutically acceptable carrier and/or adjuvant.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, particularly of one to four carbon atom(s).

The term "compound(s) of this invention" and "compound(s) of the present invention" refers to compounds of formula I and stereoisomers, solvates or salts thereof (e.g., pharmaceutically acceptable salts).

The term "alkyl", alone or in combination with other groups, refers to a branched or straight-chain monovalent saturated aliphatic hydrocarbon radical of one to twenty carbon atoms, particularly one to sixteen carbon atoms, more particularly one to ten carbon atoms.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls, in particular methyl, ethyl, propyl, isopropyl and tert-butyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, in particular methoxy.

The term "lower alkoxyalkyl" or "$C_{1-7}$-alkoxy-$C_{1-7}$-alkyl" refers to a lower alkyl group as defined above which is mono- or multiply substituted with a lower alkoxy group as defined above. Examples of lower alkoxyalkyl groups are e.g. —$CH_2$—O—$CH_3$, —$CH_2$—$CH_2$—O—$CH_3$, —$CH_2$—O—$CH_2$—$CH_3$ and the groups specifically exemplified herein. More particularly, lower alkoxyalkyl is methoxyethyl.

The term hydroxy means the group —OH.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the particular interesting lower hydroxyalkyl groups are hydroxymethyl or hydroxyethyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by a cycloalkyl group. Among the lower cycloalkylalkyl groups of particular interest resides cyclopropylmethyl.

The term "halogen" refers to fluoro, chloro, bromo and iodo, with fluoro, chloro and bromo being of particular interest. More particularly, halogen refers to fluoro and chloro.

The term "lower halogenalkyl" or "halogen-$C_{1-7}$-alkyl" refers to lower alkyl groups which are mono- or multiply substituted with halogen, particularly with fluoro or chloro, most particularly with fluoro. Examples of lower halogenalkyl groups are e.g. —$CF_3$, —$CHF_2$, —$CH_2Cl$, —$CH_2CF_3$, —$CH(CF_3)_2$, —$CF_2$—$CF_3$, —$CH_2$—$CH_2$-$CF_3$, —$CH(CH_3)$—$CF_3$ and the groups specifically exemplified herein. Of particular interest are the groups trifluoromethyl (—$CF_3$) and 2,2,2-trifluoroethyl (—$CH_2CF_3$).

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, particularly fluoro or chloro, most particularly fluoro. Among the lower halogenalkoxy groups of particular interest are trifluoromethoxy, difluoromethoxy, fluoromethoxy and chloromethoxy, more particularly trifluoromethoxy.

The term amino means the group —$NH_2$.

The term "cyano" means the group —CN.

The term "azido" means the group —$N_3$.

The term "lower alkoxycarbonyl" or "$C_{1-7}$-alkoxycarbonyl" refers to the group —COOR, wherein R is lower alkyl and the term "lower alkyl" has the previously given significance. Lower alkoxycarbonyl groups of particular interest are methoxycarbonyl or ethoxycarbonyl.

The term "lower alkylcarbonyl" or "$C_{1-7}$-alkylcarbonyl" refers to the group —COR, wherein R is lower alkyl and the term "lower alkyl" has the previously given significance. A lower alkylcarbonyl group of particular interest is acetyl.

The term "sulfinyl" means the group —S(O)—.

The term "sulfonyl" means the group —$S(O)_2$—.

The term "lower alkylsulfonyl" or "$C_{1-7}$-alkylsulfonyl" means the group —$S(O)_2$—R, wherein R is a lower alkyl group as defined above. A lower alkylsulfonyl group of particular interest is methylsulfonyl.

The term "heteroaryl" refers to an aromatic 5- or 6-membered ring which can comprise one, two or three atoms selected from N, O and S. Examples of heteroaryl groups are e.g. furanyl, pyridyl, pyrazinyl, pyrimidinyl, pyridazinyl, thienyl, isoxazolyl, thiazolyl, isothiazolyl, thiadiazolyl, oxazolyl, imidazolyl, pyrazolyl, triazolyl, oxadiazolyl, oxatriazolyl, tetrazolyl, pentazolyl, or pyrrolyl. The term "heteroaryl" also includes bicyclic groups comprising two 5- or 6-membered rings, in which one or both rings are aromatic and can contain one, two or three atoms selected from nitrogen, oxygen or sulphur, such as quinolinyl, isoquinolinyl, cinnolinyl, pyrazolo[1,5-a]pyridyl, imidazo[1,2-a]pyridyl, quinoxalinyl, benzothiazolyl, benzotriazolyl, indolyl, indazolyl, and 3,4-dihydro-2H-pyrido[3,2-b][1,4]oxazinyl. Heteroaryl groups of particular interest are of isoxazolyl, pyrazolyl, oxadiazolyl, thiazolyl, pyridyl, pyridazinyl, pyrimidinyl and pyrazinyl. More particularly, heteroaryl is pyridyl or pyridazinyl.

The term "heterocyclyl" refers to a saturated or partly unsaturated 3-, 4-, 5-, 6- or 7-membered ring which can comprise one, two or three heteroatoms selected from N, O and S. Examples of heterocyclyl rings include piperidinyl, piperazinyl, azetidinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, oxiranyl, thiadiazolylidinyl, oxetanyl, dioxolanyl, dihydrofuranyl, tetrahydrofuranyl, dihydropyranyl, tetrahydropyranyl, and thiomorpholinyl. Of particular interest are piperidinyl and tetrahydropyranyl.

The term "lower heterocyclylalkyl" or "heterocyclyl-$C_{1-7}$-alkyl" refers to lower alkyl groups as defined above wherein at least one of the hydrogen atoms of the lower alkyl group is replaced by a heterocyclyl group as defined above.

The term "oxo" means that a C-atom of the heterocyclyl or heteroaryl ring may be substituted by =O, thus meaning that the heterocyclyl or heteroaryl ring may contain one or more carbonyl (—CO—) groups.

"Isomeric forms" are all forms of a compound characterized by having an identical molecular formula but that differ in the nature or the sequence of bonding of their atoms or in the arrangement of their atoms in space. Particularly, the isomeric forms differ in the arrangement of their atoms in space and can also be termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center".

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable salts" refers to those salts which retain the biological effectiveness and properties of the free bases or free acids, and which do not possess any own properties that are undesirable. The salts are formed with inorganic acids such as hydrochloric acid, hydrobromic acid, sulfuric acid, nitric acid, phosphoric acid and the like, particularly hydrochloric acid, and organic acids such as formic acid, acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. Thus, preferred "pharmaceutically acceptable salts" include the acetate, bromide, chloride, formate, fumarate, maleate, mesylate, nitrate, oxalate, phosphate, sulfate, tartrate and tosylate salt of compounds of formula I. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, diethylamine, lysine, arginine, N-ethylpiperidine, piperidine, piperazine and the like. The compound of formula I can also be present in the form of zwitterions or in the form of hydrates. Particularly preferred pharmaceutically acceptable salts of compounds of formula I are the hydrochloride salts.

The present invention relates to compounds of the formula

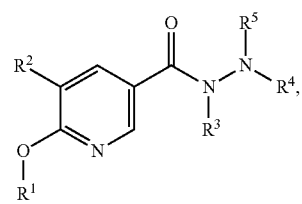

wherein
$R^1$ is selected from the group consisting of $C_{1-7}$-alkyl,
$C_{3-7}$-cycloalkyl,
$C_{3-7}$-cycloalkyl-$C_{1-7}$-alkyl,
hydroxy-$C_{1-7}$-alkyl,
$C_{1-7}$-alkoxy-$C_{1-7}$-alkyl, and
halogen-$C_{1-7}$-alkyl;
$R^2$ is selected from the group consisting of
phenyl, said phenyl being unsubstituted or substituted by one, two or three groups selected from the group consisting of $C_{1-7}$-alkyl, $C_{1-7}$-alkoxy, halogen, halogen-$C_{1-7}$-alkyl, halogen-$C_{1-7}$-alkoxy, amino, azido and cyano,
$C_{3-7}$-cycloalkyl,
furyl, and
heterocyclyl, said heterocyclyl having 3 to 7 ring atoms, comprising one, two or three heteroatoms selected from N, O and S and being unsubstituted or substituted by a $C_{1-7}$-alkoxycarbonyl group;
$R^3$ is hydrogen;
$R^4$ is hydrogen or $C_{1-7}$-alkyl;
or $R^3$ and $R^4$ are —(CH$_2$)$_3$— and together with the nitrogen atoms to which they are attached form a 5-membered heterocyclic ring;
$R^5$ is selected from the group consisting of hydrogen,
halogen-$C_{1-7}$-alkyl, hydroxyl-$C_{1-7}$-alkyl, $C_{1-7}$-alkoxycarbonyl,
phenyl, said phenyl being unsubstituted or substituted by one, two or three groups selected from the group consisting of $C_{1-7}$-alkyl, halogen, halogen-$C_{1-7}$-alkyl and cyano,
heteroaryl, said heteroaryl being unsubstituted or substituted by one or two groups selected from the group consisting of $C_{1-7}$-alkyl, halogen and halogen-$C_{1-7}$-alkyl; and
heteroaryl-$C_{1-7}$-alkyl, said heteroaryl-$C_{1-7}$-alkyl being unsubstituted or substituted by one or two groups selected from the group consisting of $C_{1-7}$-alkyl, halogen and halogen-$C_{1-7}$-alkyl;
or $R^4$ and $R^5$ together with the nitrogen atom to which they are attached form a 4-, 5-, 6- or 7-membered heterocyclic ring optionally containing a further heteroatom or group selected from nitrogen, oxygen, sulfur, sulfinyl and sulfonyl,
said heterocyclic ring being unsubstituted or substituted by one, two or three groups independently selected from $C_{1-7}$-alkyl, hydroxy, oxo, hydroxy-$C_{1-7}$-alkyl, $C_{1-7}$-alkoxy, $C_{1-7}$-alkoxy-$C_{1-7}$-alkyl, heterocyclyl-$C_{1-7}$-alkyl, $C_{1-7}$-alkylcarbonyl and $C_{1-7}$-alkylsulfonyl;
or pharmaceutically acceptable salts thereof.

Compounds of formula I according to the present invention are in particular those, wherein $R^1$ is selected from the group consisting of $C_{3-7}$-cycloalkyl, $C_{3-7}$-cycloalkyl-$C_{1-7}$-alkyl and halogen-$C_{1-7}$-alkyl. More particularly, $R^1$ is halogen-$C_{1-7}$-alkyl.

Compounds of formula I according to the invention are furthermore those, wherein $R^2$ is phenyl, said phenyl being unsubstituted or substituted by one, two or three groups selected from the group consisting of hydrogen, $C_{1-7}$-alkyl, $C_{1-7}$-alkoxy, halogen, halogen-$C_{1-7}$-alkyl, halogen-$C_{1-7}$-alkoxy, amino, azido and cyano, or $R^2$ is $C_{3-7}$-cycloalkyl.

In particular, the invention relates to compounds of formula I, wherein $R^2$ is phenyl, said phenyl being unsubstituted or substituted by one, two or three groups selected from the group consisting of hydrogen, $C_{1-7}$-alkyl, $C_{1-7}$-alkoxy, halogen, halogen-$C_{1-7}$-alkyl, halogen-$C_{1-7}$-alkoxy, amino, azido and cyano. In particular, compounds of formula I are those, wherein $R^2$ is phenyl substituted by one, two or three groups selected from the group consisting of $C_{1-7}$-alkyl, $C_{1-7}$-halogen and halogen-$C_{1-7}$-alkyl. More particularly, $R^2$ is selected from 4-chlorophenyl, 3-fluorophenyl, 4-cyanophenyl and 4-chloro-3-fluorophenyl.

Another group of compounds of formula I according to the present invention are those, wherein $R^2$ is $C_{3-7}$-cycloalkyl. In particular, $R^2$ is cyclopentyl or cyclohexyl.

A further group of compounds of formula I according to the invention are those, wherein $R^2$ is heterocyclyl, said heterocyclyl having 3 to 7 ring atoms, comprising one, two or three heteroatoms selected from N, O and S and being unsubstituted or substituted by a $C_{1-7}$-alkoxycarbonyl group. In particular, $R^2$ is piperidinyl, said piperidinyl being unsubstituted or substituted by a $C_{1-7}$-alkoxycarbonyl group, for example tert-butoxycarbonyl.

A further group of compounds of formula I are those, wherein $R^2$ is furyl, more particularly furan-2-yl.

Compounds of formula I according to the present invention are further those, wherein $R^3$ is hydrogen.

Another group of compounds of formula I are those, wherein $R^3$ and $R^4$ are —$(CH_2)_3$— and together with the nitrogen atoms to which they are attached form a 5-membered heterocyclic ring. In particular, the invention relates to compounds of formula I, wherein $R^3$ and $R^4$ are —$(CH_2)_3$— and together with the nitrogen atoms to which they are attached form a 5-membered heterocyclic ring and $R^5$ is $C_{1-7}$-alkoxycarbonyl.

A specific example is t-butyl 2-[(5-(4-chlorophenyl)-6-(2,2,2-trifluoroethoxy)-3-pyridinyl)carbonyl]-pyrazolidine-1-carboxylate.

A further group of compounds of formula I according to the invention are those, wherein $R^3$ is hydrogen and wherein $R^4$ and $R^5$ together with the nitrogen atom to which they are attached form a 4-, 5-, 6- or 7-membered heterocyclic ring optionally containing a further heteroatom or group selected from nitrogen, oxygen, sulfur, sulfinyl and sulfonyl, said heterocyclic ring being unsubstituted or substituted by one, two or three groups independently selected from $C_{1-7}$-alkyl, hydroxy, oxo, hydroxy-$C_{1-7}$-alkyl, $C_{1-7}$-alkoxy, $C_{1-7}$-alkoxy-$C_{1-7}$-alkyl, heterocyclyl-$C_{1-7}$-alkyl, $C_{1-7}$-alkylcarbonyl and $C_{1-7}$-alkylsulfonyl.

In particular, the invention relates to compounds of formula I, wherein $R^3$ is hydrogen and $R^4$ and $R^5$ together with the nitrogen atom to which they are attached form a heterocyclic ring selected from the group consisting of azetidinyl, pyrrolidinyl, oxazolidinyl, piperidinyl, piperazinyl, morpholinyl and 1,1-dioxido-4-thiomorpholinyl, said heterocyclic ring being unsubstituted or substituted by one, two or three groups independently selected from $C_{1-7}$-alkyl, hydroxy, oxo, hydroxy-$C_{1-7}$-alkyl, $C_{1-7}$-alkoxy, $C_{1-7}$-alkoxy-$C_{1-7}$-alkyl, heterocyclyl-$C_{1-7}$-alkyl, $C_{1-7}$-alkylcarbonyl and $C_{1-7}$-alkylsulfonyl. More particularly, $R^4$ and $R^5$ together with the nitrogen atom to which they are attached form a heterocyclic ring selected from piperidinyl and piperazinyl, said heterocyclic ring being substituted by hydroxy and hydroxy-$C_{1-7}$-alkyl.

Specific examples for these compounds are the following:
5-(4-chlorophenyl)-N-morpholino-6-(2,2,2-trifluoroethoxy)-3-pyridinecarboxamide,
5-(4-chloro-phenyl)-N-(1,1-dioxido-4-thiomorpholinyl)-6-(2,2,2-trifluoro-ethoxy)-3-pyridinecarboxamide,
5-(4-chlorophenyl)-N-(4-hydroxypiperidin-1-yl)-6-(2,2,2-trifluoroethoxy)-3-pyridinecarboxamide,
5-(4-chlorophenyl)-N-(5-(morpholinomethyl)-2-oxooxazolidin-3-yl)-6-(2,2,2-trifluoroethoxy)-3-pyridinecarboxamide,
5-(4-chlorophenyl)-6-(cyclopropylmethoxy)-N-(4-hydroxypiperidin-1-yl)-3-pyridinecarboxamide,
5-(4-chlorophenyl)-6-cyclobutoxy-N-(4-hydroxypiperidin-1-yl)-3-pyridinecarboxamide,
5-cyclohexyl-N-(4-hydroxypiperidin-1-yl)-6-(2,2,2-trifluoroethoxy)-3-pyridinecarboxamide,
5-(4-chlorophenyl)-N-(4-(methylsulfonyl)piperazin-1-yl)-6-(2,2,2-trifluoroethoxy)-3-pyridinecarboxamide,
5-cyclopentyl-N-morpholino-6-(2,2,2-trifluoroethoxy)-3-pyridinecarboxamide,
5-cyclopentyl-N-(2-oxopyrrolidin-1-yl)-6-(2,2,2-trifluoroethoxy)-3-pyridinecarboxamide,
(S)-5-cyclopentyl-N-(2-(methoxymethyl)pyrrolidin-1-yl)-6-(2,2,2-trifluoroethoxy)-3-pyridinecarboxamide,
5-cyclohexyl-N-morpholino-6-(2,2,2-trifluoroethoxy)-3-pyridinecarboxamide,
5-cyclohexyl-N-(pyrrolidin-1-yl)-6-(2,2,2-trifluoroethoxy)-3-pyridinecarboxamide,
5-cyclohexyl-N—((S)-2-methoxymethyl-pyrrolidin-1-yl)-6-(2,2,2-trifluoro-ethoxy)-3-pyridinecarboxamide,
5-(4-chlorophenyl)-N-(4-(2-hydroxyethyl)piperidin-1-yl)-6-(2,2,2-trifluoroethoxy)-3-pyridinecarboxamide,
5-(4-chlorophenyl)-N-(4-(2-hydroxyethyl)piperazin-1-yl)-6-(2,2,2-trifluoroethoxy)-3-pyridinecarboxamide,
5-(4-chlorophenyl)-N-(4-(hydroxymethyl)piperidin-1-yl)-6-(2,2,2-trifluoroethoxy)-3-pyridinecarboxamide,
5-(4-chlorophenyl)-N-(4-methyl-3-oxopiperazin-1-yl)-6-(2,2,2-trifluoroethoxy)-3-pyridinecarboxamide,
5-(4-chlorophenyl)-N-(3-hydroxyazetidin-1-yl)-6-(2,2,2-trifluoroethoxy)-3-pyridinecarboxamide,
5-cyclopropyl-N-(1,1-dioxo-1λ6-thiomorpholin-4-yl)-6-(2,2,2-trifluoro-ethoxy)-nicotinamide,
5-cyclopropyl-N-morpholin-4-yl-6-(2,2,2-trifluoro-ethoxy)-nicotinamide,
5-cyclopropyl-N—((S)-2-methoxymethyl-pyrrolidin-1-yl)-6-(2,2,2-trifluoro-ethoxy)-nicotinamide,
5-(4-cyano-phenyl)-N-(4-hydroxy-piperidin-1-yl)-6-(2,2,2-trifluoro-ethoxy)-nicotinamide,
5-(4-cyano-phenyl)-N-morpholin-4-yl-6-(2,2,2-trifluoro-ethoxy)-nicotinamide,
5-(4-cyano-phenyl)-N-[4-(2-hydroxy-ethyl)-piperidin-1-yl]-6-(2,2,2-trifluoro-ethoxy)-nicotinamide,
5-cyclopropyl-N-((2R,6S)-2,6-dimethyl-morpholin-4-yl)-6-(2,2,2-trifluoro-ethoxy)-nicotinamide,
5-cyclopropyl-6-cyclopropylmethoxy-N-((2R,6S)-2,6-dimethyl-morpholin-4-yl)-nicotinamide,
6-cyclobutoxy-5-furan-2-yl-N-(4-hydroxy-piperidin-1-yl)-nicotinamide,
or pharmaceutically acceptable salts thereof.

Another group of compounds of formula I according to the invention are those, wherein
$R^3$ is hydrogen and
$R^4$ is hydrogen or $C_{1-7}$-alkyl, and
$R^5$ is selected from the group consisting of hydrogen, halogen-$C_{1-7}$-alkyl, hydroxyl-$C_{1-7}$-alkyl, $C_{1-7}$-alkoxycarbonyl, phenyl, said phenyl being unsubstituted or substituted by one, two or three groups selected from the group consisting of $C_{1-7}$-alkyl, halogen, halogen-$C_{1-7}$-alkyl and cyano, heteroaryl, said heteroaryl being unsubstituted or substituted by one or two groups selected from the group consisting of $C_{1-7}$-alkyl, halogen and halogen-$C_{1-7}$-alkyl; and heteroaryl-$C_{1-7}$-alkyl, said heteroaryl-$C_{1-7}$-alkyl being unsubstituted or substituted by one or two groups selected from the group consisting of $C_{1-7}$-alkyl, halogen and halogen-$C_{1-7}$-alkyl.

In particular, the invention relates to compounds of formula I according to the invention, wherein $R^4$ is hydrogen or methyl and $R^5$ is selected from the group consisting of hydrogen, halogen-$C_{1-7}$-alkyl, hydroxy-$C_{1-7}$-alkyl, phenyl, 4-fluorophenyl, pyridin-4-ylmethyl and 6-chloropyridazin-3-yl.

Specific examples for such compounds of formula I are the following:

5-(4-chlorophenyl)-6-(2,2,2-trifluoroethoxy)-N'-(2,2,2-trifluoroethyl)-3-pyridinecarboxylic acid hydrazide,
5-(4-chloro-phenyl)-6-(2,2,2-trifluoro-ethoxy)-3-pyridinecarboxylic acid N'-methyl-N'-phenyl-hydrazide,
5-(4-chlorophenyl)-N'-(6-chloropyridazin-3-yl)-N'-methyl-6-(2,2,2-trifluoroethoxy)-3-pyridinecarboxylic acid hydrazide,
5-(4-chloro-3-fluorophenyl)-6-(2,2,2-trifluoroethoxy)-3-pyridinecarboxylic acid hydrazide,
N'-(6-chloropyridazin-3-yl)-5-cyclopentyl-N'-methyl-6-(2,2,2-trifluoroethoxy)-3-pyridinecarboxylic acid hydrazide,
5-cyclopentyl-N'-methyl-N'-phenyl-6-(2,2,2-trifluoroethoxy)-3-pyridinecarboxylic acid hydrazide,
5-cyclohexyl-N'-methyl-N'-phenyl-6-(2,2,2-trifluoroethoxy)-3-pyridinecarboxylic acid hydrazide,
N'-(6-chloropyridazin-3-yl)-5-cyclohexyl-N'-methyl-6-(2,2,2-trifluoroethoxy)-3-pyridinecarboxylic acid hydrazide,
5-(4-chlorophenyl)-N'-(3-hydroxypropyl)-N'-methyl-6-(2,2,2-trifluoroethoxy)-3-pyridinecarboxylic acid hydrazide,
5-cyclopropyl-6-(2,2,2-trifluoro-ethoxy)-nicotinic acid N'-methyl-N'-phenyl-hydrazide,
5-cyclopropyl-6-(2,2,2-trifluoro-ethoxy)-nicotinic acid N'-(4-fluoro-phenyl)-N'-methyl-hydrazide,
5-(tetrahydro-pyran-4-yl)-6-(2,2,2-trifluoro-ethoxy)-nicotinic acid N'-methyl-N'-phenyl-hydrazide,
5-[N'-(4-fluoro-phenyl)-N'-methyl-hydrazinocarbonyl]-2-(2,2,2-trifluoro-ethoxy)-3',4',5',6'-tetrahydro-2'H-[3,4']bipyridinyl-1'-carboxylic acid tert-butyl ester,
5-cyclopropyl-6-cyclopropylmethoxy-nicotinic acid N'-(4-fluoro-phenyl)-N'-methyl-hydrazide,
5-cyclopropyl-6-cyclopropylmethoxy-nicotinic acid N'-(4-fluoro-phenyl)-N'-methyl-hydrazide,
5-cyclopropyl-6-cyclopropylmethoxy-nicotinic acid N'-methyl-N'-phenyl-hydrazide,
5-cyclopropyl-6-(2,2,2-trifluoro-ethoxy)-nicotinic acid N'-pyridin-4-ylmethyl-hydrazide,
6-cyclobutoxy-5-cyclopropyl-nicotinic acid N'-(4-fluoro-phenyl)-N'-methyl-hydrazide,
6-cyclobutoxy-5-furan-2-yl-nicotinic acid N'-(4-fluoro-phenyl)-hydrazide,
5-cyclopropyl-6-(2,2,2-trifluoro-ethoxy)-nicotinic acid N'-methyl-N'-pyridin-4-yl-hydrazide,
6-cyclobutoxy-5-furan-2-yl-nicotinic acid N'-(6-chloro-pyridazin-3-yl)-N'-methyl-hydrazide,
6-cyclobutoxy-5-furan-2-yl-nicotinic acid N'-methyl-N'-pyridin-4-yl-hydrazide,
5-cyclopropyl-6-cyclopropylmethoxy-nicotinic acid N'-(4-cyano-phenyl)-N'-methyl-hydrazide,
5-cyclopropyl-6-(2,2,2-trifluoro-ethoxy)-nicotinic acid N'-(4-cyano-phenyl)-N'-methyl-hydrazide, 6-cyclobutoxy-5-cyclopropyl-nicotinic acid N'-(4-cyano-phenyl)-N'-methyl-hydrazide,
5-(3-fluoro-phenyl)-6-(2,2,2-trifluoro-ethoxy)-nicotinic acid N'-methyl-N'-phenyl-hydrazide,
or pharmaceutically acceptable salts thereof.

Further compounds of formula I according to the invention are those, wherein
$R^4$ is hydrogen or $C_{1-7}$-alkyl, and
$R^5$ is selected from the group consisting of halogen-$C_{1-7}$-alkyl, hydroxyl-$C_{1-7}$-alkyl, $C_{1-7}$-alkoxycarbonyl, phenyl, said phenyl being unsubstituted or substituted by one, two or three groups selected from the group consisting of $C_{1-7}$-alkyl, halogen, cyano and halogen-$C_{1-7}$-alkyl, heteroaryl, said heteroaryl being unsubstituted or substituted by one or two groups selected from the group consisting of $C_{1-7}$-alkyl, halogen and halogen-$C_{1-7}$-alkyl; and heteroaryl-$C_{1-7}$-alkyl, said heteroaryl-$C_{1-7}$-alkyl being unsubstituted or substituted by one or two groups selected from the group consisting of $C_{1-7}$-alkyl, halogen and halogen-$C_{1-7}$-alkyl.

In particular, the invention relates to compounds of formula I, wherein $R^4$ is hydrogen or $C_{1-7}$-alkyl and $R^5$ is selected from the group consisting of halogen-$C_{1-7}$-alkyl, hydroxyl-$C_{1-7}$-alkyl and $C_{1-7}$-alkoxycarbonyl.

The invention also relates to compounds of formula I, wherein $R^4$ is hydrogen or $C_{1-7}$-alkyl, and $R^5$ is phenyl, said phenyl being unsubstituted or substituted by one, two or three groups selected from the group consisting of $C_{1-7}$-alkyl, halogen, cyano and halogen-$C_{1-7}$-alkyl. In particular, $R^5$ is phenyl or 4-fluorophenyl.

The invention further relates to compounds of formula I, wherein $R^4$ is hydrogen or $C_{1-7}$-alkyl, and $R^5$ is heteroaryl, said heteroaryl being unsubstituted or substituted by one or two groups selected from the group consisting of $C_{1-7}$-alkyl, halogen and halogen-$C_{1-7}$-alkyl. More particularly, $R^5$ is pyridyl or pyridazinyl, said pyridyl or pyridazinyl being unsubstituted or substituted by one or two groups selected from the group consisting of $C_{1-7}$-alkyl, halogen and halogen-$C_{1-7}$-alkyl.

The invention further relates to compounds of formula I, wherein $R^4$ is hydrogen or $C_{1-7}$-alkyl, and $R^5$ is heteroaryl-$C_{1-7}$-alkyl, said heteroaryl-$C_{1-7}$-alkyl being unsubstituted or substituted by one or two groups selected from the group consisting of $C_{1-7}$-alkyl, halogen and halogen-$C_{1-7}$-alkyl. More particularly, $R^5$ is pyridylmethyl, most particularly pyridin-4-ylmethyl.

Furthermore, the invention relates to compounds of formula I, wherein
$R^1$ is selected from the group consisting of $C_{1-7}$-alkyl, $C_{3-7}$-cycloalkyl,
$C_{3-7}$-cycloalkyl-$C_{1-7}$-alkyl,
hydroxy-$C_{1-7}$-alkyl,
$C_{1-7}$-alkoxy-$C_{1-7}$-alkyl, and
halogen-$C_{1-7}$-alkyl;
$R^2$ is phenyl, said phenyl being unsubstituted or substituted by one, two or three groups selected from the group consisting of $C_{1-7}$-alkyl, $C_{1-7}$-alkoxy, halogen, halogen-$C_{1-7}$-alkyl, halogen-$C_{1-7}$-alkoxy, amino, azido and cyano, or
$C_{3-7}$-cycloalkyl;
$R^3$ is hydrogen,
$R^4$ is hydrogen or $C_{1-7}$-alkyl,
or $R^3$ and $R^4$ are —(CH$_2$)$_3$— and together with the nitrogen atoms to which they are attached form a 5-membered heterocyclic ring;
$R^5$ is selected from the group consisting of hydrogen, halogen-$C_{1-7}$-alkyl, hydroxyl-$C_{1-7}$-alkyl, $C_{1-7}$-alkoxycarbonyl, phenyl, said phenyl being unsubstituted or substituted by one, two or three groups selected from the group consisting of $C_{1-7}$-alkyl, halogen and halogen-$C_{1-7}$-alkyl, and heteroaryl, said heteroaryl being unsubstituted or substituted by one or two groups selected from the group consisting of $C_{1-7}$-alkyl, halogen and halogen-$C_{1-7}$-alkyl;

or $R^4$ and $R^5$ together with the nitrogen atom to which they are attached form a 4-, 5-, 6- or 7-membered heterocyclic ring optionally containing a further heteroatom or group selected from nitrogen, oxygen, sulfur, sulfinyl and sulfonyl, said heterocyclic ring being unsubstituted or substituted by one, two or three groups independently selected from $C_{1-7}$-alkyl, hydroxy, hydroxy-$C_{1-7}$-alkyl, $C_{1-7}$-alkoxy, $C_{1-7}$-alkoxy-$C_{1-7}$-alkyl, heterocyclyl-$C_{1-7}$-alkyl, $C_{1-7}$-alkylcarbonyl and $C_{1-7}$-alkylsulfonyl;

or pharmaceutically acceptable salts thereof.

Particular compounds of formula I of the present invention are the following:

5-(4-chlorophenyl)-6-(2,2,2-trifluoroethoxy)-N'-(2,2,2-trifluoroethyl)-3-pyridine carboxylic acid hydrazide, 5-(4-chlorophenyl)-N-morpholino-6-(2,2,2-trifluoroethoxy)-3-pyridinecarboxamide, 5-(4-chloro-phenyl)-N-(1,1-dioxido-4-thiomorpholinyl)-6-(2,2,2-trifluoro-ethoxy)-3-pyridinecarboxamide, t-butyl 2-[(5-(4-chlorophenyl)-6-(2,2,2-trifluoroethoxy)-3-pyridinyl)carbonyl]-pyrazolidine-1-carboxylate, 5-(4-chloro-phenyl)-6-(2,2,2-trifluoro-ethoxy)-3-pyridinecarboxylic acid N'-methyl-N'-phenyl-hydrazide, 5-(4-chlorophenyl)-N-(4-hydroxypiperidin-1-yl)-6-(2,2,2-trifluoroethoxy)-3-pyridinecarboxamide, 5-(4-chlorophenyl)-N-(5-(morpholinomethyl)-2-oxooxazolidin-3-yl)-6-(2,2,2-trifluoroethoxy)-3-pyridinecarboxamide, 5-(4-chlorophenyl)-N'-(6-chloropyridazin-3-yl)-N'-methyl-6-(2,2,2-trifluoroethoxy)-3-pyridinecarboxylic acid hydrazide, 5-(4-chloro-3-fluorophenyl)-6-(2,2,2-trifluoroethoxy)-3-pyridinecarboxylic acid hydrazide, 5-(4-chlorophenyl)-6-(cyclopropylmethoxy)-N-(4-hydroxypiperidin-1-yl)-3-pyridinecarboxamide, 5-(4-chlorophenyl)-6-cyclobutoxy-N-(4-hydroxypiperidin-1-yl)-3-pyridinecarboxamide, 5-cyclohexyl-N-(4-hydroxypiperidin-1-yl)-6-(2,2,2-trifluoroethoxy)-3-pyridinecarboxamide, 5-(4-chlorophenyl)-N-(4-(methylsulfonyl)piperazin-1-yl)-6-(2,2,2-trifluoroethoxy)-3-pyridinecarboxamide, 5-cyclopentyl-N-morpholino-6-(2,2,2-trifluoroethoxy)-3-pyridinecarboxamide, 5-cyclopentyl-N-(2-oxopyrrolidin-1-yl)-6-(2,2,2-trifluoroethoxy)-3-pyridinecarboxamide, N'-(6-chloropyridazin-3-yl)-5-cyclopentyl-N'-methyl-6-(2,2,2-trifluoroethoxy)-3-pyridinecarboxylic acid hydrazide, (S)-5-cyclopentyl-N-(2-(methoxymethyl)pyrrolidin-1-yl)-6-(2,2,2-trifluoroethoxy)-3-pyridinecarboxamide, 5-cyclopentyl-N'-methyl-N'-phenyl-6-(2,2,2-trifluoroethoxy)-3-pyridinecarboxylic acid hydrazide, 5-cyclohexyl-N-morpholino-6-(2,2,2-trifluoroethoxy)-3-pyridinecarboxamide, 5-cyclohexyl-N'-methyl-N'-phenyl-6-(2,2,2-trifluoroethoxy)-3-pyridinecarboxylic acid hydrazide, 5-cyclohexyl-N-(pyrrolidin-1-yl)-6-(2,2,2-trifluoroethoxy)-3-pyridinecarboxamide, N'-(6-chloropyridazin-3-yl)-5-cyclohexyl-N'-methyl-6-(2,2,2-trifluoroethoxy)-3-pyridinecarboxylic acid hydrazide, 5-cyclohexyl-N—((S)-2-methoxymethyl-pyrrolidin-1-yl)-6-(2,2,2-trifluoroethoxy)-3-pyridinecarboxamide, 5-(4-chlorophenyl)-N-(4-(2-hydroxyethyl)piperidin-1-yl)-6-(2,2,2-trifluoroethoxy)-3-pyridinecarboxamide, 5-(4-chlorophenyl)-N-(4-(2-hydroxyethyl)piperazin-1-yl)-6-(2,2,2-trifluoroethoxy)-3-pyridinecarboxamide, 5-(4-chlorophenyl)-N-(4-(hydroxymethyl)piperidin-1-yl)-6-(2,2,2-trifluoroethoxy)-3-pyridinecarboxamide, 5-(4-chlorophenyl)-N-(4-methyl-3-oxopiperazin-1-yl)-6-(2,2,2-trifluoroethoxy)-3-pyridinecarboxamide, 5-(4-chlorophenyl)-N'-(3-hydroxypropyl)-N'-methyl-6-(2,2,2-trifluoroethoxy)-3-pyridinecarboxylic acid hydrazide, 5-(4-chlorophenyl)-N-(3-hydroxyazetidin-1-yl)-6-(2,2,2-trifluoroethoxy)-3-pyridinecarboxamide, 5-cyclopropyl-6-(2,2,2-trifluoro-ethoxy)-nicotinic acid N'-methyl-N'-phenyl-hydrazide, 5-cyclopropyl-N-(1,1-dioxo-1λ6-thiomorpholin-4-yl)-6-(2,2,2-trifluoro-ethoxy)-nicotinamide, 5-cyclopropyl-N-morpholin-4-yl-6-(2,2,2-trifluoro-ethoxy)-nicotinamide, 5-cyclopropyl-N—((S)-2-methoxymethyl-pyrrolidin-1-yl)-6-(2,2,2-trifluoro-ethoxy)-nicotinamide, 5-cyclopropyl-6-(2,2,2-trifluoro-ethoxy)-nicotinic acid N'-(4-fluoro-phenyl)-N'-methyl-hydrazide, 5-(tetrahydro-pyran-4-yl)-6-(2,2,2-trifluoro-ethoxy)-nicotinic acid N'-methyl-N'-phenyl-hydrazide, 5-(4-cyano-phenyl)-N-(4-hydroxy-piperidin-1-yl)-6-(2,2,2-trifluoro-ethoxy)-nicotinamide, 5-(4-cyano-phenyl)-N-morpholin-4-yl-6-(2,2,2-trifluoro-ethoxy)-nicotinamide, 5-(4-cyano-phenyl)-N-[4-(2-hydroxy-ethyl)-piperidin-1-yl]-6-(2,2,2-trifluoro-ethoxy)-nicotinamide, 5-[4-(2-hydroxy-ethyl)-piperidin-1-ylcarbamoyl]-2-(2,2,2-trifluoro-ethoxy)-3',4',5',6'-tetrahydro-2'H-[3,4']bipyridinyl-1'-carboxylic acid tert-butyl ester, 5-[N'-(4-fluoro-phenyl)-N'-methyl-hydrazinocarbonyl]-2-(2,2,2-trifluoro-ethoxy)-3',4',5',6'-tetrahydro-2'H-[3,4']bipyridinyl-1'-carboxylic acid tert-butyl ester, 5-cyclopropyl-6-cyclopropylmethoxy-nicotinic acid N'-(4-fluoro-phenyl)-N'-methyl-hydrazide, 5-cyclopropyl-6-cyclopropylmethoxy-nicotinic acid N'-(4-fluoro-phenyl)-N'-methyl-hydrazide, 5-cyclopropyl-6-cyclopropylmethoxy-nicotinic acid N'-methyl-N'-phenyl-hydrazide, 5-cyclopropyl-N-((2R,6S)-2,6-dimethyl-morpholin-4-yl)-6-(2,2,2-trifluoro-ethoxy)-nicotinamide, 5-cyclopropyl-6-cyclopropylmethoxy-N-((2R,6S)-2,6-dimethyl-morpholin-4-yl)-nicotinamide, 5-cyclopropyl-6-(2,2,2-trifluoro-ethoxy)-nicotinic acid N'-pyridin-4-ylmethyl-hydrazide, 6-cyclobutoxy-5-cyclopropyl-nicotinic acid N'-(4-fluoro-phenyl)-N'-methyl-hydrazide, 6-cyclobutoxy-5-furan-2-yl-nicotinic acid N'-(4-fluoro-phenyl)-hydrazide, 5-cyclopropyl-6-(2,2,2-trifluoro-ethoxy)-nicotinic acid N'-methyl-N'-pyridin-4-yl-hydrazide, 6-cyclobutoxy-5-furan-2-yl-N-(4-hydroxy-piperidin-1-yl)-nicotinamide, 6-cyclobutoxy-5-furan-2-yl-nicotinic acid N'-(6-chloro-pyridazin-3-yl)-N'-methyl-hydrazide, 6-cyclobutoxy-5-furan-2-yl-nicotinic acid N'-methyl-N'-pyridin-4-yl-hydrazide, 5-cyclopropyl-6-cyclopropylmethoxy-nicotinic acid N'-(4-cyano-phenyl)-N'-methyl-hydrazide, 5-cyclopropyl-6-(2,2,2-trifluoro-ethoxy)-nicotinic acid N'-(4-cyano-phenyl)-N'-methyl-hydrazide, 6-cyclobutoxy-5-cyclopropyl-nicotinic acid N'-(4-cyano-phenyl)-N'-methyl-hydrazide, 5-(3-fluoro-phenyl)-6-(2,2,2-trifluoro-ethoxy)-nicotinic acid N'-methyl-N'-phenyl-hydrazide, or pharmaceutically acceptable salts thereof.

Of particular interest are furthermore the following compounds:

5-cyclopropyl-N—((S)-2-methoxymethyl-pyrrolidin-1-yl)-6-(2,2,2-trifluoro-ethoxy)-nicotinamide,
5-cyclopropyl-6-(2,2,2-trifluoro-ethoxy)-nicotinic acid N'-(4-fluoro-phenyl)-N'-methyl-hydrazide,
5-[N'-(4-fluoro-phenyl)-N'-methyl-hydrazinocarbonyl]-2-(2,2,2-trifluoro-ethoxy)-3',4',5',6'-tetrahydro-2'H-[3,4']bipyridinyl-1'-carboxylic acid tert-butyl ester,
5-cyclopropyl-6-cyclopropylmethoxy-nicotinic acid N'-(4-fluoro-phenyl)-N'-methyl-hydrazide,
5-cyclopropyl-6-(2,2,2-trifluoro-ethoxy)-nicotinic acid N'-pyridin-4-ylmethyl-hydrazide,
6-cyclobutoxy-5-cyclopropyl-nicotinic acid N'-(4-fluorophenyl)-N'-methyl-hydrazide,
5-(3-fluoro-phenyl)-6-(2,2,2-trifluoro-ethoxy)-nicotinic acid N'-methyl-N'-phenyl-hydrazide, or pharmaceutically acceptable salts thereof.

More particularly, compounds of formula I of the present invention are the following:

5-(4-chlorophenyl)-N-(4-hydroxypiperidin-1-yl)-6-(2,2,2-trifluoroethoxy)-3-pyridinecarboxamide,
5-(4-chlorophenyl)-6-cyclobutoxy-N-(4-hydroxypiperidin-1-yl)-3-pyridinecarboxamide,
5-cyclohexyl-N-(4-hydroxypiperidin-1-yl)-6-(2,2,2-trifluoroethoxy)-3-pyridinecarboxamide,
5-(4-chlorophenyl)-N-(4-(2-hydroxyethyl)piperazin-1-yl)-6-(2,2,2-trifluoroethoxy)-3-pyridinecarboxamide, or pharmaceutically acceptable salts thereof.

The compounds of formula I can be prepared by a process, which process comprises a) coupling a compound of formula

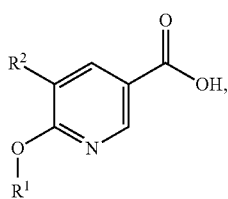

II wherein $R^1$ and $R^2$ are as defined herein before, with a hydrazine of the formula

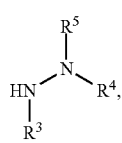

III wherein $R^3$, $R^4$ and $R^5$ are as defined herein before, in the presence of a coupling agent under basic conditions, and, if desired, converting the resulting compound of formula I into a pharmaceutically acceptable salt thereof; or, alternatively, b) reacting a compound of formula

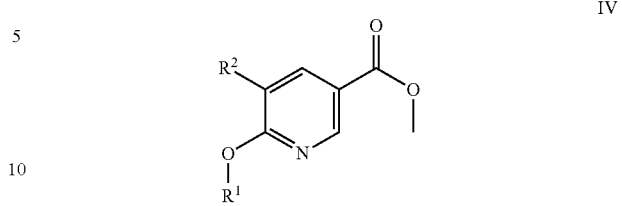

IV wherein $R^1$ and $R^2$ are as defined herein before, with a hydrazine of the formula

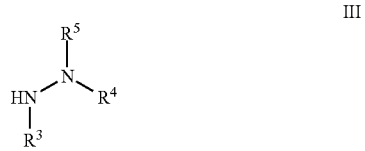

III wherein $R^3$, $R^4$ and $R^5$ are as defined herein before, by thermal condensation methods, and, if desired, converting the resulting compound of formula I into a pharmaceutically acceptable salt thereof.

Hydrazines of formula III may contain functional groups that would interfere with the coupling procedures described for the coupling step (II to I). In this case it is understood that hydrazines III need to be suitably protected by methods known in the art before conducting the coupling procedure and compounds need to be deprotected after the coupling step by methods known in the art to deliver compounds of formula I.

Coupling agents for the reaction of compounds of formula II with hydrazines of formula III are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), or O-benzotriazol-1-yl-N,N,N',N'-tetramethyluronium tetrafluoroborate (TBTU). In particular, the coupling agent is TBTU. Suitable bases include triethylamine, diisopropylethylamine and, particularly, Hünig's base.

Alternative methods known in the art may commence by preparing the acid chloride from II and coupling with a hydrazine of formula III in the presence of a suitable base.

Thermal condensation methods are condensation methods known in the art, for example heating both components IV and III in an inert solvent to reflux temperature. In particular, the inert solvent is ethanol.

Following the procedure according to scheme 1, compound AA (5-bromo-6-chloro-3-pyridinecarboxylic acid, CAN 29241-62-1) can be used as starting material. AA is commercially available or can alternatively be prepared by a multi-step sequence from 6-hydroxy-3-pyridinecarboxylic acid following literature procedures.

Compound AB can be prepared from AA by reaction with a suitably substituted primary or secondary alcohol $R^1$—OH (AC) in the presence of a base, for example potassium hydroxide, in an inert solvent, for example dimethylsulfoxide, at temperatures from room temperature to reflux temperature of the solvent, particularly at room temperature.

Compound II-a can be prepared from AB by coupling a suitably substituted aryl metal species of formula AD, preferably an arylboronic acid, a potassium aryl trifluoroborate, or an arylboronic acid ester, with AB in the presence of a suitable catalyst, preferably a palladium catalyst and more preferably palladium(II)chloride-dppf (1,1'-bis(diphenylphosphino)ferrocene) complexes or palladium(II) acetate in the presence of a suitable ligand like butyldi-1-adamantylphosphine and a base, preferably potassium carbonate or cesium carbonate in an inert solvent such as dimethylformamide, toluene, water, dioxane, or a mixture thereof.

(HATU), 1-hydroxy-1,2,3-benzotriazole (HOBT), and O-benzotriazol-1-yl-N,N,N',N'-tetramethyluronium tetrafluoroborate (TBTU) can be employed to affect such transformations. A convenient method is to use for example TBTU and a base, for example Hünig's base (N-ethyldiisopropylamine) in an inert solvent such as for example dimethylformamide at room temperature.

Following the procedure according to scheme 2, compounds AB can be used as starting material.

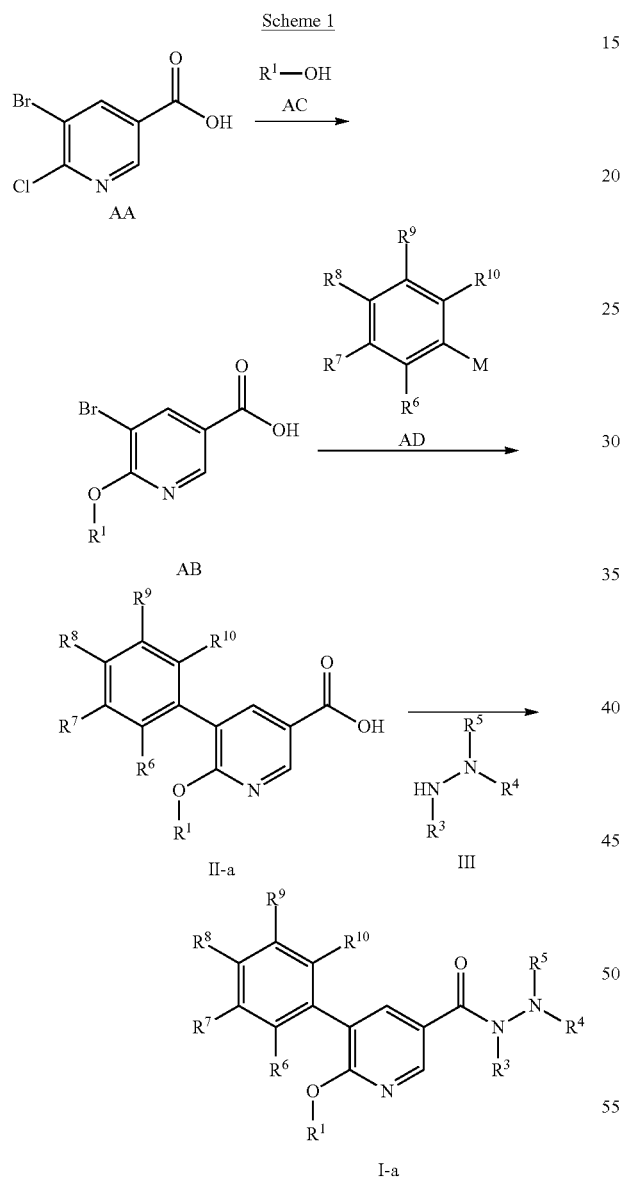

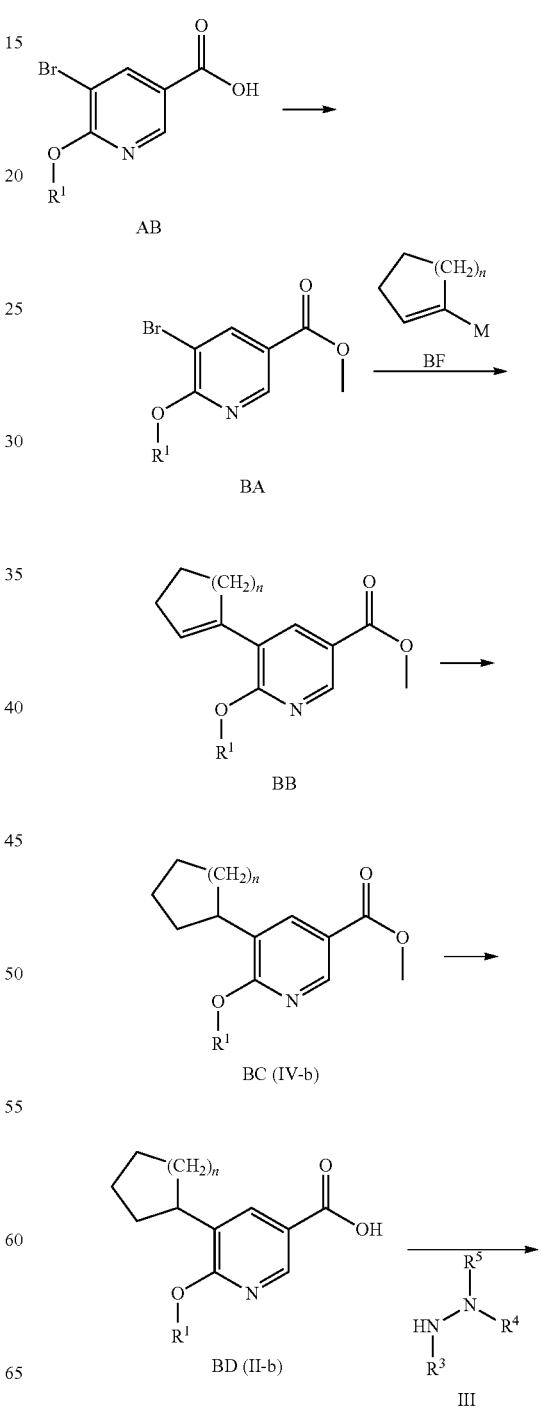

Compound I-a can be prepared from II-a and the corresponding hydrazine of formula III by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate

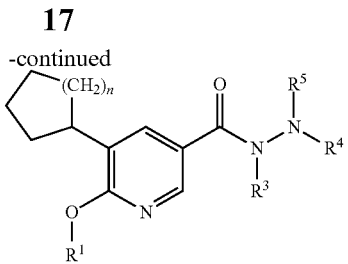

I-b

Compound BA can be obtained by a host of carboxylic ester formation methods known in the art from compound AB, for example by formation of the carboxylic acid chloride with thionyl chloride in the presence of catalytic amounts of DMF at elevated temperatures, followed by methanolysis of the acid chloride at temperatures form 0° C. to reflux temperature.

Compound BB can be prepared from BA by coupling a suitably substituted cycloalkenyl metal species of formula BF, wherein n is selected from the group consisting of 0, 1, 2 and 3, particularly a cycloalkenylboronic acid ester, with BA in the presence of a suitable catalyst, in particular a palladium catalyst and more particularly palladium(II)chloride-dppf (1,1'-bis(diphenylphosphino)ferrocene) complexes and a base, particularly potassium carbonate in an inert solvent such as dimethylformamide.

Compound BC (IV-b) can be obtained by hydrogenation of compound BB by methods known in the art, for example by hydrogenation with hydrogen gas in the presence of a palladium catalyst, for example palladium on charcoal, in an inert solvent, for example ethanol, at suitable temperatures and pressures, particularly at ambient temperature and pressure.

Compound BD (II-b) can be obtained by saponification of compound BC by methods known in the art, for example by saponification with an alkalimetal hydroxide, for example lithium hydroxide, in a suitable solvent, for example a mixture of THF and water.

Compound I-b (a compound of formula I, wherein $R^2$ is cycloalkyl) can be prepared from II-b and the corresponding hydrazine of formula III by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), and O-benzotriazol-1-yl-N,N,N',N'-tetramethyluronium tetrafluoroborate (TBTU) can be employed to affect such transformations. A convenient method is to use for example TBTU and a base, for example Hünig's base (N-ethyldiisopropylamine) in an inert solvent such as for example dimethylformamide at room temperature.

Hydrazines of formula III-a that are not commercially available may be prepared by methods known in the art, particularly by the two step process depicted in scheme 3, that starts from amines of formula CA.

Compounds of formula CB can be obtained by reacting compounds of formula CA with an 3-aryl-2-oxaziridinecarboxylic acid ester, preferably 3-(4-cyanophenyl)-2-oxaziridinecarboxylic acid 1,1-dimethylethyl ester, in the presence of a base, preferably diisopropylethylamine, at low temperature, preferably at 0° C., in an inert solvent, preferably dichloromethane (scheme 3, top). Acidic removal of the carbamate protecting group, preferably with a mixture of dichloromethane and trifluoroacetic acid at 0° C., delivers then hydrazines of formula III-a.

Alternatively, they can be obtained by amination with chloramine generated in situ from aq. ammonia with sodium hypochlorite in the presence of ammonium chloride and sodium hydroxide (scheme 3, bottom).

Scheme 3

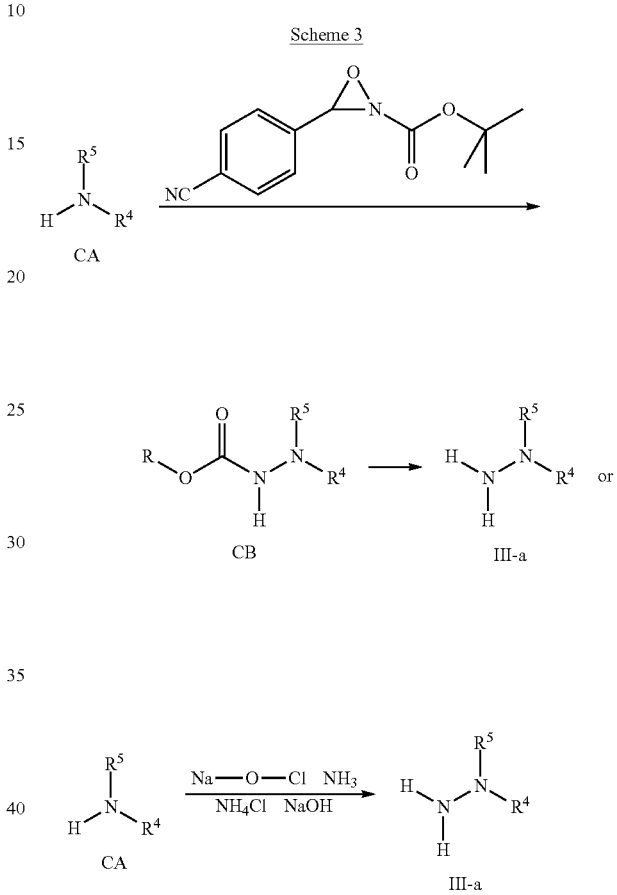

Amines of formula CA may contain functional groups that would interfere with the procedure described in scheme 3. In this case it is understood that amines CA need to be suitably protected by methods known in the art before conducting the above procedure and need to be deprotected by methods known in the art to deliver hydrazines of formula III-a.

Alternatively the compounds of formula I can be prepared by a process, which process comprises reacting a compound of formula

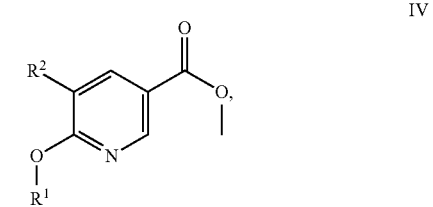

IV wherein $R^1$ an $R^2$ are as defined herein before, with a hydrazine of the formula

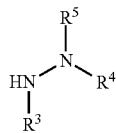

wherein $R^3$, $R^4$ and $R^5$ are as defined herein before, by thermal condensation methods known in the art, for example by heating both components in an inert solvent to reflux temperature, and, if desired, converting the resulting compound of formula I into a pharmaceutically acceptable salt thereof.

Hydrazines of formula III may contain functional groups that would interfere with the condensation procedures described for the coupling step (IV to I). In this case it is understood that hydrazines III need to be suitably protected by methods known in the art before conducting the condensation procedure and need to be deprotected after the condensation step by methods known in the art to deliver compounds of formula I.

Following the procedure according to scheme 4, compound AB can be used as starting material.

Scheme 4

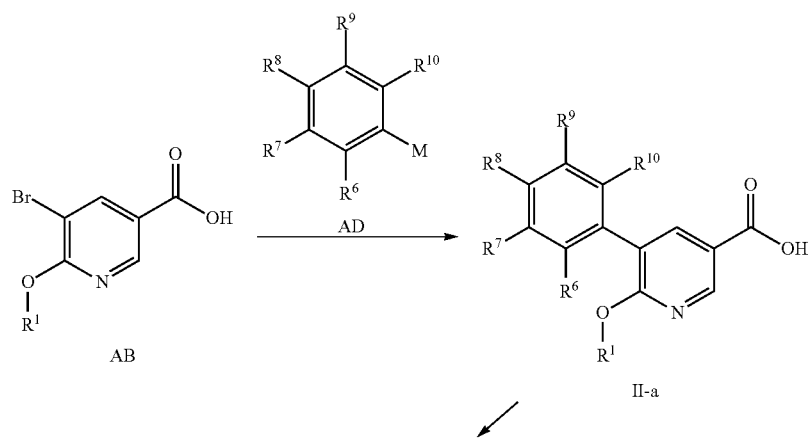

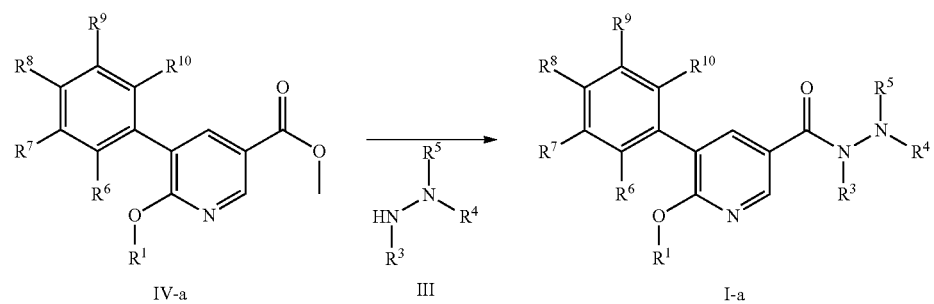

Compound II-a can be prepared from AB by coupling a suitably substituted aryl metal species of formula AD, preferably an arylboronic acid or arylboronic acid ester, with AB in the presence of a suitable catalyst, preferably a palladium catalyst and more preferably palladium(II)chloride-dppf (1,1'-bis(diphenylphosphino)ferrocene) complexes and a base, preferably potassium carbonate in an inert solvent such as dimethylformamide.

Compound IV-a can be obtained by a host of carboxylic ester formation methods known in the art from compound II-a, for example by formation of the carboxylic acid chloride with thionyl chloride in the presence of catalytic amounts of DMF at elevated temperatures, followed by methanolysis of the acid chloride at temperatures form 0° C. to reflux temperature.

Compound I-a can be prepared from IV-a and the corresponding hydrazine of formula III by thermal condensation methods known in the art, particularly by heating both components in an inert solvent, particularly ethanol to reflux temperature.

Following the procedure according to scheme 5, compound BC (IV-b), wherein n is 0, 1, 2, 3 or 4, can be used as starting material.

Scheme 5

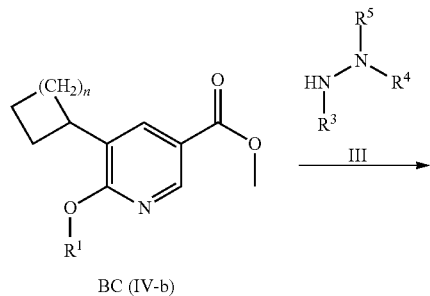

BC (IV-b)

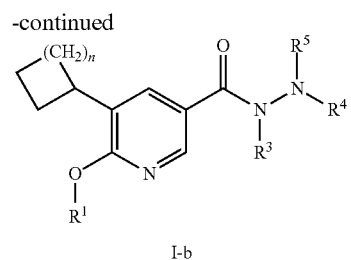

I-b

Compound I-b can be prepared from IV-b and the corresponding hydrazine of formula III by thermal condensation methods known in the art, particularly by heating both components in an inert solvent, particularly ethanol to reflux temperature.

Compound BB can alternatively be prepared from BA by Negishi coupling of a suitably substituted cycloalkyl- or heterocycloalkyl iodide of formula BF in the presence of a suitable catalyst, preferably a palladium catalyst and more preferably palladium(II)chloride-dppf (1,1'-bis(diphenylphosphino)ferrocene) complex, zinc metal, copper iodide, trimethylchlorosilane, and 1,2-dibromoethane, in an inert solvent such as dimethylacetamide.

Compound BC (II-b) can be obtained by saponification of compound BB by methods known in the art, for example by saponification with an alkalimetal hydroxide, for example lithium hydroxide, in a suitable solvent, for example a mixture of THF and water. Coupling as detailed above with the appropriate hydrazine III then delivers the target compound I-b (scheme 6).

Scheme 6

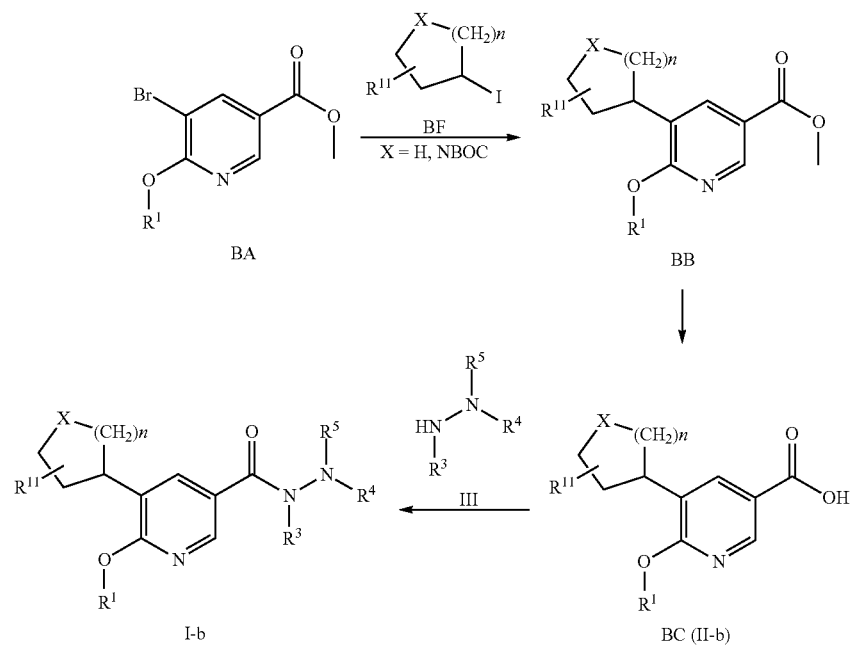

Compounds I-a substituted with a cyclopropyl group in meta position are preferably synthesized according to scheme 7.

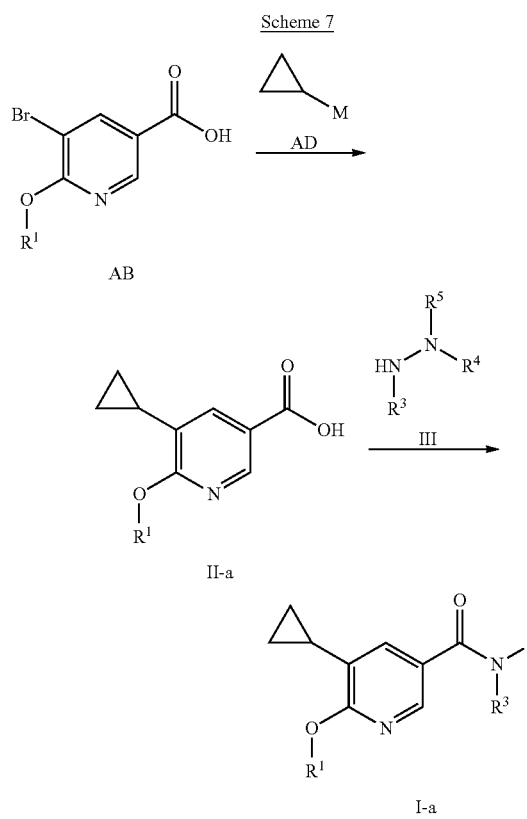

Compounds I-a substituted with a cyclopropyl group in meta position are preferably synthesized according to scheme 7. Potassium cyclopropyl trifluoroborate, or cyclopropylboronic acid or a corresponding boronic acid ester AD, is reacted with AB in the presence of a suitable catalyst, preferably a palladium catalyst and more preferably palladium (II)chloride-dppf (1,1'-bis(diphenylphosphino)ferrocene) complex or palladium(II) acetate in the presence of a suitable ligand like butyldi-1-adamantylphosphine and a base, preferably potassium carbonate or cesium carbonate in an inert solvent such as dimethylformamide, toluene, water, dioxane, or a mixture thereof to provide intermediate II-a. Transformation to the final product I-a proceeds in perfect analogy to the methods described above. Sometimes, it is advantageous to do the Suzuki coupling at the stage of the methyl ester and not the free acid.

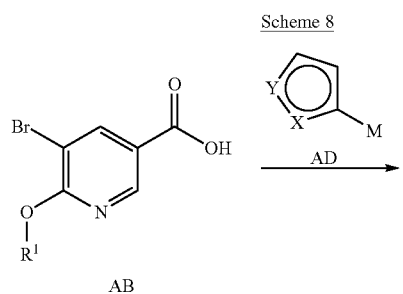

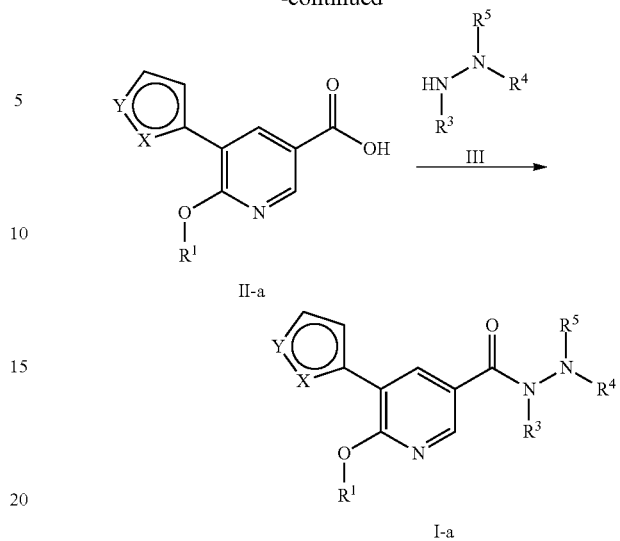

Compounds I-a substituted with a furyl group in meta position are preferably synthesized according to scheme 8. A furylboronic acid AD (wherein one of X or Y is O), the corresponding potassium trifluoroborate, or an appropriate boronic acid ester, are coupled with AB in the presence of a suitable catalyst, preferably a palladium catalyst and more preferably palladium(II)chloride-dppf (1,1'-bis(diphenylphosphino)ferrocene) complexes or palladium(II) acetate in the presence of a suitable ligand like butyldi-1-adamantylphosphine and a base, preferably potassium carbonate or cesium carbonate in an inert solvent such as dimethylformamide, toluene, water, dioxane, or a mixture thereof. Transformation to the final product I-a is then performed again in perfect analogy to the methods described above. Sometimes, it is advantageous to do the Suzuki coupling at the stage of the methyl ester and not the free acid.

As described above, the compounds of formula I of the present invention can be used as medicaments for the treatment and/or prophylaxis of diseases which can be treated with HDL-cholesterol raising agents. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, improvement of glycemic control, obesity or endotoxemia. The use as medicament for the treatment and/or prevention of dyslipidemia, atherosclerosis and cardiovascular diseases is of particular interest.

The invention therefore also relates to pharmaceutical compositions comprising a compound of formula I as defined above and a pharmaceutically acceptable carrier and/or adjuvant. The pharmaceutical compositions are useful in the treatment and/or prophylaxis of diseases which can be treated with HDL-cholesterol raising agents.

Thus, the invention relates to a pharmaceutical composition as defined above for use in the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, improvement of glycemic control, obesity or endotoxemia.

In another embodiment, the invention relates to a method for the treatment and/or prophylaxis of diseases which can be treated with HDL-cholesterol raising agents, which method comprises administering a therapeutically effective amount of a compound of formula I to a patient in need thereof. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, improvement of glycemic control, obesity or endotoxemia. A method for the treatment and/or prophylaxis of dyslipidemia, atherosclerosis and cardiovascular diseases is preferred.

The invention also relates to the compounds of formula I for use as medicaments. More specifically, the invention relates to compounds of formula I for use as HDL-cholesterol raising agents. Thus, the invention is concerned with compounds of formula I for use in the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, improvement of glycemic control, obesity or endotoxemia, in particular for use in the treatment and/or prophylaxis of dyslipidemia, atherosclerosis and cardiovascular diseases.

In addition, the invention relates to the use of compounds of formula I as defined above for the preparation of a medicament for the treatment and/or prophylaxis of diseases can be treated with HDL raising agents. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, improvement of glycemic control, obesity or endotoxemia. The use of compounds of formula I as defined above for the preparation of medicaments for the treatment and/or prophylaxis of dyslipidemia, atherosclerosis and cardiovascular diseases is of particular interest.

In addition, HDL raising agents of formula I are useful in combination or association with another compound, said compound being selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

The invention therefore also relates to pharmaceutical compositions comprising a compound of formula I as defined above in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant, as well as a pharmaceutically acceptable carrier and/or adjuvant.

The invention further relates to compounds of formula I as defined above in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant for use in the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, improvement of glycemic control, obesity or endotoxemia.

The invention also relates to a method for the treatment and/or prophylaxis of diseases which can be treated with HDL-cholesterol raising agents, which method comprises administration of a therapeutically effective amount of a compound according to formula I in combination or association with a therapeutically effective amount of a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

Pharmacological Tests

The following tests were carried out in order to determine the activity of the compounds of formula I and their valuable pharmacological properties.

Detection of Upregulation of ABCA1 Protein in Cells

The ability of compounds of the invention to increase the level of ABCA1 protein is determined in replicate cultures of THP-1 macrophage cells in 96-well microplates. Cells are plated at an initial density of 100,000 cells/well in 100 µl medium and differentiated to adherent macrophages with the addition of PMA (100 nM) for 68 hrs in 10% fetal bovine serum, 3 µl/L of b-mercaptoethanol, RPMI-1640 medium. Then, cells are incubated with RPMI-1640 medium containing 1% FCS, 25 µg/ml acetylated LDL, for 24 hours at 37° C. Following incubation with acetylated LDL, cells are washed twice with 50 µl PBS and incubated with 100 µl of RPMI-1640 medium containing the compound of interest solubilized in DMSO for an additional 24 hrs. The final DMSO concentration in presence of cells is maintained at 0.5%. ApoA-I binding assay using High Content Image Analysis is initiated by replacing with fresh medium, RPMI without Phenol Red, 0.2% BSA containing AlexaFluor®647 labeled ApoA-I for 2 h/37° C./5% CO2. Then, cells are fixed with 4% Formaldehyde in PBS (15 min, RT). Following Nuclei are stained with Hoechst solution (3 µM PBS) and Cytoplasm with Cell Mask Blue (2 µg/ml PBS), 15 min, RT. Finally the stained cells are fixed with a second round of formaldehyde treatment. Fixed stained cells are washed and kept in PBS at 4° C. and can be read immediately until one month after preparation. That the binding of ApoA-I indeed reflected the level of ABCA1 in the cell, was demonstrated by loss of signal when ABCA1 expression was artificially reduced by transfection with small interfering RNA's.

The Alexa Fluor 647-labeled Apolipoprotein A-I (20 nM) was prepared as follows: Human recombinant Apolipoprotein A-I (ApoA-I) was exchanged to a buffer of 0.02 M $NaHCO_3$ at pH 8.2 on an NAP desalting column (GE Healthcare) and brought to a concentration to 40 µM (1.13 mg/ml) by adjustment with the same buffer. The ApoA-I was fluorescently labeled by incubation with Alexa Fluor carboxylic acid succimidyl ester (Alexa Fluor 647, Invitrogen A-20006) at a 2:1 molar ratio (Alexa to ApoA-I) for 1 h under shaking at RT. The remaining unconjugated label was removed by buffer exchange to 0.02M $NaHCO_3$ at pH 8.2.

Imaging and data collection were performed on an OPERA confocal microplate imaging reader using a 20× water immersion objective and UV360 or 405 laser to identify the cell nuclei and a 635 laser to identify the fluorescent ApoA-I. Eight fields of view are captured per well. Image capture and analysis was performed with the Acapella software. Background fluorescence detected in control wells without ApoA-I was subtracted.

Using XLfit3 program (ID Business Solutions Ltd. UK), the model 205 for Dose Response One Site is used to calculate the $EC_{50}$ values. The compounds of the present invention exhibit $EC_{50}$ values in a range of 0.1 µM to 10 µM in the ABCA1 protein detection assay. More particularly, the compounds of the present invention have $EC_{50}$ values in a range of 0.1 µM to 3 µm.

TABLE 1

| ABCA1 protein increasing efficacy | | |
|---|---|---|
| Example | % increase of ABCA1 at 3 µM | $EC_{50}$ [µM] |
| 1 | >45%@ 3 µM | |
| 2 | >45%@ 3 µM | |
| 3 | >45%@ 3 µM | |
| 4 | >45%@ 3 µM | |
| 5 | >45%@ 3 µM | |
| 6 | | 1.11 |
| 7 | >45%@ 3 µM | |
| 8 | >45%@ 3 µM | |
| 9 | >45%@ 3 µM | |
| 10 | | 1.03 |
| 11 | | 0.18 |
| 12 | | 1.48 |
| 13 | | 0.33 |
| 14 | | 1.08 |
| 15 | >45%@ 3 µM | |
| 16 | | 1.17 |
| 17 | | 0.12 |
| 18 | >45%@ 3 µM | |
| 19 | | 5.39 |
| 20 | >45%@ 3 µM | |
| 21 | >45%@ 3 µM | |
| 22 | | 0.98 |
| 23 | >45%@ 3 µM | |
| 24 | >45%@ 3 µM | |
| 25 | >45%@ 3 µM | |
| 26 | >45%@ 3 µM | |
| 27 | | 2.39 |
| 28 | >45%@ 3 µM | |
| 29 | >45%@ 3 µM | |
| 30 | >45%@ 3 µM | |
| 31 | >45%@ 3 µM | |
| 32 | | 1.77 |
| 33 | | 0.68 |
| 34 | | 0.83 |
| 35 | | 2.35 |
| 36 | | 1.86 |
| 37 | | 1.32 |
| 38 | | 0.15 |
| 39 | | 1.8 |
| 40 | | 0.68 |
| 41 | | 1.1 |
| 42 | | 3.2 |
| 43 | | 1.04 |
| 44 | >45%@ 3 µM | |
| 45 | | 9.4 |
| 46 | >45%@ 3 µM | |
| 47 | >45%@ 3 µM | |
| 48 | | 0.8 |
| 49 | >45%@ 3 µM | |
| 50 | | 0.16 |
| 51 | | 0.47 |
| 52 | | 5.8 |
| 53 | >45%@ 3 µM | |
| 54 | >45%@ 3 µM | |
| 55 | >45%@ 3 µM | |
| 56 | >45%@ 3 µM | |

Cholesterol Efflux Assay

The ability of compounds of the invention to stimulate cholesterol efflux is determined in replicate cultures of THP-1 cells in 96-well microplates. Cells are plated at an initial density of 150,000 cells/well and differentiated to macrophages with the addition of PMA (100 ng/ml) for 72 hrs in 10% fetal bovine serum, 3 µl/L of b-mercaptoethanol, RPMI-1640 medium. Cells are washed once with RPMI-1640 and loaded with RPMI-1640 medium containing 2% FCS, 50 µg/ml acetylated LDL, and 10 µCi/ml [$^3$H]cholesterol for 48 hours at 37° C. After loading the cells are washed once with RPMI-1640 and incubated with the compound of interest from DMSO solutions for an additional 24 hrs in RPMI-1640 medium containing 1 mg/ml fatty acid free-bovine serum albumin (BSA). Upon incubation cells are washed once, and cholesterol efflux is induced by the addition of 10 µg/ml Apolipoprotein AI in RPMI-1640 containing 1 mg/ml BSA and in the presence of the compound for an additional 6 hrs. Following incubation radioactivity is determined in the supernatants and cholesterol efflux is expressed as the percent stimulation over replicate cultures treated only with DMSO. Sigmoidal curves were fitted using the XLfit3 program (ID Business Solutions Ltd. UK) and $EC_{50}$ values were determined.

The compounds of the present invention exhibit $EC_{50}$ values in a range of 0.1 µM to 3.0 µM in the cholesterol efflux assay. Particularly, the compounds of the present invention have $EC_{50}$ values in a range of 0.1 µM to 1.5 µM.

CB1 and CB2 Receptor Affinity

The affinity of the compounds of the invention for cannabinoid receptors was determined using membrane preparations of human embryonic kidney (HEK) cells in which the human CB1 receptor is transiently transfected using a Semliki Forest Virus system in conjunction with [3H]-CP-55,940 as radioligand. After incubation of freshly prepared cell membrane preparation with the [$^3$H]-ligand, with or without addition of compounds of the invention, separation of bound and free ligand was performed by filtration over glass fiber filters. Radioactivity on the filter was measured by scintillation counting.

The affinity of the compounds of the invention for cannabinoid CB2 receptors was determined using membrane preparations of human embryonic kidney (HEK) cells in which the human CB2 receptor is transiently transfected using a Semliki Forest Virus system in conjunction with [$^3$H]-CP-55,940 as radioligand. After incubation of freshly prepared cell membrane preparation with the [$^3$H]-ligand, with or without addition of compounds of the invention, separation of bound and free ligand was performed by filtration over glass fiber filters. Radioactivity on the filter was measured by scintillation counting.

The ability of the compounds to displace the radioligand [$^3$H]-CP-55,940 was measured at a concentration of 10 μM and values provided as [% inhibition @ 10 μM] both for the CB1 and CB2 receptor assay, The lower % inhibition is, the lower the likelihood of side effects based on CB1 or CB2 receptor inhibition is.

The compounds of the present invention exhibit values below 50% inhibition in both the CB1 and CB2 receptor assay at a concentration of 10 μM. Particularly, the compounds of the present invention exhibit values below 35% inhibition in both the CB1 and CB2 receptor assays and even more particularly below 20% in both assays.

TABLE 2

CB1 and CB2-receptor affinity

| Example | CB1 receptor affinity [% inhibition @ 10 μM] | CB2 receptor affinity [% inhibition @ 10 μM] |
|---|---|---|
| 1 | 42 | 10 |
| 2 | 43 | 8 |
| 3 | 39 | 7 |
| 4 | 40 | 24 |
| 5 | 45 | 31 |
| 6 | 11 | -9 |
| 7 | 36 | -4 |
| 8 | 38 | 18 |
| 9 | 11 | -2 |
| 10 | 34 | 2 |
| 11 | 14 | -8 |
| 12 | 8 | 6 |
| 13 | 23 | 1 |
| 14 | 19 | 9 |
| 15 | 13 | 12 |
| 16 | 21 | -5 |
| 17 | 33 | 3 |
| 18 | 41 | 18 |
| 19 | 29 | -23 |
| 20 | 39 | 9 |
| 21 | 39 | -17 |
| 22 | 28 | -9 |
| 23 | 39 | 17 |
| 24 | 45 | -8 |
| 25 | 14 | -18 |
| 26 | 37 | -17 |
| 27 | 25 | -11 |
| 28 | 46 | -9 |
| 29 | 44 | -10 |
| 30 | 24 | 13 |
| 31 | -2 | -14 |
| 32 | 14 | -14 |
| 33 | 21 | 3 |
| 34 | 15 | 8 |
| 35 | 34 | 25 |
| 36 | 10 | -4 |
| 37 | 47 | -8 |
| 38 | 37 | -6 |
| 39 | -3 | -5 |
| 40 | 50 | 3 |
| 41 | 29 | 38 |
| 42 | 11 | 9 |
| 43 | 28 | 39 |
| 44 | 14 | 5 |
| 45 | 19 | 17 |
| 46 | 11 | 11 |
| 47 | 25 | 7 |
| 48 | 43 | -2 |
| 49 | 13 | 3 |
| 50 | 15 | 6 |
| 51 | 30 | -4 |
| 52 | 31 | 19 |
| 53 | 47 | 48 |
| 54 | 36 | 17 |
| 55 | 27 | 18 |
| 56 | 28 | 16 |

Further demonstration of biological activities of the compounds of the present invention may be accomplished through the following in vivo assays that are well known in the art.

Effects on Plasma Lipid Levels in Lean, Chow Fed Rats

The effects of compounds of compounds of formula I on plasma lipid levels were determined in lean, chow-fed Sprague-Dawley rats with compounds administered by p.o. gavage. After one week of acclimatization, blood samples were collected from 4 hour-fasted animals for plasma lipid determination. Animals were then assigned to treatment groups based on HDL-cholesterol levels. Compounds of formula I were administered by gavage, once daily for five days. Control animals received vehicle alone. Blood was collected on day five from 4 hour-fasted rats, 2 hours after a final treatment, for plasma lipid analysis. Total cholesterol, HDL-cholesterol, and triglycerides were determined by measuring total cholesterol, HDL-cholesterol, and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Obese, High Fat Diet Fed Rats

Efficacy of compounds in modulating plasma lipid levels was determined also in obese male Sprague Dawley rats after 28-29 days administration of compounds. Male Sprague-Dawley rats of 10 weeks of age were fed a high fat diet during 3 weeks. Obese rats were distributed in groups according to homogeneous BW and FI evaluated a week before the start of the treatment. Treatment was administered as food-Admix. On day 29, blood was taken in the morning under slight anesthesia (retro-orbital method) in post-prandial conditions i.e. 4 h after food was removed. Plasma was separated from blood by low speed centrifugation and selected organs were taken (e.g. liver, fat). Total cholesterol, HDL-cholesterol, and triglycerides were determined by measuring total cholesterol, HDL-cholesterol, LDL-cholesterol and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Hamsters

Efficacy of compounds in modulating plasma lipid levels was determined in hamsters after 5 days of daily administration of compounds. Male hamsters of 6-8 weeks of age were used in the studies. After one week of acclimation, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using colorimetric enzymatic assays (Roche Diagnostic GmbH, Mannheim, Germany). HDL-cholesterol, LDL-cholesterol, and VLDL-cholesterol levels were also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Cholesterol/Fat Fed Hamsters

Efficacy of compounds in modulating plasma lipid levels was determined in hamsters after 5 days of daily administration of compounds. Male hamsters of 6-8 weeks of age were used in the studies. After one week of acclimatization, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using colorimetric enzymatic assays (Roche Diagnostic GmbH, Mannheim, Germany). HDL-cholesterol was also determined after selective precipitation of HDL from plasma by standard procedures.

Pharmaceutical Compositions

The compounds of formula I and/or their pharmaceutically acceptable salts can be used in the form of pharmaceutical compositions for enteral, parenteral or topical administration. They can be administered, for example, perorally, e.g. in the form of tablets, coated tablets, dragées, hard and soft gelatin capsules, solutions, emulsions or suspensions, orally, e.g. in the form of buccal cavities, rectally, e.g. in the form of suppositories, parenterally, e.g. in the form of injection solutions or infusion solutions for intramuscular, intravenous or subcutaneous injection, or topically, e.g. in the form of ointments, creams or oils. Oral administration is of particular interest.

The production of the pharmaceutical compositions can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatin capsules. Suitable carrier materials for soft gelatin capsules are, for example, vegetable oils, waxes, fats and semi-solid and liquid polyols (depending on the nature of the active ingredient no carriers might, however, be required in the case of soft gelatin capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The therapeutically effective amount or dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 100 mg, especially about 1 to 50 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 1-100 mg, particularly 5-50 mg, of a compound of formula I.

The following examples C1 to C3 illustrate typical compositions of the present invention, but serve merely as representative thereof.

Example C1

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example C2

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C3

Injection solutions can have the following composition:

| Compound of formula (I) | 3.0 mg |
| --- | --- |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

EXAMPLES

MS=mass spectrometry; EI=electron ionization; ESI=electrospray; NMR data are reported in parts per million (δ) relative to internal tetramethylsilane and are referenced to the deuterium lock signal from the sample solvent (d$_6$-DMSO unless otherwise stated); coupling constants (J) are in Hertz, mp=melting point; bp=boiling point; HPLC=LC=high performance liquid chromatography, Rt=retention time, TLC=thin layer chromatography, TBTU=O-(benzotriazol-1-yl)-N,N,N',N'-tetramethyl-uronium-tetrafluoroborate; TEMPO=2,2,6,6-tetra-methylpiperidine 1-oxyl radical, DMF=dimethylformamide, DIPEA=N,N-diisopropylethylamine, DMSO=dimethyl-sulfoxide, DMA=Dimethylacetamide, TBME=tert. Butyl methyl ether, THF=tetrahydrofuran, CAN=CAS Registry Number.

Example 1

Preparation of 5-(4-chlorophenyl)-6-(2,2,2-trifluoroethoxy)-N'-(2,2,2-trifluoroethyl)-3-pyridinecarboxylic acid hydrazide

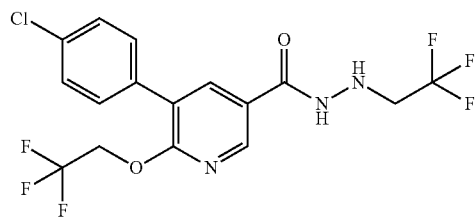 [SMILES: O=C(NNCC(F)(F)F)c1cnc(OCC(F)(F)F)c(-c2ccc(Cl)cc2)c1]

5-(4-Chlorophenyl)-6-(2,2,2-trifluoroethoxy)-3-pyridinecarboxylic acid (1000 mg, 3.02 mmol; CAN 1018782-82-5) and (2,2,2-trifluoroethyl)hydrazine (380 mg, 3.33 mmol; CAN 5042-30-8) were combined with DMF (10 mL) to give a colorless solution. TBTU (1.06 g, 3.32 mmol) and DIPEA (1.56 g, 2.05 mL, 12.1 mmol) were added. The reaction mixture was stirred for 15 h at room temperature. The reaction mixture was poured into water (50 mL) and extracted with ethyl acetate (2×50 mL). The organic layers were combined and washed with water (1×50 mL) and brine (1×50 mL). The organic layers were dried with MgSO$_4$ and concentrated in vacuo. The residue was purified by flash chromatography (silica gel, 50 g, 0% to 50% EtOAc in hexane) to give the title compound (0.35 g, 27%) as white solid; LC-MS (UV peak area/ESI) 100%, 426.0451 (M−H)$^-$.

Example 2

Preparation of 5-(4-chlorophenyl)-N-morpholino-6-(2,2,2-trifluoroethoxy)-3-pyridinecarboxamide

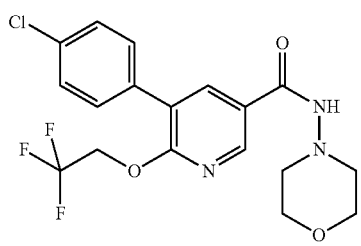 [SMILES: O=C(NN1CCOCC1)c1cnc(OCC(F)(F)F)c(-c2ccc(Cl)cc2)c1]

The title compound was synthesized in analogy to Example 1 using 5-(4-chlorophenyl)-6-(2,2,2-trifluoroethoxy)-3-pyridinecarboxylic acid (CAN 1018782-82-5) and 4-morpholinamine (CAN 4319-49-7) as starting materials; LC-MS (UV peak area/ESI) 100%, 415.0911 (M−H)⁻.

Example 3

Preparation of 5-(4-chloro-phenyl)-N-(1,1-dioxido-4-thiomorpholinyl)-6-(2,2,2-trifluoro-ethoxy)-3-pyridinecarboxamide

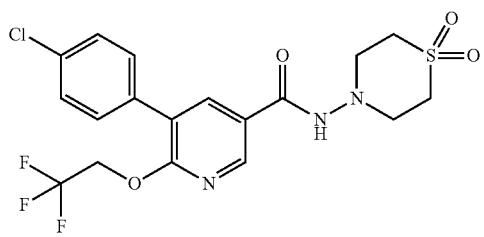 [SMILES: O=C(NN1CCS(=O)(=O)CC1)c1cnc(OCC(F)(F)F)c(-c2ccc(Cl)cc2)c1]

The title compound was synthesized in analogy to Example 1 using 5-(4-chlorophenyl)-6-(2,2,2-trifluoroethoxy)-3-pyridinecarboxylic acid (CAN 1018782-82-5) and 4-thiomorpholinamine 1,1-dioxide (CAN 26494-76-8) as starting materials; MS (EI) 464.1 (M+H)⁺.

Example 4

Preparation of t-butyl 2-[(5-(4-chlorophenyl)-6-(2,2,2-trifluoroethoxy)-3-pyridinyl)carbonyl]-pyrazolidine-1-carboxylate

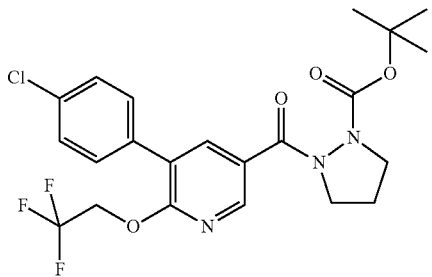 [SMILES: CC(C)(C)OC(=O)N1CCCN1C(=O)c1cnc(OCC(F)(F)F)c(-c2ccc(Cl)cc2)c1]

The title compound was synthesized in analogy to Example 1 using 5-(4-chlorophenyl)-6-(2,2,2-trifluoroethoxy)-3-pyridinecarboxylic acid (CAN 1018782-82-5) and 1-pyrazolidinecarboxylic acid 1,1-dimethylethyl ester (CAN 57699-91-9) as starting materials; MS (EI) 486.2 (M+H)⁺.

Example 5

Preparation of 5-(4-chloro-phenyl)-6-(2,2,2-trifluoro-ethoxy)-3-pyridinecarboxylic acid N'-methyl-N'-phenyl-hydrazide

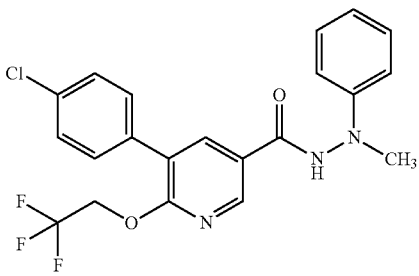 [SMILES: CN(NC(=O)c1cnc(OCC(F)(F)F)c(-c2ccc(Cl)cc2)c1)c1ccccc1]

The title compound was synthesized in analogy to Example 1 using 5-(4-chlorophenyl)-6-(2,2,2-trifluoroethoxy)-3-pyridinecarboxylic acid (CAN 1018782-82-5) and 1-methyl-1-phenyl-hydrazine (CAN 618-40-6) as starting materials; MS (EI) 436.3 (M+H)⁺.

Example 6

Preparation of 5-(4-chlorophenyl)-N-(4-hydroxypiperidin-1-yl)-6-(2,2,2-trifluoroethoxy)-3-pyridinecarboxamide

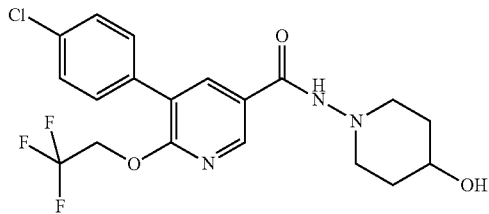 [SMILES: O=C(NN1CCC(O)CC1)c1cnc(OCC(F)(F)F)c(-c2ccc(Cl)cc2)c1]

The title compound was synthesized in analogy to Example 1 using 5-(4-chlorophenyl)-6-(2,2,2-trifluoroethoxy)-3-pyridinecarboxylic acid (CAN 1018782-82-5) and 1-amino-4-piperidinol (CAN 79414-82-7) as starting materials; LC-MS (UV peak area/ESI) 97.7%, 430.1150 (M+H)+.

Example 7

Preparation of 5-(4-chlorophenyl)-N-(5-(morpholinomethyl)-2-oxooxazolidin-3-yl)-6-(2,2,2-trifluoroethoxy)-3-pyridinecarboxamide

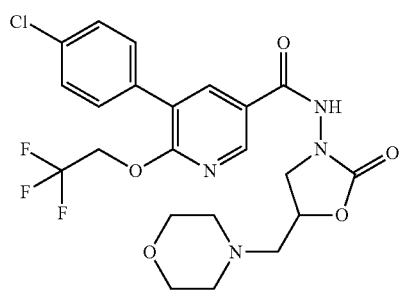 [SMILES: O=C(NN1CC(CN2CCOCC2)OC1=O)c1cnc(OCC(F)(F)F)c(-c2ccc(Cl)cc2)c1]

The title compound was synthesized in analogy to Example 1 using 5-(4-chlorophenyl)-6-(2,2,2-trifluoroethoxy)-3-pyridinecarboxylic acid (CAN 1018782-82-5) and 3-amino-5-(4-morpholinylmethyl)-2-oxazolidinone (CAN 43056-63-9) as starting materials; LC-MS (UV peak area/ESI) 97.7%, 515.1292 (M+H)+.

Example 8

Preparation of 5-(4-chlorophenyl)-N'-(6-chloropyridazin-3-yl)-N'-methyl-6-(2,2,2-trifluoroethoxy)-3-pyridinecarboxylic acid hydrazide

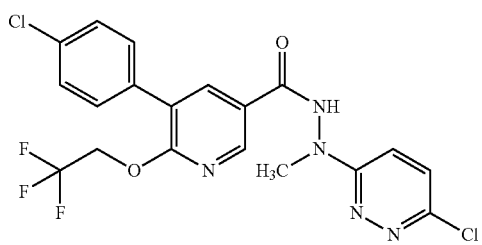 [SMILES: CN(NC(=O)c1cnc(OCC(F)(F)F)c(-c2ccc(Cl)cc2)c1)c1ccc(Cl)nn1]

The title compound was synthesized in analogy to Example 1 using 5-(4-chlorophenyl)-6-(2,2,2-trifluoroethoxy)-3-pyridinecarboxylic acid (CAN 1018782-82-5) and 3-chloro-6-(1-methylhydrazinyl)-pyridazine (CAN 76953-33-8) as starting materials; LC-MS (UV peak area/ESI) 96.8%, 472.0538 (M+H)+.

Example 9

Preparation of 5-(4-chloro-3-fluorophenyl)-6-(2,2,2-trifluoroethoxy)-3-pyridinecarboxylic acid hydrazide

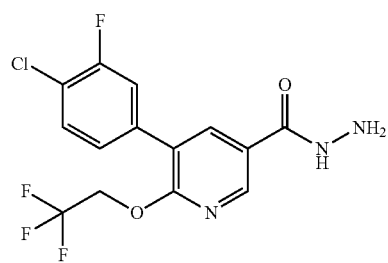 [SMILES: NNC(=O)c1cnc(OCC(F)(F)F)c(-c2ccc(Cl)c(F)c2)c1]

a) 5-(4-Chloro-3-fluoro-phenyl)-6-(2,2,2-trifluoroethoxy)-3-pyridinecarboxylic acid

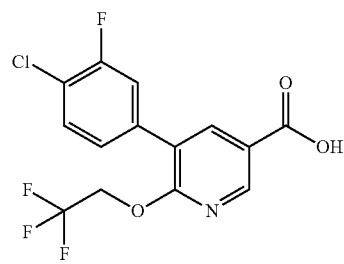 [SMILES: O=C(O)c1cnc(OCC(F)(F)F)c(-c2ccc(Cl)c(F)c2)c1]

5-Bromo-6-(2,2,2-trifluoroethoxy)-3-pyridinecarboxylic acid (4.00 g, 13.3 mmol; CAN 1211586-75-2) was dissolved in toluene (90 mL) and DMF (2.0 mL) to give a colorless solution. Then B-(4-chloro-3-fluorophenyl)-boronic acid (2.56 g, 14.7 mmol; CAN 137504-86-0), 1,1'-bis(diphenylphosphino)ferrocene-palladium(II)dichloride dichloromethane complex (544 mg, 667 μmol) and aqueous sodium carbonate solution (53.3 ml, 107 mmol, 2 M) were successively added under stirring in an argon atmosphere. The reaction mixture was stirred 2.5 h at 90° C. Subsequently the reaction mixture was cooled to ambient temperature, poured into ice-water (300 mL), acidified with 2 N HCl (120 mL) and extracted with isopropyl acetate (3×200 mL). The organic layers were combined, dried with $Na_2SO_4$ and concentrated in vacuo. The residue was digested with a mixture of n-heptane and isopropyl acetate (10 mL/2 mL) at ambient temperature, filtered off and washed with isopropyl acetate/n-heptane 1:5 (2×3 ml). The resulting brown solid was digested with dichloromethane (10 mL) at ambient temperature to give the title compound (2.57 g, 55%) after filtration and drying as off-white solid; MS (EI) 347.9 (M+H)⁺.

b) 5-(4-Chloro-3-fluoro-phenyl)-6-(2,2,2-trifluoro-ethoxy)-3-pyridinecarboxylic acid methyl ester

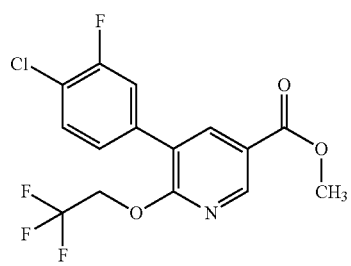 [SMILES: COC(=O)c1cnc(OCC(F)(F)F)c(-c2ccc(Cl)c(F)c2)c1]

5-(4-Chloro-3-fluorophenyl)-6-(2,2,2-trifluoroethoxy)-3-pyridinecarboxylic acid (400 mg, 1.14 mmol) was combined with thionyl chloride (5.72 g, 3.49 ml, 48.0 mmol) and 4 drops of DMF to give a light yellow suspension. The reaction mixture was stirred at 75° C. for 3 h and subsequently cooled to ambient temperature. Remaining thionyl chloride was removed by distillation. Methanol (10 mL) was added slowly at 0-5° C. to the remaining yellow solid, and the mixture was stirred at 75° C. overnight. Afterwards the reaction mixture was cooled to ambient temperature and poured into 50 mL saturated NaHCO₃ solution and extracted with isopropyl acetate (2×40 mL). The organic layers were combined, dried with Na₂SO₄ and concentrated in vacuo. The residue was digested with n-heptane (5 mL). The solid was filtered off, washed with n-heptane and dried to give the title compound (0.26 g, 63%) as off-white solid; MS (EI) 364.2 (M+H)⁺.

c) 5-(4-Chloro-3-fluorophenyl)-6-(2,2,2-trifluoroethoxy)-3-pyridinecarboxylic acid hydrazide 5-(4-Chloro-3-fluoro-phenyl)-6-(2,2,2-trifluoro-ethoxy)-3-pyridinecarboxylic acid methyl ester (97 mg, 267 µmol) was dissolved in ethanol (2 mL) to give a light yellow solution. Hydrazine monohydrate (134 mg, 130 µl, 2.67 mmol) was added under argon. The reaction mixture was stirred under argon at reflux temperature (85° C.) for 5 h. Subsequently the reaction mixture was poured into 10 mL saturated aqueous Na₂CO₃ solution and extracted with isopropyl acetate (2×20 mL). The organic layers were combined, dried with Na₂SO₄ and concentrated in vacuo to give the title compound (63 mg, 65%) as off-white solid; MS (ESI) 361.8 (M−H)⁻.

Example 10

Preparation of 5-(4-chlorophenyl)-6-(cyclopropyl-methoxy)-N-(4-hydroxypiperidin-1-yl)-3-pyridinecarboxamide

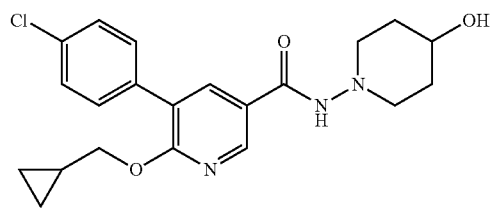 [SMILES: O=C(NN1CCC(O)CC1)c1cnc(OCC2CC2)c(-c2ccc(Cl)cc2)c1]

The title compound was synthesized in analogy to Example 1 using 5-(4-chlorophenyl)-6-(cyclopropyl-methoxy)-3-pyridinecarboxylic acid (CAN 1018782-76-7) and 1-amino-4-piperidinol (CAN 79414-82-7) as starting materials; MS (EI) 402.4 (M+H)⁺.

Example 11

Preparation of 5-(4-chlorophenyl)-6-cyclobutoxy-N-(4-hydroxypiperidin-1-yl)-3-pyridinecarboxamide

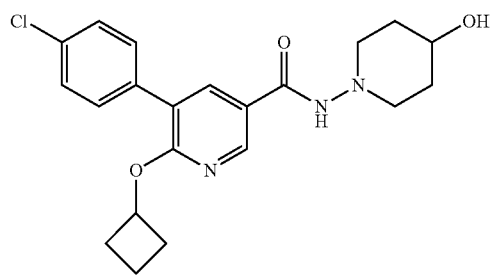 [SMILES: O=C(NN1CCC(O)CC1)c1cnc(OC2CCC2)c(-c2ccc(Cl)cc2)c1]

a) 5-Bromo-6-cyclobutoxy-3-pyridinecarboxylic acid

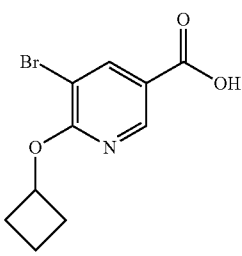 [SMILES: O=C(O)c1cnc(OC2CCC2)c(Br)c1]

5-Bromo-6-chloro-3-pyridinecarboxylic acid (CAN 29241-62-1, 2.0 g, 8.46 mmol) was dissolved in DMSO (20.0 mL). Cyclobutanol (793 mg, 857 µL, 11.0 mmol) and potassium hydroxide powder (1.42 g, 25.4 mmol) were added and the mixture was stirred at room temperature overnight. Water (20 mL) was added and the mixture was acidified (under ice-water bath cooling) with 37% HCl in water (pH=2). The suspension was filtered, washed with water and the solid was dried to yield 1.88 g (82%) of the title compound as a white solid; MS (ESI): 270.2 (M−H)⁻.

b) 5-(4-Chloro-phenyl)-6-cyclobutoxy-3-pyridinecarboxylic acid

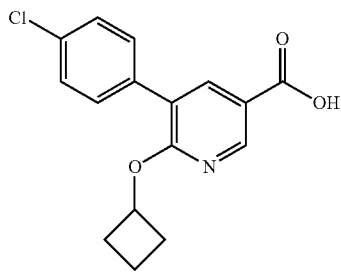 [SMILES: O=C(O)c1cnc(OC2CCC2)c(-c2ccc(Cl)cc2)c1]

The title compound was synthesized in analogy to Example 9a using 5-bromo-6-cyclobutoxy-3-pyridinecarboxylic acid and B-(4-chlorophenyl)-boronic acid (CAN 1679-18-1) as starting materials; MS (ESI): 302.2 (M−H)⁻.

c) 5-(4-Chlorophenyl)-6-cyclobutoxy-N-(4-hydroxypiperidin-1-yl)-3-pyridinecarboxamide The title compound was synthesized in analogy to Example 1 using 5-(4-chlorophenyl)-6-(cyclobutoxy)-3-pyridinecarboxylic acid and 1-amino-4-piperidinol (CAN 79414-82-7) as starting materials; MS (EI) 402.4 (M+H)⁺.

Example 12

Preparation of 5-cyclohexyl-N-(4-hydroxypiperidin-1-yl)-6-(2,2,2-trifluoroethoxy)-3-pyridinecarboxamide

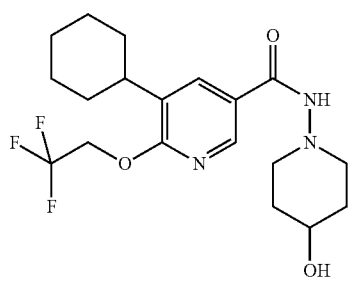 [SMILES: O=C(NN1CCC(O)CC1)c1cnc(OCC(F)(F)F)c(C2CCCCC2)c1]

a) 5-Cyclohex-1-enyl-6-(2,2,2-trifluoroethoxy)-3-pyridinecarboxylic acid methyl ester

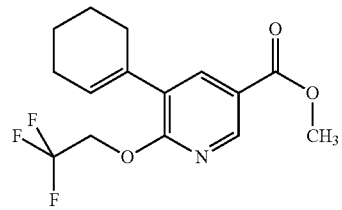 [SMILES: COC(=O)c1cnc(OCC(F)(F)F)c(C2=CCCCC2)c1]

5-Bromo-6-(2,2,2-trifluoroethoxy)-3-pyridinecarboxylic acid methyl ester (500 mg, 1.59 mmol, CAN 1211589-51-3), potassium carbonate (660 mg, 4.78 mmol) and 1,1'-bis(diphenylphosphino)ferrocene-palladium(II)dichloride dichloromethane complex (65.0 mg, 79.6 μmol) were combined to give a light red solid. To this solid was added a solution of 2-(1-cyclohexen-1-yl)-4,4,5,5-tetramethyl-1,3,2-dioxaborolane (331 mg, 1.59 mmol, CAN 141091-37-4) in DMF (12.0 ml), that had been thoroughly degassed and flushed with argon. The reaction mixture was heated to 80° C. and stirred for 48 h. Subsequently the reaction mixture was cooled to ambient temperature and poured into 75 mL brine and extracted with isopropyl acetate (2×150 mL). The organic layers were washed with brine (2×50 mL), combined and dried with Na₂SO₄ and concentrated in vacuo. The residue was purified by flash chromatography (silica gel, 50 g, 0% to 10%, n-heptane/isopropyl acetate) to give the title compound (0.43 g, 60%) as white solid; MS (EI) 316.3 (M+H)⁺.

b) 5-Cyclohexyl-6-(2,2,2-trifluoro-ethoxy)-3-pyridinecarboxylic acid methyl ester

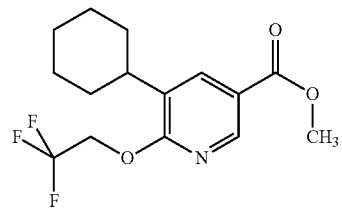 [SMILES: COC(=O)c1cnc(OCC(F)(F)F)c(C2CCCCC2)c1]

5-Cyclohex-1-enyl-6-(2,2,2-trifluoroethoxy)-3-pyridinecarboxylic acid methyl ester (163 mg, 517 μmol) was combined with ethanol (5 mL) to give a colorless solution. Palladium (10% on charcoal, 16.3 mg, 517 μmol) was added and the suspension was evacuated and flushed with hydrogen 3 times and stirred for 1.5 h at ambient temperature. Afterwards the reaction mixture was filtered through Celite and concentrated in vacuo to give the title compound (95 mg, 58%) as grey solid; MS (EI) 318.1 (M+H)+.

c) 5-Cyclohexyl-6-(2,2,2-trifluoro-ethoxy)-3-pyridinecarboxylic acid

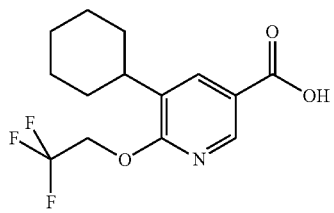 [SMILES: O=C(O)c1cnc(OCC(F)(F)F)c(C2CCCCC2)c1]

5-Cyclohexyl-6-(2,2,2-trifluoroethoxy)-3-pyridinecarboxylic acid methyl ester (95 mg, 299 μmol) was combined with THF (4 mL) and water (2 mL) to give a light yellow solution. Lithium hydroxide hydrate (25.1 mg, 599 μmol) was added under argon. The reaction mixture stirred at ambient temperature overnight, subsequently poured into 6 mL 2 M HCl and extracted with isopropyl acetate (2×60 mL). The organic layers were combined, dried with $Na_2SO_4$ and concentrated in vacuo to give the title compound (92 mg, quant.) as white solid; MS (ESI) 302.0 (M−H)−.

d) 5-Cyclohexyl-N-(4-hydroxypiperidin-1-yl)-6-(2,2,2-trifluoroethoxy)-3-pyridinecarboxamide The title compound was synthesized in analogy to Example 1 using 5-cyclohexyl-6-(2,2,2-trifluoro-ethoxy)-3-pyridinecarboxylic acid and 1-amino-4-piperidinol (CAN 79414-82-7) as starting materials; LC-MS (UV peak area/ESI) 96.4%, 402.1991 (M+H)+.

Example 13

Preparation of 5-(4-chlorophenyl)-N-(4-(methylsulfonyl)piperazin-1-yl)-6-(2,2,2-trifluoroethoxy)-3-pyridinecarboxamide

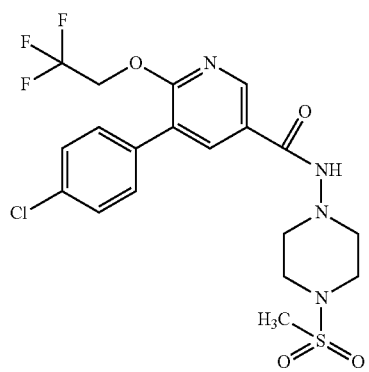 [SMILES: CS(=O)(=O)N1CCN(NC(=O)c2cnc(OCC(F)(F)F)c(-c3ccc(Cl)cc3)c2)CC1]

a) 4-{[5-(4-Chloro-phenyl)-6-(2,2,2-trifluoro-ethoxy)-pyridine-3-carbonyl]-amino}-piperazine-1-carboxylic acid tert-butyl ester

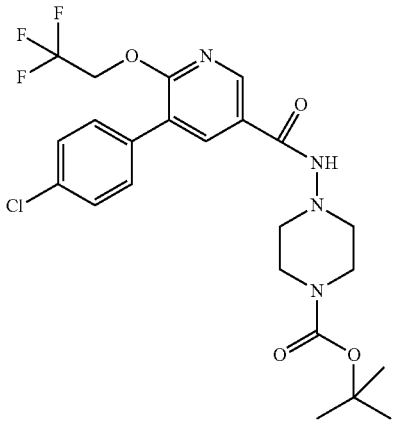 [SMILES: CC(C)(C)OC(=O)N1CCN(NC(=O)c2cnc(OCC(F)(F)F)c(-c3ccc(Cl)cc3)c2)CC1]

The title compound was synthesized in analogy to Example 1 using 5-(4-chlorophenyl)-6-(2,2,2-trifluoroethoxy)-3-pyridinecarboxylic acid (CAN 1018782-82-5) and 4-amino-1-piperazinecarboxylic acid 1,1-dimethylethyl ester (CAN 118753-66-5) as starting materials; MS (EI) 515.2 (M+H)+.

b) 5-(4-Chloro-phenyl)-N-piperazin-1-yl-6-(2,2,2-trifluoro-ethoxy)-3-pyridinecarboxamide trifluoroacetate (1:1)

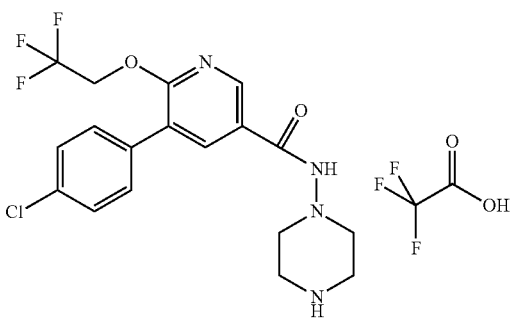

4-{[5-(4-Chloro-phenyl)-6-(2,2,2-trifluoro-ethoxy)-pyridine-3-carbonyl]-amino}-piperazine-1-carboxylic acid tert-butyl ester (1.047 g, 2.03 mmol) was combined with dichloromethane (25 mL) to give a white suspension. Subsequently trifluoroacetic acid (7.4 g, 5 ml, 64.9 mmol) was added at 0° C. and the reaction mixture was stirred at 0° C. for 2 h. The reaction mixture was concentrated in vacuo and the residue was crystallized from ethyl acetate and n-heptane to afford the title compound (1.0 g, quant.) as white solid.

c) 5-(4-Chlorophenyl)-N-(4-(methylsulfonyl)piperazin-1-yl)-6-(2,2,2-trifluoroethoxy)-3-pyridinecarboxamide 5-(4-Chlorophenyl)-N-(piperazin-1-yl)-6-(2,2,2-trifluoroethoxy)-3-pyridinecarboxamide 2,2,2-trifluoroacetate (1:1) (100 mg, 189 μmol) was combined with dichloromethane (5 mL) to give a white suspension. N,N-Diisopropylethylamine (122 mg, 165 µl, 945 µmol) and methanesulfonyl chloride (23.8 mg, 16.1 µl, 208 µmol) were added successively at 0° C. The reaction mixture was stirred for 1 h at 0° C. and subsequently concentrated in vacuo. The residue was purified by flash chromatography (silica gel, 20 g, 0% to 100% ethyl acetate in n-heptane). Recrystallization from ethyl acetate and n-heptane afforded the title compound (50 mg, 54%) as off-white solid; LC-MS (UV peak area/ESI) 98.0%, 493.0916 (M+H)⁺.

Example 14

Preparation of 5-cyclopentyl-N-morpholino-6-(2,2,2-trifluoroethoxy)-3-pyridinecarboxamide

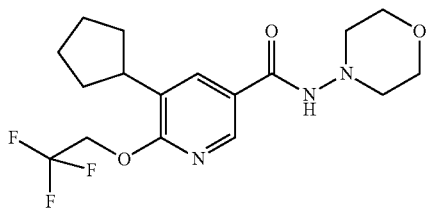 [SMILES: O=C(NN1CCOCC1)c1cnc(OCC(F)(F)F)c(C2CCCC2)c1]

a) 5-Cyclopent-1-enyl-6-(2,2,2-trifluoro-ethoxy)-3-pyridinecarboxylic acid methyl ester

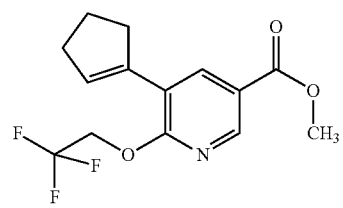 [SMILES: COC(=O)c1cnc(OCC(F)(F)F)c(C2=CCCC2)c1]

The title compound was synthesized in analogy to Example 12a using 5-bromo-6-(2,2,2-trifluoroethoxy)-3-pyridinecarboxylic acid methyl ester (CAN 1211589-51-3) and 2-(1-cyclopenten-1-yl)-4,4,5,5-tetramethyl-1,3,2-dioxaborolane (CAN 287944-10-9) as starting materials; MS (EI) 302.0 (M+H)⁺.

b) 5-Cyclopentyl-6-(2,2,2-trifluoro-ethoxy)-3-pyridinecarboxylic acid methyl ester

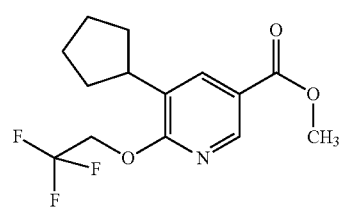 [SMILES: COC(=O)c1cnc(OCC(F)(F)F)c(C2CCCC2)c1]

The title compound was synthesized in analogy to Example 12b using 5-cyclopent-1-enyl-6-(2,2,2-trifluoro-ethoxy)-3-pyridinecarboxylic acid methyl ester as starting material; MS (EI) 303.9 (M+H)⁺.

c) 5-Cyclopentyl-6-(2,2,2-trifluoro-ethoxy)-3-pyridinecarboxylic acid

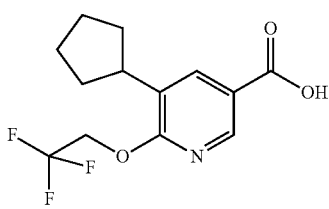 [SMILES: O=C(O)c1cnc(OCC(F)(F)F)c(C2CCCC2)c1]

The title compound was synthesized in analogy to Example 12c using 5-cyclohexyl-6-(2,2,2-trifluoro-ethoxy)-3-pyridinecarboxylic acid methyl ester as starting material; MS (ESI) 287.8 (M−H)⁻.

d) 5-Cyclopentyl-N-morpholino-6-(2,2,2-trifluoroethoxy)-3-pyridinecarboxamide

The title compound was synthesized in analogy to Example 1 using 5-cyclopentyl-6-(2,2,2-trifluoro-ethoxy)-3-pyridinecarboxylic acid and 4-morpholinamine (CAN 4319-49-7) as starting materials; MS (ESI) 372.1 (M−H)⁻.

Example 15

Preparation of 5-cyclopentyl-N-(2-oxopyrrolidin-1-yl)-6-(2,2,2-trifluoroethoxy)-3-pyridinecarboxamide

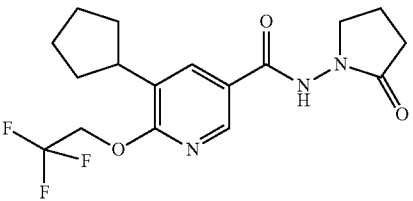 [SMILES: O=C(NN1CCCC1=O)c1cnc(OCC(F)(F)F)c(C2CCCC2)c1]

The title compound was synthesized in analogy to Example 1 using 5-cyclopentyl-6-(2,2,2-trifluoro-ethoxy)-3- pyridinecarboxylic acid (example 14c) and 1-amino-2-pyrrolidinone (CAN 6837-14-5) as starting materials; MS (EI) 372.1 (M+H)⁺.

Example 16

Preparation of N'-(6-chloropyridazin-3-yl)-5-cyclopentyl-N'-methyl-6-(2,2,2-trifluoroethoxy)-3-pyridinecarboxylic acid hydrazide

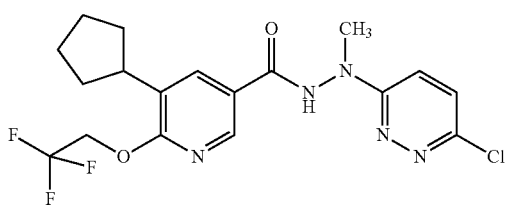 [SMILES: CN(NC(=O)c1cnc(OCC(F)(F)F)c(C2CCCC2)c1)c1ccc(Cl)nn1]

The title compound was synthesized in analogy to Example 1 using 5-cyclopentyl-6-(2,2,2-trifluoro-ethoxy)-3-pyridinecarboxylic acid (example 14c) and 3-chloro-6-(1-methylhydrazinyl)-pyridazine (CAN 76953-33-8) as starting materials; MS (EI) 430.4 (M+H)⁺.

Example 17

Preparation of (S)-5-cyclopentyl-N-(2-(methoxymethyl)pyrrolidin-1-yl)-6-(2,2,2-trifluoroethoxy)-3-pyridinecarboxamide

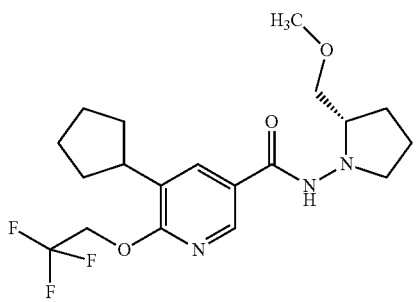 [SMILES: COC[C@@H]1CCCN1NC(=O)c1cnc(OCC(F)(F)F)c(C2CCCC2)c1]

The title compound was synthesized in analogy to Example 1 using 5-cyclopentyl-6-(2,2,2-trifluoro-ethoxy)-3-pyridinecarboxylic acid (example 14c) and (2S)-2-(methoxymethyl)-1-pyrrolidinamine (CAN 59983-39-0) as starting materials; MS (EI) 402.3 (M+H)⁺.

Example 18

Preparation of 5-cyclopentyl-N'-methyl-N'-phenyl-6-(2,2,2-trifluoroethoxy)-3-pyridinecarboxylic acid hydrazide

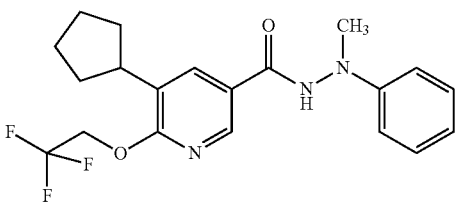 [SMILES: CN(NC(=O)c1cnc(OCC(F)(F)F)c(C2CCCC2)c1)c1ccccc1]

The title compound was synthesized in analogy to Example 1 using 5-cyclopentyl-6-(2,2,2-trifluoro-ethoxy)-3-pyridinecarboxylic acid (example 14c) and 1-methyl-1-phenyl-hydrazine (CAN 618-40-6) as starting materials; LC-MS (UV peak area/ESI) 98.0%, 394.1737 (M+H)⁺.

Example 19

Preparation of 5-cyclohexyl-N-morpholino-6-(2,2,2-trifluoroethoxy)-3-pyridinecarboxamide

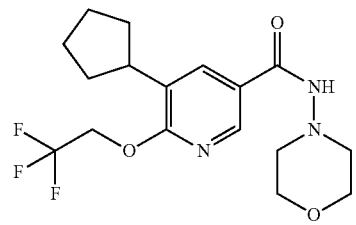 [SMILES: O=C(NN1CCOCC1)c1cnc(OCC(F)(F)F)c(C2CCCC2)c1]

The title compound was synthesized in analogy to Example 1 using 5-cyclohexyl-6-(2,2,2-trifluoro-ethoxy)-3-pyridinecarboxylic acid (example 12c) and 4-morpholinamine (CAN 4319-49-7) as starting materials; LC-MS (UV peak area/ESI) 99.0%, 388.1849 (M+H)⁺.

Example 20

Preparation of 5-cyclohexyl-N'-methyl-N'-phenyl-6-(2,2,2-trifluoroethoxy)-3-pyridinecarboxylic acid hydrazide

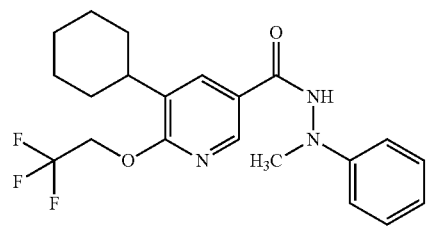 [SMILES: CN(NC(=O)c1cnc(OCC(F)(F)F)c(C2CCCCC2)c1)c1ccccc1]

The title compound was synthesized in analogy to Example 1 using 5-cyclohexyl-6-(2,2,2-trifluoro-ethoxy)-3-pyridinecarboxylic acid (example 12c) and 1-methyl-1-phenyl-hydrazine (CAN 618-40-6) as starting materials; MS (EI) 408.4 (M+H)⁺.

Example 21

Preparation of 5-cyclohexyl-N-(pyrrolidin-1-yl)-6-(2,2,2-trifluoroethoxy)-3-pyridinecarboxamide

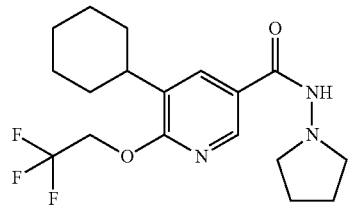 [SMILES: O=C(NN1CCCC1)c1cnc(OCC(F)(F)F)c(C2CCCCC2)c1]

The title compound was synthesized in analogy to Example 1 using 5-cyclohexyl-6-(2,2,2-trifluoro-ethoxy)-3-pyridinecarboxylic acid (example 12c) and 1-pyrrolidinamine (CAN 16596-41-1) as starting materials; LC-MS (UV peak area/ESI) 100.0%, 372.1899 (M+H)⁺.

Example 22

Preparation of N'-(6-chloropyridazin-3-yl)-5-cyclohexyl-N'-methyl-6-(2,2,2-trifluoroethoxy)-3-pyridinecarboxylic acid hydrazide

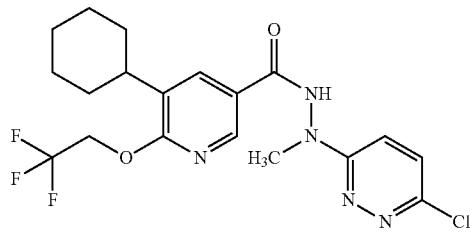 [SMILES: CN(NC(=O)c1cnc(OCC(F)(F)F)c(C2CCCCC2)c1)c1ccc(Cl)nn1]

The title compound was synthesized in analogy to Example 1 using 5-cyclohexyl-6-(2,2,2-trifluoro-ethoxy)-3-pyridinecarboxylic acid (example 12c) and 3-chloro-6-(1-methylhydrazinyl)-pyridazine (CAN 76953-33-8) as starting materials; LC-MS (UV peak area/ESI) 100.0%, 444.1408 (M+H)⁺.

Example 23

Preparation of 5-cyclohexyl-N—((S)-2-methoxymethyl-pyrrolidin-1-yl)-6-(2,2,2-trifluoro-ethoxy)-3-pyridinecarboxamide

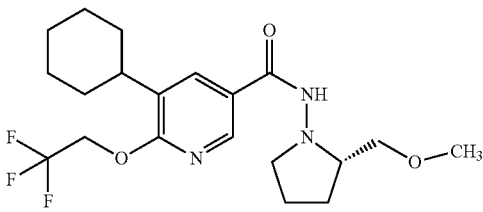 [SMILES: COC[C@@H]1CCCN1NC(=O)c1cnc(OCC(F)(F)F)c(C2CCCCC2)c1]

The title compound was synthesized in analogy to Example 1 using 5-cyclohexyl-6-(2,2,2-trifluoro-ethoxy)-3-pyridinecarboxylic acid (example 12c) and (2S)-2-(methoxymethyl)-1-pyrrolidinamine (CAN 59983-39-0) as starting materials; LC-MS (UV peak area/ESI) 98.8%, 416.2159 (M+H)⁺.

Example 24

Preparation of 5-(4-chlorophenyl)-N-(4-(2-hydroxyethyl)piperidin-1-yl)-6-(2,2,2-trifluoroethoxy)-3-pyridinecarboxamide

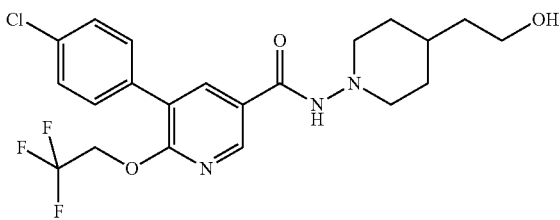 [SMILES: O=C(NN1CCC(CCO)CC1)c1cnc(OCC(F)(F)F)c(-c2ccc(Cl)cc2)c1]

a) 4-[2-(t-Butyl-dimethyl-silanyloxy)-ethyl]-piperidine hydrochloride (1:1)

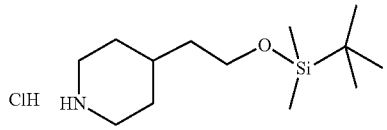 [SMILES: Cl ; CC(C)(C)[Si](C)(C)OCCC1CCNCC1]

4-Piperidineethanol (2 g, 15.5 mmol) and N,N-diisopropylethylamine (3.00 g, 4.06 ml, 23.2 mmol) were combined with dichloromethane (50 mL) to give a colorless solution. t-Butyldimethylchlorosilane (2.8 g, 18.6 mmol) in dichloromethane (30 mL) was added to this solution during 15 min at 0° C. The reaction mixture was stirred for 2.5 h at 0° C. and afterwards for 21 h at room temperature. Subsequently the reaction mixture was concentrated in vacuo and the residue was crystallized from ethyl acetate and n-heptane (100 ml, 1:1) to give the title compound (3.45 g, 80%) as light yellow solid; GC-MS (EI) 243.0 (M)+.

b) {-4-[2-(t-Butyl-dimethyl-silanyloxy)-ethyl]-piperidin-1-yl}-carbamic acid t-butyl ester

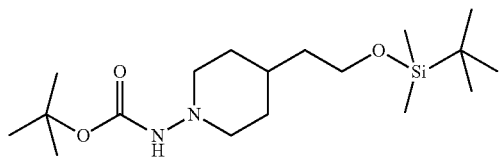 [SMILES: CC(C)(C)OC(=O)NN1CCC(CCO[Si](C)(C)C(C)(C)C)CC1]

4-[2-(t-Butyl-dimethyl-silanyloxy)-ethyl]-piperidine hydrochloride (1:1) (300 mg, 1.07 mmol) was combined with dichloromethane (15 mL) to give a light yellow suspension. N,N-Diisopropylethylamine (166 mg, 225 µl, 1.29 mmol) was added at 0° C. Subsequently 3-(4-cyanophenyl)-2-oxaziridinecarboxylic acid 1,1-dimethylethyl ester (238 mg, 965 µmol) in dichloromethane (10 mL) was added during 20 min at 0° C. and the reaction mixture was stirred for 1 h at 0° C. Afterwards the reaction mixture was concentrated in vacuo and the residue was purified by flash chromatography (silica gel, 20 g, 0% to 40% ethyl acetate in n-heptane) to deliver an oil contaminated with 4-cyano-benzaldehyde. This material was purified by a second chromatography (aminophase 10 g, ethyl acetetate/n-heptane 1/1) to give the title compound (0.23 g, 60%) as a white solid; LC-MS (ESI) 94.9%, 359.2710 (M+H)+.

c) 4-[2-(t-Butyl-dimethyl-silanyloxy)-ethyl]-piperidin-1-ylamine trifluoroacetate (1:1)

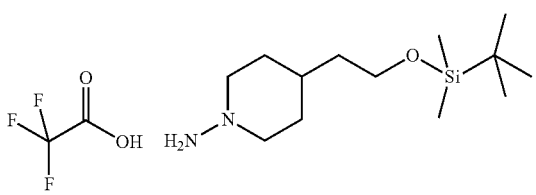 [SMILES: O=C(O)C(F)(F)F ; CC(C)(C)[Si](C)(C)OCCC1CCN(N)CC1]

{4-[2-(t-Butyl-dimethyl-silanyloxy)-ethyl]-piperidin-1-yl}-carbamic acid t-butyl ester (168 mg, 468 µmol) was at 0° C. combined with dichloromethane (2 mL) and trifluoroacetic acid (2 mL) to give a light yellow solution. The reaction mixture was stirred for 2 h at 0° C. and subsequently concentrated in vacuo to give the title compound as yellow oil, which was used without further purification in the next step.

d) 5-(4-Chlorophenyl)-N-(4-(2-hydroxyethyl)piperidin-1-yl)-6-(2,2,2-trifluoroethoxy)-3-pyridinecarboxamide The title compound was synthesized in analogy to Example 1 using 5-(4-chlorophenyl)-6-(2,2,2-trifluoroethoxy)-3-pyridinecarboxylic acid (CAN 1018782-82-5) and 4-[2-(t-butyl-dimethyl-silanyloxy)-ethyl]-piperidin-1-ylamine trifluoroacetate (1:1) as starting materials; the silyl protecting group was lost during reaction and work-up; LC-MS (UV peak area/ESI) 94.9%, 458.1448 (M+H)+.

Example 25

Preparation of 5-(4-chlorophenyl)-N-(4-(2-hydroxyethyl)piperazin-1-yl)-6-(2,2,2-trifluoroethoxy)-3-pyridinecarboxamide

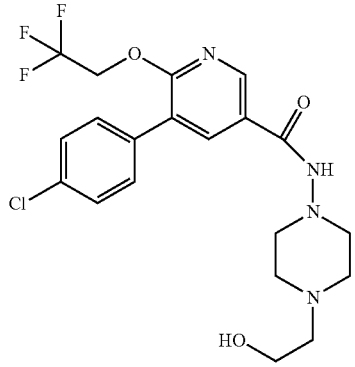 [SMILES: O=C(NN1CCN(CCO)CC1)c1cnc(OCC(F)(F)F)c(-c2ccc(Cl)cc2)c1]

a) Acetic acid 2-(4-{[5-(4-chloro-phenyl)-6-(2,2,2-trifluoro-ethoxy)-pyridine-3-carbonyl]-amino}-piperazin-1-yl)-ethyl ester

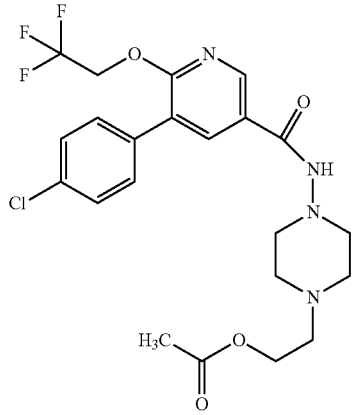 [SMILES: CC(=O)OCCN1CCN(NC(=O)c2cnc(OCC(F)(F)F)c(-c3ccc(Cl)cc3)c2)CC1]

5-(4-Chloro-phenyl)-N-piperazin-1-yl-6-(2,2,2-trifluoroethoxy)-3-pyridinecarboxamide trifluoroacetate (1:1) (200 mg, 378 µmol, example 13b) was combined with acetonitrile (10 mL) to give a yellow solution. To this solution 2-bromoethyl acetate (760 mg, 500 µl, 4.55 mmol) and K₂CO₃ (157 mg, 1.13 mmol) were added successively. The reaction mixture was heated to 60° C., stirred for 20 h, filtered through a Celite® pad after cooling to ambient temperature and the filtrate was concentrated in vacuo. The residue was purified by flash chromatography (silica gel, 20 g, 0% to 50% methanol in ethyl acetate) to give the title compound (107 mg, 57%) as white solid; LC-MS (UV peak area/ESI) 97.8%, 501.1510 (M+H)+.

b) 5-(4-Chlorophenyl)-N-(4-(2-hydroxyethyl)piperazin-1-yl)-6-(2,2,2-trifluoroethoxy)-3-pyridinecarboxamide Acetic acid 2-(4-{[5-(4-chloro-phenyl)-6-(2,2,2-trifluoroethoxy)-pyridine-3-carbonyl]-amino}-piperazin-1-yl)-ethyl ester (100 mg, 200 µmol) was combined with THF (2 mL), methanol (1 mL) and water (1 mL) to give a light yellow solution. Lithium hydroxide (14.3 mg, 599 µmol) was added and the mixture was stirred for 1 h at room temperature. Subsequently the reaction mixture was concentrated in vacuo and the residue was purified by flash chromatography (silica gel, 12 g, 0% to 100% ethyl acetate in n-heptane) to give the title compound (32 mg, 35%) as light yellow solid; MS (EI) 459.2 (M+H)$^+$.

Example 26

Preparation of 5-(4-chlorophenyl)-N-(4-(hydroxymethyl)piperidin-1-yl)-6-(2,2,2-trifluoroethoxy)-3-pyridinecarboxamide

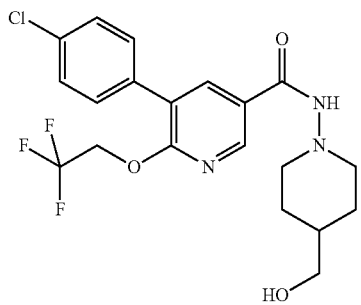 [SMILES: O=C(NN1CCC(CO)CC1)c1cnc(OCC(F)(F)F)c(-c2ccc(Cl)cc2)c1]

a) [4-(t-Butyl-dimethyl-silanyloxymethyl)-piperidin-1-yl]-carbamic acid t-butyl ester

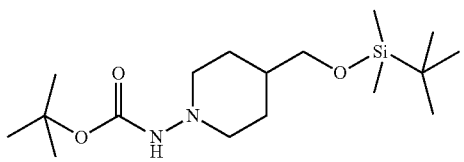 [SMILES: CC(C)(C)OC(=O)NN1CCC(CO[Si](C)(C)C(C)(C)C)CC1]

4-[[[(1,1-Dimethylethyl)dimethylsilyl]oxy]methyl]-piperidine hydrochloride (1:1) (300 mg, 1.13 mmol) was combined with dichloromethane (50 mL) to give a light yellow suspension. N,N-Diisopropylethylamine (175 mg, 236 µl, 1.35 mmol) was added at 0° C. Subsequently 3-(4-cyanophenyl)-2-oxaziridinecarboxylic acid 1,1-dimethylethyl ester (250 mg, 1.02 mmol) in dichloromethane (10 mL) was added during 20 min at 0° C. and the reaction mixture was stirred for 1 h at 0° C. Afterwards the reaction mixture was concentrated in vacuo and the residue was purified by flash chromatography (silica gel, 20 g, 0% to 40% ethyl acetate in n-heptane) to deliver an oil contaminated with 4-cyano-benzaldehyde. This material was purified by a second chromatography (aminophase 10 g, ethyl acetate/n-heptane 1/1) to give the title compound (0.24 g, 62%) as white solid; GC-MS (EI) 344.0 (M)$^+$.

b) 4-(t-Butyl-dimethyl-silanyloxymethyl)-piperidin-1-ylamine trifluoroacetate (1:1)

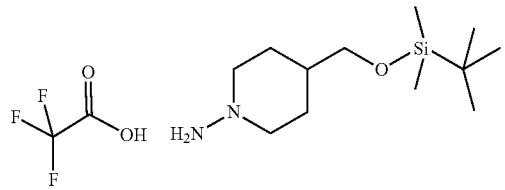 [SMILES: O=C(O)C(F)(F)F ; CC(C)(C)[Si](C)(C)OCC1CCN(N)CC1]

[4-(t-Butyl-dimethyl-silanyloxymethyl)-piperidin-1-yl]-carbamic acid t-butyl ester (100 mg, 290 µmol) was at 0° C. combined with dichloromethane (3 mL) and trifluoroacetic acid (3 mL) to give a light yellow solution. The reaction mixture was stirred for 2 h at 0° C. and subsequently concentrated in vacuo to give the title compound as yellow oil, which was used without further purification in the next step.

c) 5-(4-Chlorophenyl)-N-(4-(2-hydroxyethyl)piperidin-1-yl)-6-(2,2,2-trifluoroethoxy)-3-pyridinecarboxamide The title compound was synthesized in analogy to Example 1 using 5-(4-chlorophenyl)-6-(2,2,2-trifluoroethoxy)-3-pyridinecarboxylic acid (CAN 1018782-82-5) and 4-(t-butyl-dimethyl-silanyloxymethyl)-piperidin-1-ylamine trifluoroacetate (1:1) as starting materials; the silyl protecting group was lost during reaction and work-up; LC-MS (UV peak area/ESI) 96.6%, 444.1292 (M+H)$^+$.

Example 27

Preparation of 5-(4-chlorophenyl)-N-(4-methyl-3-oxopiperazin-1-yl)-6-(2,2,2-trifluoroethoxy)-3-pyridinecarboxamide

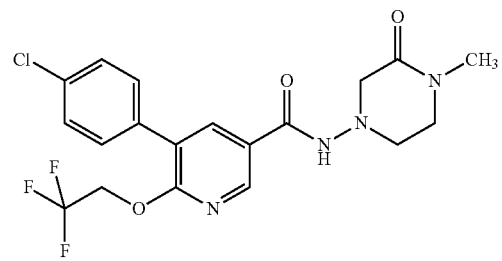 [SMILES: CN1CCN(NC(=O)c2cnc(OCC(F)(F)F)c(-c3ccc(Cl)cc3)c2)CC1=O]

a) (4-Methyl-3-oxo-piperazin-1-yl)-carbamic acid t-butyl ester

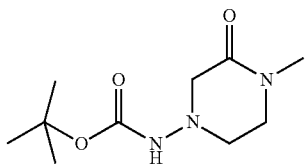 [SMILES: CN1CCN(NC(=O)OC(C)(C)C)CC1=O]

Methyl-2-piperazinone hydrochloride (1:1) (300 mg, 1.99 mmol) was combined with dichloromethane (20 mL) to give a light yellow suspension. N,N-Diisopropylethylamine (309 mg, 417 µl, 2.39 mmol) was added at 0° C. Subsequently 3-(4-cyanophenyl)-2-oxaziridinecarboxylic acid 1,1-dimethylethyl ester (441 mg, 1.79 mmol) in dichloromethane (10 mL) was added during 35 min at 0° C. and the reaction mixture was stirred for 1 h at 0° C. Afterwards the reaction mixture was concentrated in vacuo and the residue was purified by flash chromatography (silica gel, 20 g, 0% to 100% ethyl acetate in n-heptane) to deliver an oil contaminated with 4-cyano-benzaldehyde. This material was purified by a second chromatography (aminophase 5 g, ethyl acetate/n-heptane 1/1) to give the title compound (67 mg, 15%) as white solid; GC-MS (EI) 229.0 (M)$^+$.

b) 4-Amino-1-methyl-piperazin-2-one trifluoroacetate (1:1)

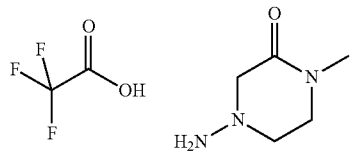

(4-Methyl-3-oxo-piperazin-1-yl)-carbamic acid t-butyl ester (67 mg, 292 µmol) was at 0° C. combined with dichloromethane (2 mL) and trifluoroacetic acid (1 mL) to give a light yellow solution. The reaction mixture was stirred for 2 h at 0° C. and subsequently concentrated in vacuo to give the title compound as yellow oil, which was used without further purification in the next step.

c) 5-(4-Chlorophenyl)-N-(4-methyl-3-oxopiperazin-1-yl)-6-(2,2,2-trifluoroethoxy)-3-pyridinecarboxamide The title compound was synthesized in analogy to Example 1 using 5-(4-chlorophenyl)-6-(2,2,2-trifluoroethoxy)-3-pyridinecarboxylic acid (CAN 1018782-82-5) and 4-amino-1-methyl-piperazin-2-one trifluoroacetate (1:1) as starting materials; LC-MS (UV peak area/ESI) 94.7%, 443.1084 (M+H)$^+$.

Example 28

Preparation of 5-(4-chlorophenyl)-N'-(3-hydroxypropyl)-N'-methyl-6-(2,2,2-trifluoroethoxy)-3-pyridinecarboxylic acid hydrazide

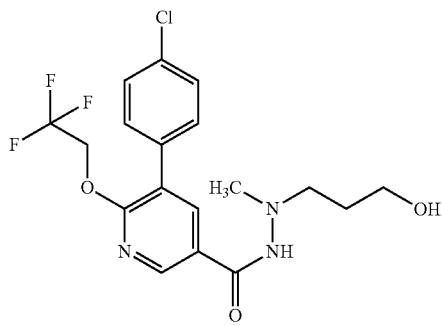 [SMILES: CN(CCCO)NC(=O)c1cnc(OCC(F)(F)F)c(-c2ccc(Cl)cc2)c1]

a) N'-[3-(t-Butyl-dimethyl-silanyloxy)-propyl]-N'-methyl-hydrazinecarboxylic acid t-butyl ester

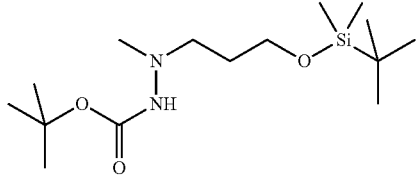 [SMILES: CN(CCCO[Si](C)(C)C(C)(C)C)NC(=O)OC(C)(C)C]

3-[[(1,1-Dimethylethyl)dimethylsilyl]oxy]-N-methyl-1-propanamine hydrochloride (1:1) (720 mg, 3.0 mmol) was combined with dichloromethane (30 mL) to give a colorless solution. N,N-Diisopropylethylamine (313 mg, 423 µl, 2.42 mmol) was added at 0° C. Subsequently 3-(4-cyanophenyl)-2-oxaziridinecarboxylic acid 1,1-dimethylethyl ester (542 mg, 2.2 mmol) in dichloromethane (20 mL) was added during 15 min at 0° C. and the reaction mixture was stirred for 1 h at 0° C. Afterwards the reaction mixture was concentrated in vacuo and the residue was purified by flash chromatography (silica gel, 20 g, 0% to 70% ethyl acetate in n-heptane) to deliver an oil contaminated with 4-cyano-benzaldehyde. This material was purified by a second chromatography (aminophase 20 g, ethyl acetate/n-heptane 1/1) to give the title compound as colorless oil.

b) N-[3-(t-Butyl-dimethyl-silanyloxy)-propyl]-N-methyl-hydrazine trifluoroacetate (1:1)

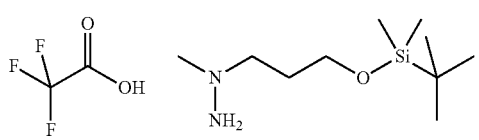

N'-[3-(t-Butyl-dimethyl-silanyloxy)-propyl]-N'-methyl-hydrazinecarboxylic acid t-butyl ester (120 mg, 377 µmol) was at 0° C. combined with dichloromethane (2 mL) and trifluoroacetic acid (2 mL) to give a light yellow solution. The reaction mixture was stirred for 2 h at 0° C. and subsequently concentrated in vacuo to give the title compound as yellow oil, which was used without further purification in the next step.

c) 5-(4-Chlorophenyl)-N'-(3-hydroxypropyl)-N'-methyl-6-(2,2,2-trifluoroethoxy)-3-pyridinecarboxylic acid hydrazide The title compound was synthesized in analogy to Example 1 using 5-(4-chlorophenyl)-6-(2,2,2-trifluoroethoxy)-3-pyridinecarboxylic acid (CAN 1018782-82-5) and N-[3-(t-butyl-dimethyl-silanyloxy)-propyl]-N-methyl-hydrazine trifluoroacetate (1:1) as starting materials; the silyl protecting group was lost during reaction and work-up; LC-MS (UV peak area/ESI) 91.5%, 418.1139 (M+H)+.

Example 29

Preparation of 5-(4-chlorophenyl)-N-(3-hydroxyazetidin-1-yl)-6-(2,2,2-trifluoroethoxy)-3-pyridinecarboxamide

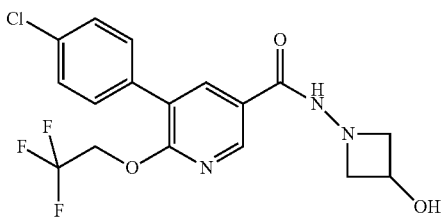 [SMILES: O=C(NN1CC(O)C1)c1cnc(OCC(F)(F)F)c(-c2ccc(Cl)cc2)c1]

a) [3-(t-Butyl-dimethyl-silanyloxy)-azetidin-1-yl]-carbamic acid t-butyl ester

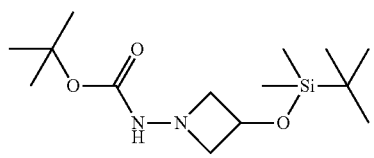

3-[[(1,1-Dimethylethyl)dimethylsilyl]oxy]-azetidine (300 mg, 1.6 mmol) was combined with dichloromethane (16 mL) to give a brown solution. N,N-Diisopropylethylamine (455 mg, 615 µl, 3.52 mmol) was added at 0° C. Subsequently 3-(4-cyanophenyl)-2-oxaziridinecarboxylic acid 1,1-dimethylethyl ester (355 mg, 1.44 mmol) in dichloromethane (10 mL) was added during 25 min at 0° C. and the reaction mixture was stirred for 1 h at 0° C. Afterwards the reaction mixture was concentrated in vacuo and the residue was purified by flash chromatography (silica gel, 20 g, 0% to 40% ethyl acetate in n-heptane) to deliver an oil contaminated with 4-cyano-benzaldehyde. This material was purified by a second chromatography (aminophase 12 g, ethyl acetate/n-heptane 1/1) to give the title compound (320 mg, 67%) as white waxy solid; GC-MS (EI) 302.0 (M)+.

b) 3-(t-Butyl-dimethyl-silanyloxy)-azetidin-1-ylamine trifluoroacetate (1:1)

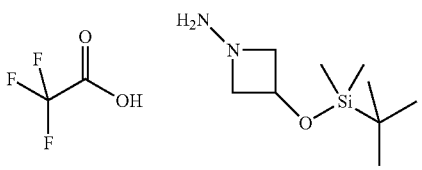

[3-(t-Butyl-dimethyl-silanyloxy)-azetidin-1-yl]-carbamic acid t-butyl ester (100 mg, 331 mmol) was at 0° C. combined with trifluoroacetic acid (2 mL) to give a colorless solution. The reaction mixture was stirred for 2 h at 0° C. and subsequently concentrated in vacuo to give the title compound as colorless oil, which was used without further purification in the next step.

c) 5-(4-Chlorophenyl)-N-(3-hydroxyazetidin-1-yl)-6-(2,2,2-trifluoroethoxy)-3-pyridinecarboxamide The title compound was synthesized in analogy to Example 1 using 5-(4-chlorophenyl)-6-(2,2,2-trifluoroethoxy)-3-pyridinecarboxylic acid (CAN 1018782-82-5) and 3-(t-butyl-dimethyl-silanyloxy)-azetidin-1-ylamine trifluoroacetate (1:1) as starting materials; the silyl protecting group was lost during reaction and work-up; MS (EI) 402.2 (M+H)+.

Example 30

Preparation of 5-cyclopropyl-6-(2,2,2-trifluoroethoxy)-nicotinic acid N'-methyl-N'-phenyl-hydrazide

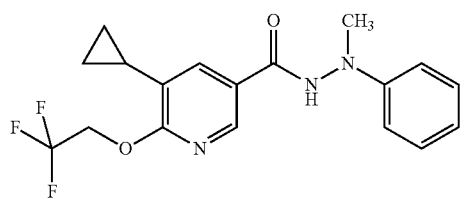 [SMILES: CN(NC(=O)c1cnc(OCC(F)(F)F)c(C2CC2)c1)c1ccccc1]

The title compound was synthesized in analogy to the procedure described in Example 34 c), using 5-cyclopropyl- 6-(2,2,2-trifluoro-ethoxy)-nicotinic acid (example 34b) and N-methyl-N-phenyl-hydrazine (CAN 618-40-6); MS (ESI) 366.2 (M+H)+.

Example 31

Preparation of 5-cyclopropyl-N-(1,1-dioxo-1λ6-thio-morpholin-4-yl)-6-(2,2,2-trifluoro-ethoxy)-nicotinamide

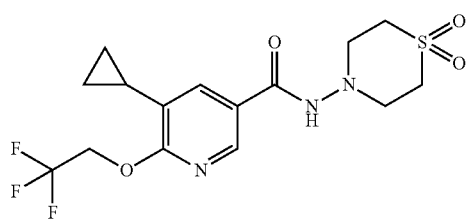 [SMILES: O=C(NN1CCS(=O)(=O)CC1)c1cnc(OCC(F)(F)F)c(C2CC2)c1]

The title compound was synthesized in analogy to the procedure described in Example 34 c), using 5-cyclopropyl-6-(2,2,2-trifluoro-ethoxy)-nicotinic acid (example 34b) and 1,1-dioxo-1λ6-thiomorpholin-4-ylamine as starting materials (CAN 26494-76-8); MS (ESI) 394.4 (M+H)+.

Example 32

Preparation of 5-cyclopropyl-N-morpholin-4-yl-6-(2,2,2-trifluoro-ethoxy)-nicotinamide

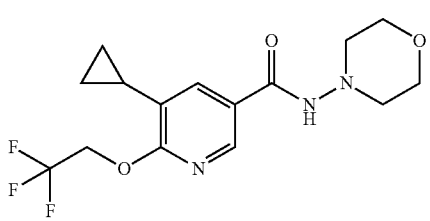 [SMILES: O=C(NN1CCOCC1)c1cnc(OCC(F)(F)F)c(C2CC2)c1]

The title compound was synthesized in analogy to the procedure described in Example 34 c), using 5-cyclopropyl-6-(2,2,2-trifluoro-ethoxy)-nicotinic acid (example 34b) and morpholin-4-ylamine as starting materials (CAN 4319-49-7); MS (ESI) 346.4 (M+H)+.

Example 33

Preparation of 5-cyclopropyl-N—((S)-2-methoxymethyl-pyrrolidin-1-yl)-6-(2,2,2-trifluoro-ethoxy)-nicotinamide

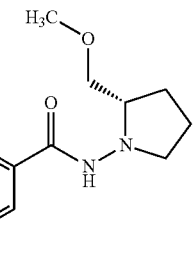

The title compound was synthesized in analogy to the procedure described in Example 34 c), using 5-cyclopropyl-6-(2,2,2-trifluoro-ethoxy)-nicotinic acid (example 34b) and (S)-2-methoxymethyl-pyrrolidin-1-yl amine as starting materials (CAN 59983-39-0); MS (ESI) 396.4 (M+Na)+.

Example 34

Preparation of 5-cyclopropyl-6-(2,2,2-trifluoro-ethoxy)-nicotinic acid N'-(4-fluoro-phenyl)-N'-methyl-hydrazide

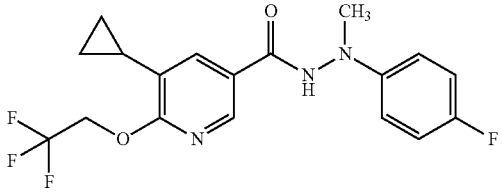 [SMILES: CN(NC(=O)c1cnc(OCC(F)(F)F)c(C2CC2)c1)c1ccc(F)cc1]

a) 5-Cyclopropyl-6-(2,2,2-trifluoro-ethoxy)-nicotinic acid methyl ester

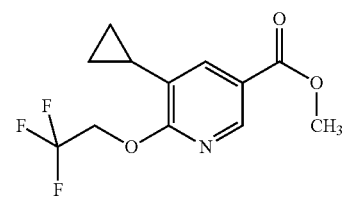 [SMILES: COC(=O)c1cnc(OCC(F)(F)F)c(C2CC2)c1]

In a 50 mL two-necked flask, methyl 5-bromo-6-(2,2,2-trifluoroethoxy)nicotinate (1 g, 3.18 mmol, Eq: 1.00, CAN 1211589-51-3) and cesium carbonate (3.11 g, 9.55 mmol, Eq: 3) were combined with toluene (25 ml) and water (2.8 ml) to give a colorless solution. The reaction mixture was 3× degassed and purged with argon, then palladium(II) acetate (14.3 mg, 63.7 μmol, Eq: 0.02), potassium cyclopropyltrifluoroborate (518 mg, 3.5 mmol, Eq: 1.1) and butyldi-1-adamantylphosphine (68.5 mg, 191 μmol, Eq: 0.06) were successively added and the reaction mixture was heated to 120° C. for 5 h when TLC indicated that the reaction was complete. The mixture was cooled to rt, poured into 50 ml H₂O and extracted with AcOEt (2×50 ml). The organic layers were washed with H₂O/NaCl sol, combined, dried over Na₂SO₄ and concentrated in vacuo. Purification by flash chromatography (silica gel, 70 g, 0% to 20% EtOAc in heptane) yielded eventually 836 mg of the title compound as light yellow semisolid; MS (EI) 276.0 (M+H)⁺.

b) 5-Cyclopropyl-6-(2,2,2-trifluoro-ethoxy)-nicotinic acid

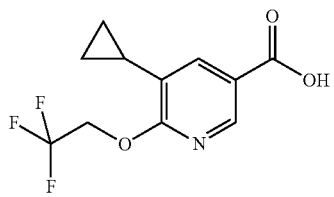 [SMILES: O=C(O)c1cnc(OCC(F)(F)F)c(C2CC2)c1]

In a 25 mL round-bottomed flask, the above prepared 5-cyclopropyl-6-(2,2,2-trifluoro-ethoxy)-nicotinic acid methyl ester (830 mg, 3.02 mmol, Eq: 1.00) was combined with tetrahydrofuran (7 ml) and water (3.5 ml) to give a light yellow bi-phasic system. Lithium hydroxide (86.7 mg, 3.62 mmol, Eq: 1.2) was added and the reaction mixture was stirred vigorously at rt. TLC after ~20 h showed the reaction to be incomplete with some remaining starting material. More lithium hydroxide (43.3 mg, 1.81 mmol, Eq: 0.6) was added and the reaction mixture was stirred at 40° C. TLC after 1 additional h indicated that the reaction was complete. Work up: 10 ml H₂O and 7 ml 1N HCl were added and the reaction mixture was extracted with AcOEt (2×50 ml). The organic layers were washed with H₂O/NaCl sol, combined, dried over Na₂SO₄ and concentrated in vacuo. The residue was triturated with heptane to afford 766 mg of the title compound as white powder; MS (EI) 260.0 (M–H)⁻.

c) 5-Cyclopropyl-6-(2,2,2-trifluoro-ethoxy)-nicotinic acid N'-(4-fluoro-phenyl)-N'-methyl-hydrazide In a 10 mL two-necked flask, the above synthesized 5-cyclopropyl-6-(2,2,2-trifluoroethoxy)nicotinic acid (50 mg, 191 μmol, Eq: 1.00) was combined with tetrahydrofuran (1.00 ml) and DMF (1 ml) to give a colorless solution. TBTU (92.2 mg, 287 μmol, Eq: 1.5) and N,N-diisopropylethylamine (124 mg, 167 μl, 957 μmol, Eq: 5) were added and the reaction mixture was stirred for 10 min at rt; then 1-(4-fluorophenyl)-1-methylhydrazine hydrochloride (40.6 mg, 230 μmol, Eq: 1.2; CAN 1978-54-7) was added and the reaction allowed to proceed over night at rt. The reaction mixture was then quenched with 1 M HCl (10 mL) and extracted with EtOAc (2×20 mL). The organic layers were washed with 1 M NaOH, then with H₂O/NaCl solution. The organic layers were combined, dried over Na₂SO₄ and concentrated in vacuo. Purification by flash chromatography (silica gel, 10 g, 15% to 50% EtOAc in heptane) delivered finally 70 mg of the title product as white semisolid; MS (EI) 384.3 (M+H)⁺.

Example 35

Preparation of 5-(tetrahydro-pyran-4-yl)-6-(2,2,2-trifluoro-ethoxy)-nicotinic acid N'-methyl-N'-phenyl-hydrazide

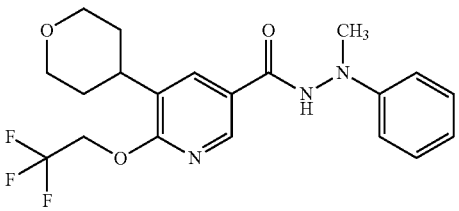 [SMILES: CN(NC(=O)c1cnc(OCC(F)(F)F)c(C2CCOCC2)c1)c1ccccc1]

a) (5-(Tetrahydro-pyran-4-yl)-6-(2,2,2-trifluoro-ethoxy)-nicotinic acid methyl ester

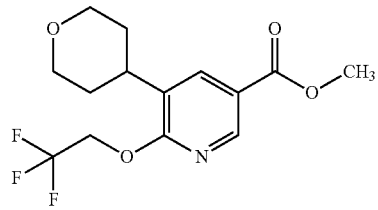 [SMILES: COC(=O)c1cnc(OCC(F)(F)F)c(C2CCOCC2)c1]

Preparation of the zinc iodide reagent:
A 3-neck 25 mL flask connected to another 10 mL flask, a rubber septum, and a 2.3 mm PTFE tubing with a upside down needle covered with a filter disc, was charged with 85 mg Dicalite and dried by heating in vacuo. Afterwards, zinc dust (367 mg) and 3 ml of DMA dried over molecular sieves were added. The mixture was stirred at rt while a 7:5 v/v mixture of chlorotrimethylsilane (66 microliter) and 1,2-dibromoethane (45 microliter) as solution in DMA (1.5 ml) was added at a rate to maintain the temperature below 65° C. (slightly exothermic at the beginning; later a warm water bath was used to increase the temperature to ~45° C.). The resulting slurry was aged for 15 min. A solution of 4-iodotetrahydro-2H-pyran (1 g, 4.72 mmol, Eq: 1.48, CAN 25637-18-7) in 5.5 ml DMA was slowly added to the mixture prepared above at a rate to maintain the temperature below 65° C. (slightly exothermic at the beginning; later a warm water bath was used to increase the temperature to ~40° C.). The resulting reaction mixture was then aged for 30 min at rt. The suspension was filtered through the filter disc under argon to remove all solids.

In a second 25 mL two-necked flask, methyl 5-bromo-6-(2,2,2-trifluoroethoxy)nicotinate (1 g, 3.18 mmol, Eq: 1.00, CAN 1211589-51-3) was combined with DMA (4 mL) to give a colorless solution. Copper (I) iodide (60.6 mg, 318 μmol, Eq: 0.1) and PdCl₂(DPPF)-CH₂Cl₂ adduct (116 mg, 159 μmol, Eq: 0.05) were added. The reaction mixture was 3× degassed and purged with argon, then the above prepared solution containing the organozinc reagent was added (3× degassed and purged with argon) and the reaction mixture was stirred over night at 95° C.

After cooling, the reaction mixture was quenched with sat. NH₄Cl (30 mL) and extracted with EtOAc (2×50 mL). The organic layers were washed with H₂O/NaCl solution. The organic layers were combined, dried over Na₂SO₄, and concentrated in vacuo. The crude material was purified twice by flash chromatography (silica gel, 70 g, 15% to 35% EtOAc in heptane) and (silica gel, 70 g, 100% DCM) to finally afford 545 mg of the title compound as white semisolid; MS (EI) 320.0 (M+H)⁺.

b) 5-(Tetrahydro-pyran-4-yl)-6-(2,2,2-trifluoro-ethoxy)-nicotinic acid

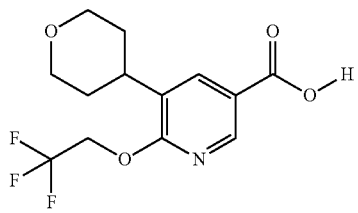 [SMILES: O=C(O)c1cnc(OCC(F)(F)F)c(C2CCOCC2)c1]

In a 25 mL round-bottomed flask, the above prepared 5-(tetrahydro-pyran-4-yl)-6-(2,2,2-trifluoro-ethoxy)-nicotinic acid methyl ester (538 mg, 1.69 mmol, Eq: 1.00) was combined with tetrahydrofuran (4 ml) and water (2 ml) to give a colorless solution. Lithium hydroxide (80.7 mg, 3.37 mmol, Eq: 2) was added and the reaction mixture was stirred at 40° C. TLC after 3 h showed that the reaction was complete. 6 ml H₂O and 4.5 ml 1N HCl were added and the white suspension was stirred for 10 min at 0° C. The solid was filtered off, washed with H2O and dried on hv to yield 489 mg of the title compound as white solid; MS (EI) 304.2 (M−H)⁻.

c) 5-(Tetrahydro-pyran-4-yl)-6-(2,2,2-trifluoro-ethoxy)-nicotinic acid N'-methyl-N'-phenyl-hydrazide In a 10 mL two-necked flask, the above prepared 5-(tetrahydro-pyran-4-yl)-6-(2,2,2-trifluoro-ethoxy)-nicotinic acid (50 mg, 164 µmol, Eq: 1.00) was combined with tetrahydrofuran (1.0 mL) and DMF (1 mL) to give a colorless solution. TBTU (78.9 mg, 246 µmol, Eq: 1.5) and N,N-diisopropylethylamine (106 mg, 143 µl, 819 µmol, Eq: 5) were added and the reaction mixture stirred for 10 min at rt before 1-methyl-1-phenylhydrazine (24.0 mg, 23.1 µl, 197 µmol, Eq: 1.2, CAN 618-40-6) was added and the reaction mixture kept overnight at rt. Work up: The reaction mixture was quenched with 1 M HCl (10 mL) and extracted with EtOAc (2×20 mL). The organic layers were washed with 1 M NaOH, then with H₂O/NaCl sol., the combined organic layers were dried over Na₂SO₄ and concentrated in vacuo. Purification by flash chromatography (silica gel, 10 g, 15% to 50% EtOAc in heptane) delivered eventually 62 mg of the title compound as white foam; MS (EI) 410.2 (M+H)⁺.

Example 36

Preparation of 5-(4-cyano-phenyl)-N-(4-hydroxy-piperidin-1-yl)-6-(2,2,2-trifluoro-ethoxy)-nicotinamide

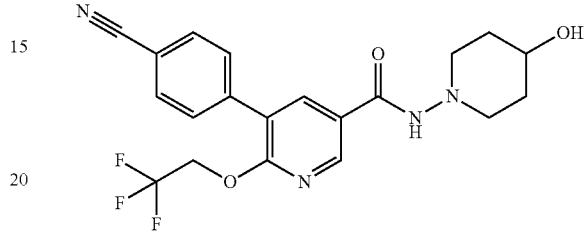

a) 5-(4-Cyano-phenyl)-6-(2,2,2-trifluoro-ethoxy)-nicotinic acid methyl ester

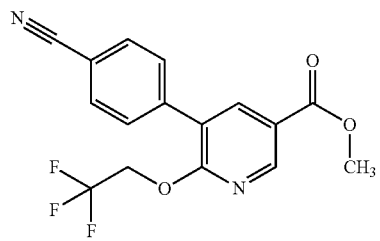 [SMILES: COC(=O)c1cnc(OCC(F)(F)F)c(-c2ccc(C#N)cc2)c1]

In a 50 mL 4-necked flask, methyl 5-bromo-6-(2,2,2-trifluoroethoxy)nicotinate (1 g, 3.18 mmol, Eq: 1.00, CAN 1211589-51-3) and cesium carbonate (3.11 g, 9.55 mmol, Eq: 3) were combined with toluene (25 ml) and water (2.8 ml) to give a colorless solution. The reaction mixture was 3× degassed and purged with argon; then palladium(II) acetate (14.3 mg, 63.7 µmol, Eq: 0.02), potassium (4-cyanophenyl)trifluoroborate (732 mg, 3.5 mmol, Eq: 1.1, CAN 850623-36-8) and butyldi-1-adamantylphosphine (68.5 mg, 191 µmol, Eq: 0.06) were successively added. The degassing-purging cycle was repeated after each addition. The reaction mixture was then heated to 120° C. for 5 hours. After cooling, the reaction mixture was poured into 50 mL H₂O and extracted with AcOEt (2×50 mL). The organic layers were washed with H₂O/NaCl solution, combined, dried over Na₂SO₄ and concentrated in vacuo. Purification by flash chromatography b) 5-(4-Cyano-phenyl)-6-(2,2,2-trifluoro-ethoxy)-nicotinic acid

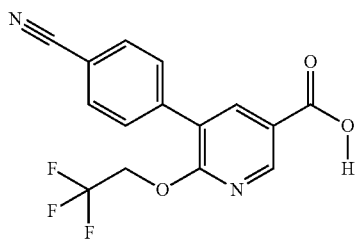 [SMILES: N#Cc1ccc(-c2cc(C(=O)O)cnc2OCC(F)(F)F)cc1]

(silica gel, 50 g, 50% to 100% CH$_2$Cl$_2$ in heptane) yielded finally 898 mg of the title compound as white foam; MS (EI) 337.2 (M+H)$^+$.

In a 25 mL round-bottomed flask, the above prepared 5-(4-cyano-phenyl)-6-(2,2,2-trifluoro-ethoxy)-nicotinic acid methyl ester (0.891 g, 2.65 mmol, Eq: 1.00) was combined with THF (7 mL) and water (3.5 mL) to give a light yellow biphasic system. Lithium hydroxide (127 mg, 5.3 mmol, Eq: 2) was added and the reaction mixture was stirred at 40° C. for 3 hours when TLC indicated the reaction to be complete. Work up: 10 mL H$_2$O and 7 mL HCl 1N were added, the mixture extracted with AcOEt (2×50 mL), the organic layers were combined, washed with brine, dried over Na$_2$SO$_4$ and concentrated in vacuo. Trituration with heptane/EtOAc 9:1 afforded finally 794 mg of the desired title product as a white solid; MS (EI) 321.2 (M–H)$^-$.

c) 5-(4-Cyano-phenyl)-N-(4-hydroxy-piperidin-1-yl)-6-(2,2,2-trifluoro-ethoxy)-nicotinamide In a 5 mL round-bottomed flask, the above prepared 5-(4-cyano-phenyl)-6-(2,2,2-trifluoro-ethoxy)-nicotinic acid (0.050 g, 155 µmol, Eq: 1.00) was combined with THF (1 mL) and DMF (1 mL) to give a colorless solution. TBTU (74.7 mg, 233 µmol, Eq: 1.5) and N,N-diisopropyl-ethylamine (100 mg, 135 µL, 776 µmol, Eq: 5) were added. The reaction mixture was stirred for 10 min at RT, then 1-aminopiperidin-4-ol (21.6 mg, 186 µmol, Eq: 1.2, CAN 79414-82-7) was added and the reaction mixture kept at RT overnight. Pouring into 25 mL 1 M HCl, extraction with EtOAc (2×50 mL), washing with 1 M NaOH, drying over Na$_2$SO$_4$ and evaporation of all solvents in vacuo, followed by stirring for 15 min with 3 mL of heptane containing 3 drops of EtOAc, generated 51 mg of the title compound as white solid; MS (EI) 421.1 (M+H)$^+$.

Example 37

Preparation of 5-(4-cyano-phenyl)-N-morpholin-4-yl-6-(2,2,2-trifluoro-ethoxy)-nicotinamide

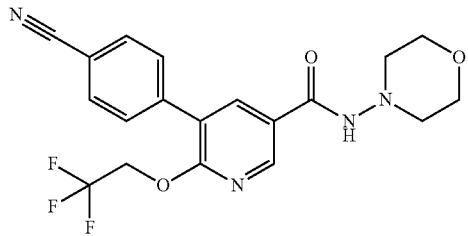 [SMILES: N#Cc1ccc(-c2cc(C(=O)NN3CCOCC3)cnc2OCC(F)(F)F)cc1]

The title compound was synthesized in analogy to Example 36, but using in the last step morpholin-4-ylamine (CAN 4319-49-7) as coupling partner, as white solid; MS (EI) 407.2 (M+H)$^+$.

Example 38

Preparation of 5-(4-cyano-phenyl)-N-[4-(2-hydroxy-ethyl)-piperidin-1-yl]-6-(2,2,2-trifluoro-ethoxy)-nicotinamide

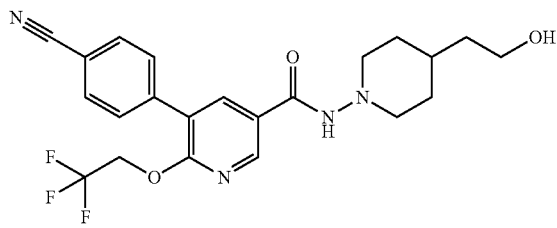 [SMILES: N#Cc1ccc(-c2cc(C(=O)NN3CCC(CCO)CC3)cnc2OCC(F)(F)F)cc1]

The title compound was synthesized in analogy to Example 36, but using in the last step 2-(1-mino-piperidin-4-yl)-ethanol as coupling partner, as white solid; MS (EI) 449.2 (M+H)$^+$. The latter reagent was prepared as follows:

A 50 mL four-necked flask was charged with sodium hypochlorite solution (8.44 g, 7.00 mL, 15.5 mmol, Eq: 4) and the solution was cooled to –10° C. Maintaining this temperature, ammonium hydroxide 25% NH$_3$ (949 mg, 1.05 ml, 13.9 mmol, Eq: 3.6) and ammonium chloride 1M (11.6 mL, 11.6 mmol, Eq: 3) were added simultaneously. After 5 min, 2-(piperidin-4-yl)ethanol (500 mg, 3.87 mmol, Eq: 1.00, CAN 622-26-4) in 2 mL THF and sodium hydroxide (2.58 g, 1.94 mL, 19.3 mmol, Eq: 5) were added simultaneously at the same temperature as before, and the reaction allowed to proceed for another 2 hours at rt. The mixture was diluted with H$_2$O and extracted with EtOAc (2×10 mL). The aqueous layer was concentrated in vacuo and the residue taken up in CH$_2$Cl$_2$, dried over Na$_2$SO$_4$, filtered and concentrated in vacuo. Thereby, 340 mg of 2-(1-mino-piperidin-4-yl)-ethanol were obtained as white semi-solid; MS (EI) 145.2 (M+H)⁺.

Example 39

Preparation of 5-[4-(2-hydroxy-ethyl)-piperidin-1-ylcarbamoyl]-2-(2,2,2-trifluoro-ethoxy)-3',4',5',6'-tetrahydro-2'H-[3,4']bipyridinyl-1'-carboxylic acid tert-butyl ester

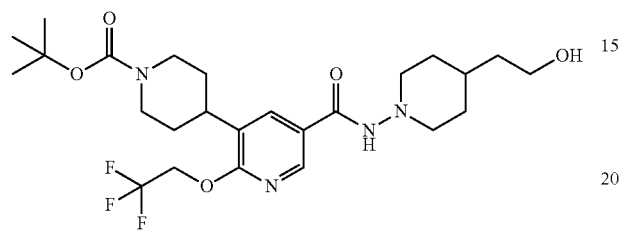

a) 2-(2,2,2-Trifluoro-ethoxy)-3',4',5',6'-tetrahydro-2'H-[3,4]bipyridinyl-5,1'-dicarboxylic acid 1'-tert-butyl ester 5-methyl ester

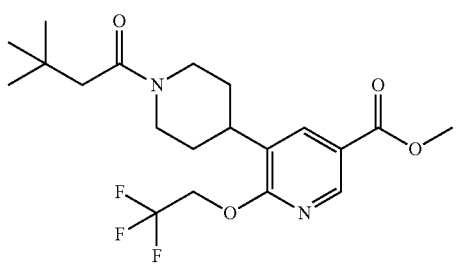 [SMILES: COC(=O)c1cnc(OCC(F)(F)F)c(C2CCN(C(=O)CC(C)(C)C)CC2)c1]

Preparation of the zinc iodide reagent:
In a dried 25 mL three-necked flask, zinc (495 mg, 7.57 mmol, Eq: 2.38) was combined with 3 ml DMA (over molecular sieve) to give a grey suspension. The mixture was stirred at rt while a 7:5 v/v mixture of chlorotrimethylsilane (89 microliter) and 1,2-dibromoethane (61 microliter) as solution in DMA (1.5 mL) was added at a rate to maintain the temperature below 65° C. (slightly exothermic at the beginning, afterwards a warm water bath was used to increase the temperature to ~45° C.). The resulting slurry was aged for 15 min. A solution of tert-butyl 4-iodopiperidine-1-carboxylate (1.98 g, 6.37 mmol, Eq: 2, CAN 301673-14-3) in 5.5 ml DMA was slowly added to the mixture at such a rate to maintain the temperature below 45° C. (slightly exothermic at the beginning, afterwards a warm water bath was used to increase the temperature to ~40° C.). The resulting reaction mixture was then kept for 30 min at rt. and the solids were finally allowed to settle for 15 min without stirring for decantation.

In a second 25 mL two-necked flask, methyl 5-bromo-6-(2,2,2-trifluoroethoxy)nicotinate (1 g, 3.18 mmol, Eq: 1.00, CAN 1211589-51-3) was combined with DMA (4 mL) to give a colorless solution. Copper (I) iodide (60.6 mg, 318 µmol, Eq: 0.1) and PdCl₂(DPPF)-CH₂Cl₂ adduct (116 mg, 159 µmol, Eq: 0.05) were added. The reaction mixture was 3× degassed and purged with argon, the above prepared solution containing the organozinc-reagent was added (3× degassed and purged with argon), and the reaction mixture was stirred over night at 87° C. After cooling, the reaction mixture was quenched with sat. NH₄Cl (30 mL) and extracted with TBME (2×50 mL). The organic layers were washed with H₂O/NaCl solution. The organic layers were combined, dried over Na₂SO₄, and concentrated in vacuo. The crude material was purified by flash chromatography (silica gel, 150 g, AcOEt-Hept:1-3) to finally afford 1.26 g of the title compound as light yellow semisolid; MS (EI) 363.4 (M+H-tBu)⁺.

b) 2-(2,2,2-Trifluoro-ethoxy)-3',4',5',6'-tetrahydro-2'H-[3,4]bipyridinyl-5,1'-dicarboxylic acid 1'-tert-butyl ester

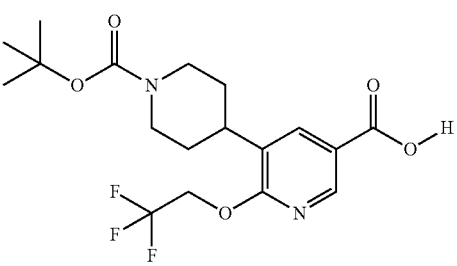 [SMILES: CC(C)(C)OC(=O)N1CCC(c2cc(C(=O)O)cnc2OCC(F)(F)F)CC1]

In a 25 mL round-bottomed flask, the above prepared 2-(2,2,2-trifluoro-ethoxy)-3',4',5',6'-tetrahydro-2'H-[3,4]bipyridinyl-5,1'-dicarboxylic acid 1'-tert-butyl ester 5-methyl ester (1.266 g, 2.42 mmol, Eq: 1.00) was combined with tetrahydrofuran (7 mL) and water (3.5 mL) to give a colorless solution. Lithium hydroxide (145 mg, 6.05 mmol, Eq: 2.5) was added and the reaction mixture was stirred at 40° C. for 3 h when TLC indicated the absence of starting material. Work up: 10 mL H₂O and 10 mL sat NH₄Cl were added and the reaction mixture was extracted with AcOEt (2×50 ml). The organic layers were washed with H₂O/NaCl solution, combined, dried over Na₂SO₄ and concentrated in vacuo. Crystallization from EtOAc and heptane afforded 800 mg of the title compound as white solid; MS (EI) 403.6 (M−H)⁻.

c) 5-[4-(2-hydroxy-ethyl)-piperidin-1-ylcarbamoyl]-2-(2,2,2-trifluoro-ethoxy)-3',4',5',6'-tetrahydro-2'H-[3,4']bipyridinyl-1'-carboxylic acid tert-butyl ester In a 10 mL round-bottomed flask, the above prepared 2-(2,2,2-trifluoro-ethoxy)-3',4',5',6'-tetrahydro-2'H-[3,4']bipyridinyl-5,1'-dicarboxylic acid 1'-tert-butyl ester (100 mg, 247 mmol, Eq: 1.00) was combined with tetrahydrofuran (3 mL) and DMF (1 mL) to give a colorless solution. TBTU (119 mg, 371 µmol, Eq: 1.5) and N,N-diisopropylethylamine (160 mg, 216 µl, 1.24 mmol, Eq: 5) were added and the reaction mixture was stirred for 10 min at rt before 2-(1-aminopiperidin-4-yl)ethanol (61.1 mg, 297 µmol, Eq: 1.2, preparation see Example 38) was added and the reaction mixture kept overnight at rt. The reaction mixture was then quenched with sat NH₄Cl sol. 10 mL and extracted with EtOAc (2×20 mL). The organic layers were washed with 1 M NaOH, then with H₂O/NaCl sol., combined, dried over Na₂SO₄ and concentrated in vacuo. Purification by flash chromatography (silica gel, 20 g, 2% to 5% MeOH in DCM) delivered eventually 101 mg of the title compound as white foam; MS (EI) 531.6 (M+H)+.

Example 40

Preparation of 5-[N'-(4-fluoro-phenyl)-N'-methyl-hydrazinocarbonyl]-2-(2,2,2-trifluoro-ethoxy)-3',4',5',6'-tetrahydro-2'H-[3,4']bipyridinyl-1'-carboxylic acid tert-butyl ester

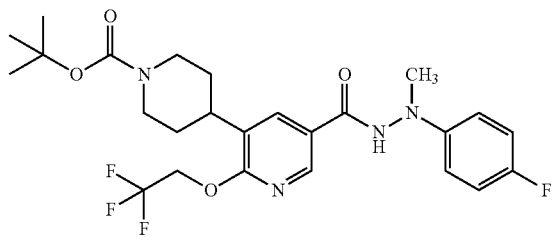 [SMILES: CN(NC(=O)c1cnc(OCC(F)(F)F)c(C2CCN(C(=O)OC(C)(C)C)CC2)c1)c1ccc(F)cc1]

The title compound was synthesized in analogy to Example 39, but using in the last step N-(4-fluoro-phenyl)-N-methyl-hydrazine (CAN 1978-54-7) as coupling partner, as white solid; MS (EI) 525.7 (M–H)−.

Example 41

Preparation of 5-cyclopropyl-6-cyclopropylmethoxy-nicotinic acid N'-(4-fluoro-phenyl)-N'-methyl-hydrazide

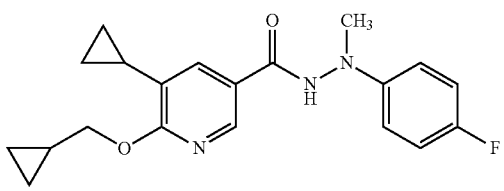 [SMILES: CN(NC(=O)c1cnc(OCC2CC2)c(C2CC2)c1)c1ccc(F)cc1]

a) 5-Cyclopropyl-6-cyclopropylmethoxy-nicotinic acid

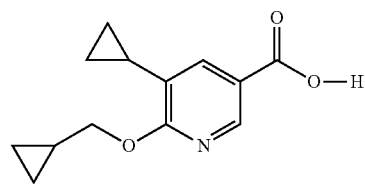 [SMILES: O=C(O)c1cnc(OCC2CC2)c(C2CC2)c1]

In a 50 mL two-necked flask, 5-bromo-6-(cyclopropylmethoxy)nicotinic acid (1 g, 3.68 mmol, Eq: 1.00, CAN 912454-38-7) and cesium carbonate (3.59 g, 11.0 mmol, Eq: 3) were combined with toluene (25 mL) and water (2.8 mL) to give a colorless solution. The reaction mixture was 3× degassed and purged with argon, then palladium(II) acetate (16.5 mg, 73.5 μmol, Eq: 0.02), potassium cyclopropyltrifluoroborate (598 mg, 4.04 mmol, Eq: 1.1) and butyldi-1-adamantylphosphine (79.1 mg, 221 μmol, Eq: 0.06) were successively added. The evacuating-purging cycle was repeated after each addition. The reaction mixture was then heated to 120° C. for 4 h when TLC indicated the presence of some remaining starting material. The same amount of palladium acetate and phosphine ligand was once more added, and the reaction allowed proceeding over night at 120° C. The mixture was cooled to rt, poured into 20 mL 1N NaOH and extracted with $CH_2Cl_2$ (2×20 mL). The aqueous layer was acidified with 30 mL 2N HCl and extracted with AcOEt (2×50 ml). The organic layers were washed with $H_2O/NaCl$ solution, combined, dried over $Na_2SO_4$ and concentrated in vacuo. Crystallization from AcOEt/heptane finally yielded 609 mg of the title compound as off-white solid; MS (EI) 232.6 (M–H)−.

b) 5-Cyclopropyl-6-cyclopropylmethoxy-nicotinic acid N'-(4-fluoro-phenyl)-N'-methyl-hydrazide In a 10 mL two-necked flask, the above prepared 5-cyclopropyl-6-cyclopropylmethoxy-nicotinic acid (70 mg, 300 μmol, Eq: 1.00) was combined with tetrahydrofuran (3 mL) and DMF (1 mL) to give a colorless solution. TBTU (145 mg, 450 μmol, Eq: 1.5) and N,N-diisopropylethylamine (194 mg, 262 μl, 1.5 mmol, Eq: 5) were added and the reaction mixture stirred for 10 min at rt, before 1-(4-fluorophenyl)-1-methylhydrazine hydrochloride (63.6 mg, 360 μmol, Eq: 1.2, CAN 1978-54-7) was added and the reaction mixture kept overnight at rt. The reaction mixture was quenched with 1 M HCl (10 mL) and extracted with EtOAc (2×20 mL). The organic layers were washed with 1 M NaOH, then with $H_2O/NaCl$ solution, combined, dried over $Na_2SO_4$ and concentrated in vacuo. The crude material was eventually purified by flash chromatography (silica gel, 20 g, 15% to 40% EtOAc in heptane) to provide 104 mg of the title product as colorless oil; MS (EI) 354.6 (M–H)−.

Example 42

Preparation of 5-cyclopropyl-6-cyclopropylmethoxy-nicotinic acid N'-(4-fluoro-phenyl)-N'-methyl-hydrazide

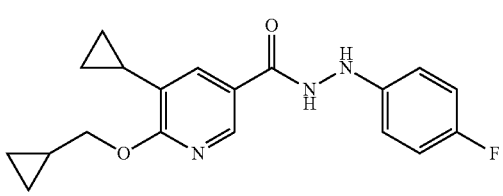 [SMILES: O=C(NNc1ccc(F)cc1)c1cnc(OCC2CC2)c(C2CC2)c1]

The title compound was synthesized in analogy to Example 41, but using in the final step (4-fluoro-phenyl)-

Example 43

Preparation of 5-cyclopropyl-6-cyclopropylmethoxy-nicotinic acid N'-methyl-N'-phenyl-hydrazide

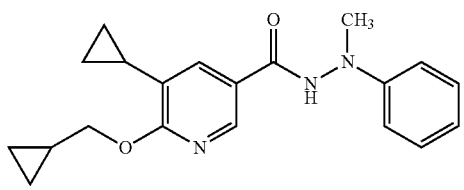 [SMILES: CN(NC(=O)c1cnc(OCC2CC2)c(C2CC2)c1)c1ccccc1]

The title compound was synthesized in analogy to Example 41, but using in the final step N-methyl-N-phenyl-hydrazine (CAN 618-40-6) as coupling partner, as colorless oil; MS (EI) 336.6 (M−H)⁻.

Example 44

Preparation of 5-cyclopropyl-N-((2R,6S)-2,6-dimethyl-morpholin-4-yl)-6-(2,2,2-trifluoro-ethoxy)-nicotinamide

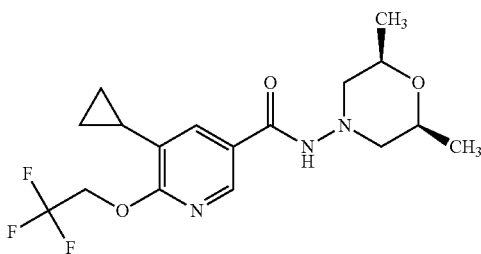 [SMILES: C[C@@H]1CN(NC(=O)c2cnc(OCC(F)(F)F)c(C3CC3)c2)C[C@H](C)O1]

The title compound was synthesized in analogy to Example 34, but using in the final step (2R,6S)-2,6-dimethyl-morpholin-4-ylamine as coupling partner, as white semisolid; MS (EI) 374.5 (M+H)⁺.

The necessary (2R,6S)-2,6-dimethyl-morpholin-4-ylamine was synthesized as follows: A 50 mL four-necked flask was charged with sodium hypochlorite solution (9.47 g, 7.85 mL, 17.4 mmol, Eq: 4) and the solution was cooled to −10° C. At the same temperature, ammonium chloride 5M in H$_2$O (2.6 mL, 13.0 mmol, Eq: 3) and ammonium hydroxide 25% NH$_3$ (1.06 g, 1.18 mL, 15.6 mmol, Eq: 3.6) were added simultaneously at a temperature range of −7 to −12° C. After 5 min, cis-2,6-dimethylmorpholine (500 mg, 4.34 mmol, Eq: 1.00) in 2 mL THF and sodium hydroxide (2.89 g, 2.18 mL, 21.7 mmol, Eq: 5) were added simultaneously at the same temperature as before and the mixture stirred for another 2 hours at rt. The crude mixture was extracted with 15 mL TBME to remove an impurity and then with 5×50 mL CH$_2$Cl$_2$. The latter organic layer was dried over Na$_2$SO$_4$, concentrated in vacuo and briefly dried on hv to afford 268 mg of the title compound as colorless liquid; MS (EI) 131.1 (M+H)⁺.

Example 45

Preparation of 5-cyclopropyl-6-cyclopropylmethoxy-N-((2R,6S)-2,6-dimethyl-morpholin-4-yl)-nicotinamide

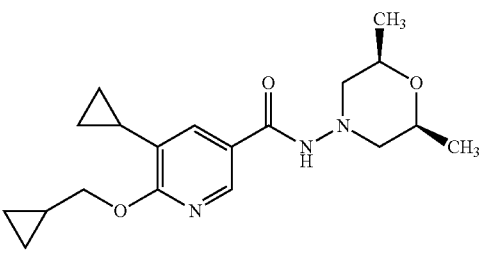 [SMILES: C[C@@H]1CN(NC(=O)c2cnc(OCC3CC3)c(C3CC3)c2)C[C@H](C)O1]

The title compound was synthesized in analogy to Example 41, but using in the final step (2R,6S)-2,6-dimethyl-morpholin-4-ylamine (preparation see Example 44) as coupling partner, as white semisolid; MS (D) 346.5 (M+H)⁺.

Example 46

Preparation of 5-cyclopropyl-6-(2,2,2-trifluoro-ethoxy)-nicotinic acid N'-pyridin-4-ylmethyl-hydrazide

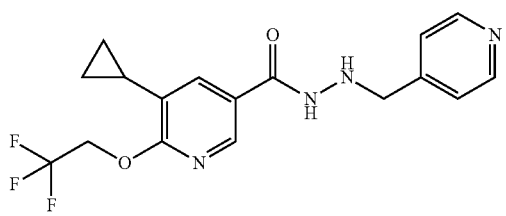 [SMILES: O=C(NNCc1ccncc1)c1cnc(OCC(F)(F)F)c(C2CC2)c1]

The title compound was synthesized in analogy to Example 34, but using in the final step pyridin-4-ylmethyl-hydrazine (CAN 7112-39-2) as coupling partner, as colorless oil; MS (EI) 367.4 (M+H)⁺.

Example 47

Preparation of 6-cyclobutoxy-5-cyclopropyl-nicotinic acid N'-(4-fluoro-phenyl)-N'-methyl-hydrazide

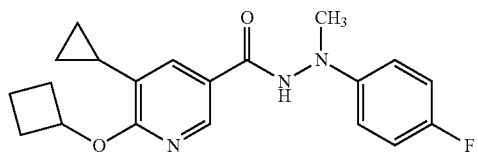 [SMILES: CN(NC(=O)c1cnc(OC2CCC2)c(C2CC2)c1)c1ccc(F)cc1]

The title compound was synthesized in analogy to Example 41, but starting the reaction sequence with 5-bromo-6-cyclobutoxy-nicotinic acid instead of 5-bromo-6-(cyclopropylmethoxy)-nicotinic acid, as white foam; MS (EI) 356.4 (M+H)⁺.

The former reagent was synthesized as follows:
In a 250 mL pear-shaped flask, 5-bromo-6-chloronicotinic acid (5 g, 21.1 mmol, Eq: 1.00) was combined with DMSO (75 mL) to give a colorless solution. Potassium hydroxide (3.56 g, 63.4 mmol, Eq: 3) powdered and cyclobutanol (1.98 g, 2.15 ml, 27.5 mmol, Eq: 1.3) were added and the reaction mixture was stirred at RT overnight (->yellow solution). TLC indicated the reaction to be complete. The mixture was diluted with 75 ml H₂O, cooled to 0-5° C., and neutralized with 8 ml 25% HCl (slowly added dropwise under stirring whereupon a white solid formed). The solid was filtered off, washed with 2×20 mL H2O and dried overnight on HV; thereby, 5.26 g of 5-bromo-6-cyclobutoxy-nicotinic acid was obtained as white solid; MS (EI) 272.2, 274.2 (M+H)⁺.

Example 48

Preparation of 6-cyclobutoxy-5-furan-2-yl-nicotinic acid N'-(4-fluoro-phenyl)-hydrazide

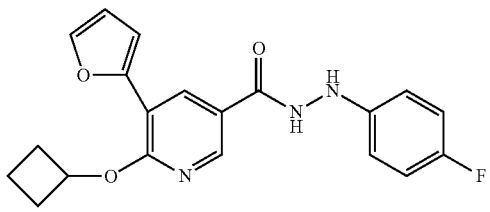 [SMILES: O=C(NNc1ccc(F)cc1)c1cnc(OC2CCC2)c(-c2ccco2)c1]

a) 6-Cyclobutoxy-5-furan-2-yl-nicotinic acid

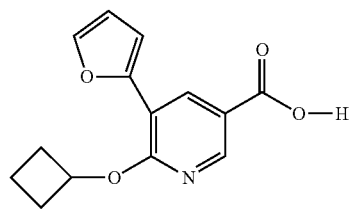 [SMILES: O=C(O)c1cnc(OC2CCC2)c(-c2ccco2)c1]

In a 50 mL 4-necked flask, 5-bromo-6-cyclobutoxynicotinic acid (1 g, 3.68 mmol, Eq: 1.00, preparation see Example 47) and cesium carbonate (3.59 g, 11.0 mmol, Eq: 3) were combined with toluene (25 mL) and water (2.8 mL) to give a colorless solution. The reaction mixture was 3× degassed and purged with argon before successively potassium 2-furantrifluoroborate (959 mg, 5.51 mmol, Eq: 1.5), palladium(II) acetate (41.3 mg, 184 μmol, Eq: 0.05) and butyldi-1-adamantylphosphine (198 mg, 551 μmol, Eq: 0.15) were added. The evacuating-purging cycle was repeated after each addition. The reaction mixture was then heated to 120° C. for 5 hours when TLC showed that the starting material had disappeared. Work up: The reaction mixture was cooled to RT, poured into 30 mL 1N HCl and extracted with AcOEt/THF 2:1 (4×50 mL). The organic layers were combined, washed with brine, dried over Na₂SO₄ and concentrated in vacuo. The crude material was then purified by triturating it with methanol to afford 713 mg of the title compound as yellow solid; MS (EI) 258.4 (M–H)⁻.

b) 6-Cyclobutoxy-5-furan-2-yl-nicotinic acid N'-(4-fluoro-phenyl)-hydrazide

In a 5 mL round-bottomed flask the above prepared 6-cyclobutoxy-5-furan-2-yl-nicotinic acid (0.050 g, 174 μmol, Eq: 1.00) was combined with THF (2 mL) to give a colorless solution. TBTU (83.6 mg, 260 μmol, Eq: 1.5) and N,N-diisopropylamine (112 mg, 152 μL, 868 μmol, Eq: 5) were added. The reaction mixture was stirred for 10 min at RT before (4-fluorophenyl)-hydrazine hydrochloride (33.9 mg, 208 μmol, Eq: 1.2) was added and the reaction allowed to proceed at RT overnight. The mixture was poured into 15 mL 1 M HCl and extracted with EtOAc (2×25 mL). The organic layers were combined, washed with 1 M NaOH, dried over Na₂SO₄ and concentrated in vacuo. The crude material was purified by flash chromatography (silica gel, 10 g, 15% to 50% EtOAc in heptane) to yield 40 mg of the title compound as white solid; MS (EI) 368.4 (M+H)⁺.

Example 49

Preparation of 5-cyclopropyl-6-(2,2,2-trifluoroethoxy)-nicotinic acid N'-methyl-N'-pyridin-4-yl-hydrazide

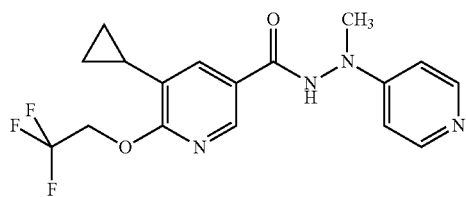 [SMILES: CN(NC(=O)c1cnc(OCC(F)(F)F)c(C2CC2)c1)c1ccncc1]

The title compound was synthesized in analogy to Example 34, but using in the final step N-methyl-N-pyridin-4-yl-hydrazine (CAS 76890-04-5) as coupling partner, as white crystalline solid; MS (EI) 367.1 (M+H)⁺.

Example 50

Preparation of 6-cyclobutoxy-5-furan-2-yl-N-(4-hydroxy-piperidin-1-yl)-nicotinamide

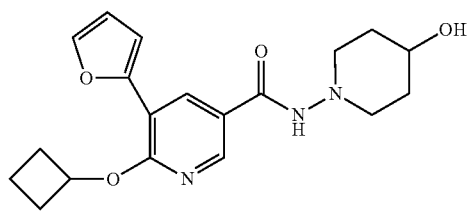 [SMILES: O=C(NN1CCC(O)CC1)c1cnc(OC2CCC2)c(-c2ccco2)c1]

The title compound was synthesized in analogy to Example 48, but using in the final step 1-amino-piperidin-4- ol (CAN 79414-82-7) as coupling partner, as light yellow solid; MS (EI) 356.5 (M–H)⁻.

Example 51

Preparation of 6-cyclobutoxy-5-furan-2-yl-nicotinic acid N'-(6-chloro-pyridazin-3-yl)-N'-methyl-hydrazide

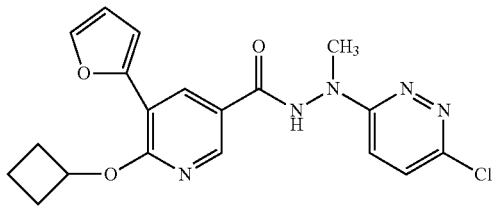 [SMILES: CN(NC(=O)c1cnc(OC2CCC2)c(-c2ccco2)c1)c1ccc(Cl)nn1]

The title compound was synthesized in analogy to Example 48, but using in the final step N-(6-chloro-pyridazin-3-yl)-N-methyl-hydrazine (CAN 76953-33-8) as coupling partner, as yellow solid; MS (EI) 398.5, 400.4 (M–H)⁻.

Example 52

Preparation of 6-cyclobutoxy-5-furan-2-yl-nicotinic acid N'-methyl-N'-pyridin-4-yl-hydrazide

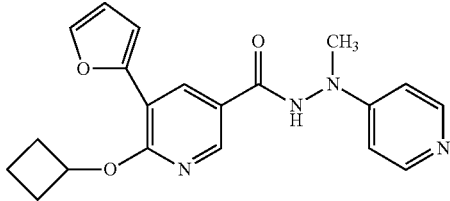 [SMILES: CN(NC(=O)c1cnc(OC2CCC2)c(-c2ccco2)c1)c1ccncc1]

The title compound was synthesized in analogy to Example 48, but using in the final step N-Methyl-N-pyridin-4-yl-hydrazine (CAN 76890-04-5) as coupling partner, as light yellow solid; MS (EI) 363.5 (M–H)⁻.

Example 53

Preparation of 5-cyclopropyl-6-cyclopropylmethoxy-nicotinic acid N'-(4-cyano-phenyl)-N'-methyl-hydrazide

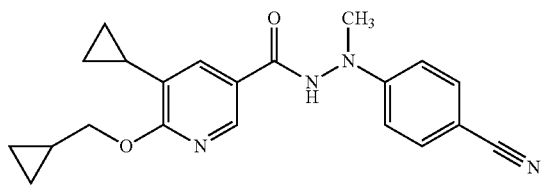 [SMILES: CN(NC(=O)c1cnc(OCC2CC2)c(C2CC2)c1)c1ccc(C#N)cc1]

The title compound was synthesized in analogy to Example 41, but using in the final step 4-(N-methyl-hydrazino)-benzonitrile (CAN 79121-28-1) as coupling partner, as colorless solid; MS (EI) 363.4 (M+H)⁺.

Example 54

Preparation of 5-cyclopropyl-6-(2,2,2-trifluoro-ethoxy)-nicotinic acid N'-(4-cyano-phenyl)-N'-methyl-hydrazide

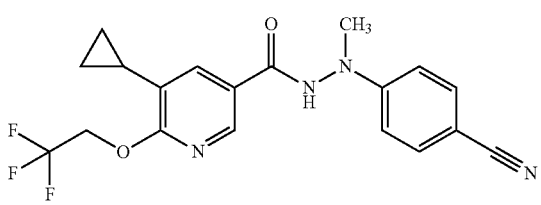 [SMILES: CN(NC(=O)c1cnc(OCC(F)(F)F)c(C2CC2)c1)c1ccc(C#N)cc1]

The title compound was synthesized in analogy to Example 34, but using in the final step 4-(N-methyl-hydrazino)-benzonitrile (CAN 79121-28-1) as coupling partner, as white foam; MS (EI) 389.6 (M–H)⁻.

Example 55

Preparation of 6-cyclobutoxy-5-cyclopropyl-nicotinic acid N'-(4-cyano-phenyl)-N'-methyl-hydrazide

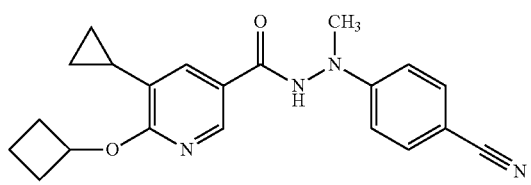 [SMILES: CN(NC(=O)c1cnc(OC2CCC2)c(C2CC2)c1)c1ccc(C#N)cc1]

The title compound was synthesized in analogy to Example 47, but using in the final step 4-(N-methyl-hydrazino)-benzonitrile (CAN 79121-28-1) as coupling partner, as white foam; MS (EI) 363.4 (M+H)⁺.

Example 56

Preparation of 5-(3-fluoro-phenyl)-6-(2,2,2-trifluoro-ethoxy)-nicotinic acid N'-methyl-N'-phenyl-hydrazide

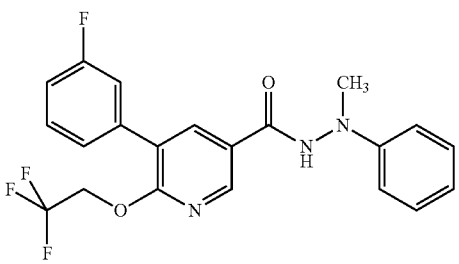 [SMILES: CN(NC(=O)c1cnc(OCC(F)(F)F)c(-c2cccc(F)c2)c1)c1ccccc1]

The title compound was synthesized in analogy to Example 34, but using in the first step potassium (3-fluorophenyl)trifluoroborate as Suzuki reagent and in the final N-methyl-N-phenyl-hydrazine (CAN 618-40-6) as coupling partner, as white solid; MS (EI) 420.4 (M+H)⁺.

The invention claimed is:
1. The compound according to formula I,

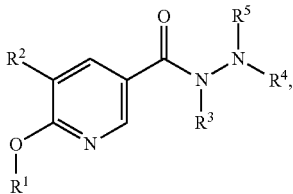

wherein
$R^1$ is selected from the group consisting of
$C_{3-7}$-cycloalkyl,
$C_{3-7}$-cycloalkyl-$C_{1-7}$-alkyl,
and
halogen-$C_{1-7}$-alkyl;
$R^2$ is selected from the group consisting of
phenyl, said phenyl being unsubstituted or substituted by one, two or three groups selected from the group consisting of $C_{1-7}$-alkyl, $C_{1-7}$-alkoxy, halogen, halogen-$C_{1-7}$-alkyl, halogen-$C_{1-7}$-alkoxy, amino, azido and cyano,
$C_{3-7}$-cycloalkyl,
furyl, and
heterocyclyl, said heterocyclyl having 3 to 7 ring atoms, comprising one, two or three heteroatoms selected from N, O and S and being unsubstituted or substituted by a $C_{1-7}$-alkoxycarbonyl group;
$R^3$ is hydrogen;
$R^4$ is hydrogen or $C_{1-7}$-alkyl;
or $R^3$ and $R^4$ are —(CH$_2$)$_3$— and together with the nitrogen atoms to which they are attached form a 5-membered heterocyclic ring; and
$R^5$ is selected from the group consisting of hydrogen,
halogen-$C_{1-7}$-alkyl, hydroxyl-$C_{1-7}$-alkyl, $C_{1-7}$-alkoxycarbonyl,
phenyl, said phenyl being unsubstituted or substituted by one, two or three groups selected from the group consisting of $C_{1-7}$-alkyl, halogen, halogen-$C_{1-7}$-alkyl and cyano,
heteroaryl, said heteroaryl being unsubstituted or substituted by one or two groups selected from the group consisting of $C_{1-7}$-alkyl, halogen and halogen-$C_{1-7}$-alkyl; and
heteroaryl-$C_{1-7}$-alkyl, said heteroaryl-$C_{1-7}$-alkyl being unsubstituted or substituted by one or two groups selected from the group consisting of $C_{1-7}$-alkyl, halogen and halogen-$C_{1-7}$-alkyl;
or $R^4$ and $R^5$ together with the nitrogen atom to which they are attached form a 4-, 5-, 6- or 7-membered heterocyclic ring optionally containing a further heteroatom or group selected from nitrogen, oxygen, sulfur, sulfinyl and sulfonyl,
said heterocyclic ring being unsubstituted or substituted by one, two or three groups independently selected from $C_{1-7}$-alkyl, hydroxy, oxo, hydroxy-$C_{1-7}$-alkyl, $C_{1-7}$-alkoxy, $C_{1-7}$-alkoxy-$C_{1-7}$-alkyl, heterocyclyl-$C_{1-7}$-alkyl, $C_{1-7}$-alkylcarbonyl and $C_{1-7}$-alkylsulfonyl;
or a pharmaceutically acceptable salt thereof.
2. The compound according to claim 1, wherein $R^2$ is phenyl, said phenyl being unsubstituted or substituted by one, two or three groups selected from the group consisting of hydrogen, $C_{1-7}$-alkyl, $C_{1-7}$-alkoxy, halogen, halogen-$C_{1-7}$-alkyl, halogen-$C_{1-7}$-alkoxy, amino, azido and cyano, or $R^2$ is $C_{3-7}$-cycloalkyl.
3. The compound according to claim 1, wherein $R^2$ is phenyl, said phenyl being unsubstituted or substituted by one, two or three groups selected from the group consisting of hydrogen, $C_{1-7}$-alkyl, $C_{1-7}$-alkoxy, halogen, halogen-$C_{1-7}$-alkyl, halogen-$C_{1-7}$-alkoxy, amino, azido and cyano.
4. The compound according to claim 1, wherein $R^2$ is $C_{3-7}$-cycloalkyl.
5. The compound according to claim 1, wherein $R^2$ is heterocyclyl, said heterocyclyl having 3 to 7 ring atoms, comprising one, two or three heteroatoms selected from N, O and S and being unsubstituted or substituted by a $C_{1-7}$-alkoxycarbonyl group.
6. The compound according to claim 1, wherein $R^4$ and $R^5$ together with the nitrogen atom to which they are attached form a 4-, 5-, 6- or 7-membered heterocyclic ring optionally containing a further heteroatom or group selected from nitrogen, oxygen, sulfur, sulfinyl and sulfonyl, said heterocyclic ring being unsubstituted or substituted by one, two or three groups independently selected from $C_{1-7}$-alkyl, hydroxy, oxo, hydroxy-$C_{1-7}$-alkyl, $C_{1-7}$-alkoxy, $C_{1-7}$-alkoxy-$C_{1-7}$-alkyl, heterocyclyl-$C_{1-7}$-alkyl, $C_{1-7}$-alkylcarbonyl and $C_{1-7}$-alkylsulfonyl.
7. The compound according to claim 1, wherein $R^4$ and $R^5$ together with the nitrogen atom to which they are attached form a heterocyclic ring selected from the group consisting of azetidinyl, pyrrolidinyl, oxazolidinyl, piperidinyl, piperazinyl, morpholinyl and 1,1-dioxido-4-thiomorpholinyl, said heterocyclic ring being unsubstituted or substituted by one, two or three groups independently selected from $C_{1-7}$-alkyl, hydroxy, oxo, hydroxy-$C_{1-7}$-alkyl, $C_{1-7}$-alkoxy, $C_{1-7}$-alkoxy-$C_{1-7}$-alkyl, heterocyclyl-$C_{1-7}$-alkyl, $C_{1-7}$-alkylcarbonyl and $C_{1-7}$-alkylsulfonyl.
8. The compound according to claim 1, wherein $R^4$ and $R^5$ together with the nitrogen atom to which they are attached form a heterocyclic ring selected from piperidinyl and piperazinyl, said heterocyclic ring being substituted by hydroxy and hydroxy-$C_{1-7}$-alkyl.
9. The compound according to claim 1, wherein
$R^4$ is hydrogen or $C_{1-7}$-alkyl, and
$R^5$ is selected from the group consisting of hydrogen,
halogen-$C_{1-7}$-alkyl, hydroxyl-$C_{1-7}$-alkyl, $C_{1-7}$-alkoxycarbonyl,
phenyl, said phenyl being unsubstituted or substituted by one, two or three groups selected from the group consisting of $C_{1-7}$-alkyl, halogen, halogen-$C_{1-7}$-alkyl and cyano,
heteroaryl, said heteroaryl being unsubstituted or substituted by one or two groups selected from the group consisting of $C_{1-7}$-alkyl, halogen and halogen-$C_{1-7}$-alkyl; and
heteroaryl-$C_{1-7}$-alkyl, said heteroaryl-$C_{1-7}$-alkyl being unsubstituted or substituted by one or two groups selected from the group consisting of $C_{1-7}$-alkyl, halogen and halogen-$C_{1-7}$-alkyl.
10. The compound according to claim 1, wherein $R^4$ is hydrogen or methyl and $R^5$ is selected from the group consisting of hydrogen, halogen-$C_{1-7}$-alkyl, hydroxy-$C_{1-7}$-alkyl, phenyl, 4-fluorophenyl, pyridin-4-ylmethyl and 6-chloropyridazin-3-yl.
11. The compound according to claim 1, wherein
$R^1$ is selected from the group consisting of
$C_{3-7}$-cycloalkyl,
$C_{3-7}$-cycloalkyl-$C_{1-7}$-alkyl, and
halogen-$C_{1-7}$-alkyl;

$R^2$ is phenyl, said phenyl being unsubstituted or substituted by one, two or three groups selected from the group consisting of $C_{1-7}$-alkyl, $C_{1-7}$-alkoxy, halogen, halogen-$C_{1-7}$-alkyl, halogen-$C_{1-7}$-alkoxy, amino, azido and cyano, or $C_{3-7}$-cycloalkyl;

$R^3$ is hydrogen, $R^4$ is hydrogen or $C_{1-7}$-alkyl, or $R^3$ and $R^4$ are —$(CH_2)_3$— and together with the nitrogen atoms to which they are attached form a 5-membered heterocyclic ring, and $R^5$ is selected from the group consisting of hydrogen, halogen-$C_{1-7}$-alkyl, hydroxyl-$C_{1-7}$-alkyl, $C_{1-7}$-alkoxycarbonyl, phenyl, said phenyl being unsubstituted or substituted by one, two or three groups selected from the group consisting of $C_{1-7}$-alkyl, halogen and halogen-$C_{1-7}$-alkyl, and heteroaryl, said heteroaryl being unsubstituted or substituted by one or two groups selected from the group consisting of $C_{1-7}$-alkyl, halogen and halogen-$C_{1-7}$-alkyl;

or $R^4$ and $R^5$ together with the nitrogen atom to which they are attached form a 4-, 5-, 6- or 7-membered heterocyclic ring optionally containing a further heteroatom or group selected from nitrogen, oxygen, sulfur, sulfinyl and sulfonyl, said heterocyclic ring being unsubstituted or substituted by one, two or three groups independently selected from $C_{1-7}$-alkyl, hydroxy, hydroxy-$C_{1-7}$-alkyl, $C_{1-7}$-alkoxy, $C_{1-7}$-alkoxy-$C_{1-7}$-alkyl, heterocyclyl-$C_{1-7}$-alkyl, $C_{1-7}$-alkylcarbonyl and $C_{1-7}$-alkylsulfonyl;

or a pharmaceutically acceptable salt thereof.

12. A pharmaceutical composition comprising the compound according to claim 1 and a pharmaceutically acceptable carrier and/or adjuvant.

13. A compound according to claim 1, selected from the group consisting of
- 5-(4-chlorophenyl)-6-(2,2,2-trifluoroethoxy)-N'-(2,2,2-trifluoroethyl)-3-pyridinecarboxylic acid hydrazide,
- 5-(4-chlorophenyl)-N-morpholino-6-(2,2,2-trifluoroethoxy)-3-pyridinecarboxamide,
- 5-(4-chloro-phenyl)-N-(1,1-dioxido-4-thiomorpholinyl)-6-(2,2,2-trifluoro-ethoxy)-3-pyridinecarboxamide,
- t-butyl 2-[(5-(4-chlorophenyl)-6-(2,2,2-trifluoroethoxy)-3-pyridinyl)carbonyl]-pyrazolidine-1-carboxylate,
- 5-(4-chloro-phenyl)-6-(2,2,2-trifluoro-ethoxy)-3-pyridinecarboxylic acid N'-methyl-N'-phenyl-hydrazide,
- 5-(4-chlorophenyl)-N-(4-hydroxypiperidin-1-yl)-6-(2,2,2-trifluoroethoxy)-3-pyridinecarboxamide,
- 5-(4-chlorophenyl)-N-(5-(morpholinomethyl)-2-oxooxazolidin-3-yl)-6-(2,2,2-trifluoroethoxy)-3-pyridinecarboxamide,
- 5-(4-chlorophenyl)-N'-(6-chloropyridazin-3-yl)-N'-methyl-6-(2,2,2-trifluoroethoxy)-3-pyridinecarboxylic acid hydrazide,
- 5-(4-chloro-3-fluorophenyl)-6-(2,2,2-trifluoroethoxy)-3-pyridinecarboxylic acid hydrazide,
- 5-(4-chlorophenyl)-6-(cyclopropylmethoxy)-N-(4-hydroxypiperidin-1-yl)-3-pyridinecarboxamide,
- 5-(4-chlorophenyl)-6-cyclobutoxy-N-(4-hydroxypiperidin-1-yl)-3-pyridinecarboxamide,
- 5-cyclohexyl-N-(4-hydroxypiperidin-1-yl)-6-(2,2,2-trifluoroethoxy)-3-pyridinecarboxamide,
- 5-(4-chlorophenyl)-N-(4-(methylsulfonyl)piperazin-1-yl)-6-(2,2,2-trifluoroethoxy)-3-pyridinecarboxamide,
- 5-cyclopentyl-N-morpholino-6-(2,2,2-trifluoroethoxy)-3-pyridinecarboxamide,
- 5-cyclopentyl-N-(2-oxopyrrolidin-1-yl)-6-(2,2,2-trifluoroethoxy)-3-pyridinecarboxamide, and pharmaceutically acceptable salts thereof.

14. A compound according to claim 1, selected from the group consisting of
- N'-(6-chloropyridazin-3-yl)-5-cyclopentyl-N'-methyl-6-(2,2,2-trifluoroethoxy)-3-pyridinecarboxylic acid hydrazide,
- (S)-5-cyclopentyl-N-(2-(methoxymethyl)pyrrolidin-1-yl)-6-(2,2,2-trifluoroethoxy)-3-pyridinecarboxamide,
- 5-cyclopentyl-N'-methyl-N'-phenyl-6-(2,2,2-trifluoroethoxy)-3-pyridinecarboxylic acid hydrazide,
- 5-cyclohexyl-N-morpholino-6-(2,2,2-trifluoroethoxy)-3-pyridinecarboxamide,
- 5-cyclohexyl-N'-methyl-N'-phenyl-6-(2,2,2-trifluoroethoxy)-3-pyridinecarboxylic acid hydrazide,
- 5-cyclohexyl-N-(pyrrolidin-1-yl)-6-(2,2,2-trifluoroethoxy)-3-pyridinecarboxamide,
- N'-(6-chloropyridazin-3-yl)-5-cyclohexyl-N'-methyl-6-(2,2,2-trifluoroethoxy)-3-pyridinecarboxylic acid hydrazide,
- 5-cyclohexyl-N—((S)-2-methoxymethyl-pyrrolidin-1-yl)-6-(2,2,2-trifluoro-ethoxy)-3-pyridinecarboxamide,
- 5-(4-chlorophenyl)-N-(4-(2-hydroxyethyl)piperidin-1-yl)-6-(2,2,2-trifluoroethoxy)-3-pyridinecarboxamide,
- 5-(4-chlorophenyl)-N-(4-(2-hydroxyethyl)piperazin-1-yl)-6-(2,2,2-trifluoroethoxy)-3-pyridinecarboxamide,
- 5-(4-chlorophenyl)-N-(4-(hydroxymethyl)piperidin-1-yl)-6-(2,2,2-trifluoroethoxy)-3-pyridinecarboxamide,
- 5-(4-chlorophenyl)-N-(4-methyl-3-oxopiperazin-1-yl)-6-(2,2,2-trifluoroethoxy)-3-pyridinecarboxamide,
- 5-(4-chlorophenyl)-N'-(3-hydroxypropyl)-N'-methyl-6-(2,2,2-trifluoroethoxy)-3-pyridinecarboxylic acid hydrazide,
- 5-(4-chlorophenyl)-N-(3-hydroxyazetidin-1-yl)-6-(2,2,2-trifluoroethoxy)-3-pyridinecarboxamide,
- 5-cyclopropyl-6-(2,2,2-trifluoro-ethoxy)-nicotinic acid N'-methyl-N'-phenyl-hydrazide, and pharmaceutically acceptable salts thereof.

15. A compound according to claim 1, selected from the group consisting of
- 5-cyclopropyl-N-(1,1-dioxo-1λ6-thiomorpholin-4-yl)-6-(2,2,2-trifluoro-ethoxy)-nicotinamide,
- 5-cyclopropyl-N-morpholin-4-yl-6-(2,2,2-trifluoro-ethoxy)-nicotinamide,
- 5-cyclopropyl-N—((S)-2-methoxymethyl-pyrrolidin-1-yl)-6-(2,2,2-trifluoro-ethoxy)-nicotinamide,
- 5-cyclopropyl-6-(2,2,2-trifluoro-ethoxy)-nicotinic acid N'-(4-fluoro-phenyl)-N'-methyl-hydrazide,
- 5-(tetrahydro-pyran-4-yl)-6-(2,2,2-trifluoro-ethoxy)-nicotinic acid N'-methyl-N'-phenyl-hydrazide,
- 5-(4-cyano-phenyl)-N-(4-hydroxy-piperidin-1-yl)-6-(2,2,2-trifluoro-ethoxy)-nicotinamide,
- 5-(4-cyano-phenyl)-N-morpholin-4-yl-6-(2,2,2-trifluoro-ethoxy)-nicotinamide,
- 5-(4-cyano-phenyl)-N-[4-(2-hydroxy-ethyl)-piperidin-1-yl]-6-(2,2,2-trifluoro-ethoxy)-nicotinamide,
- 5-[4-(2-hydroxy-ethyl)-piperidin-1-ylcarbamoyl]-2-(2,2,2-trifluoro-ethoxy)-3',4',5',6'-tetrahydro-2'H-[3,4']bipyridinyl-1'-carboxylic acid tert-butyl ester,
- 5-[N'-(4-fluoro-phenyl)-N'-methyl-hydrazinocarbonyl]-2-(2,2,2-trifluoro-ethoxy)-3',4',5',6'-tetrahydro-2'H-[3,4']bipyridinyl-1'-carboxylic acid tert-butyl ester, 5-cyclopropyl-6-cyclopropylmethoxy-nicotinic acid N'-(4-fluoro-phenyl)-N'-methyl-hydrazide,
5-cyclopropyl-6-cyclopropylmethoxy-nicotinic acid N'-methyl-N'-phenyl-hydrazide,
5-cyclopropyl-N-((2R,6S)-2,6-dimethyl-morpholin-4-yl)-6-(2,2,2-trifluoro-ethoxy)-nicotinamide,
5-cyclopropyl-6-cyclopropylmethoxy-N-((2R,6S)-2,6-dimethyl-morpholin-4-yl)-nicotinamide,
and pharmaceutically acceptable salts thereof.

16. A compound according to claim 1, selected from the group consisting of
5-cyclopropyl-6-(2,2,2-trifluoro-ethoxy)-nicotinic acid N'-pyridin-4-ylmethyl-hydrazide,
6-cyclobutoxy-5-cyclopropyl-nicotinic acid N'-(4-fluoro-phenyl)-N'-methyl-hydrazide,
6-cyclobutoxy-5-furan-2-yl-nicotinic acid N'-(4-fluoro-phenyl)-hydrazide,
5-cyclopropyl-6-(2,2,2-trifluoro-ethoxy)-nicotinic acid N'-methyl-N'-pyridin-4-yl-hydrazide,
6-cyclobutoxy-5-furan-2-yl-N-(4-hydroxy-piperidin-1-yl)-nicotinamide,
6-cyclobutoxy-5-furan-2-yl-nicotinic acid N'-(6-chloro-pyridazin-3-yl)-N'-methyl-hydrazide,
6-cyclobutoxy-5-furan-2-yl-nicotinic acid N'-methyl-N'-pyridin-4-yl-hydrazide,
5-cyclopropyl-6-cyclopropylmethoxy-nicotinic acid N'-(4-cyano-phenyl)-N'-methyl-hydrazide,
5-cyclopropyl-6-(2,2,2-trifluoro-ethoxy)-nicotinic acid N'-(4-cyano-phenyl)-N'-methyl-hydrazide,
6-cyclobutoxy-5-cyclopropyl-nicotinic acid N'-(4-cyano-phenyl)-N'-methyl-hydrazide,
5-(3-fluoro-phenyl)-6-(2,2,2-trifluoro-ethoxy)-nicotinic acid N'-methyl-N'-phenyl-hydrazide,
and pharmaceutically acceptable salts thereof.

17. A compound according to claim 1, selected from the group consisting of
5-(4-chlorophenyl)-N-(4-hydroxypiperidin-1-yl)-6-(2,2,2-trifluoroethoxy)-3-pyridinecarboxamide,
5-(4-chlorophenyl)-6-cyclobutoxy-N-(4-hydroxypiperidin-1-yl)-3-pyridinecarboxamide,
5-cyclohexyl-N-(4-hydroxypiperidin-1-yl)-6-(2,2,2-trifluoroethoxy)-3-pyridinecarboxamide,
5-(4-chlorophenyl)-N-(4-(2-hydroxyethyl)piperazin-1-yl)-6-(2,2,2-trifluoroethoxy)-3-pyridinecarboxamide,
and pharmaceutically acceptable salts thereof.

* * * * *